United States Patent [19]
Giordano et al.

[11] Patent Number: 5,807,681
[45] Date of Patent: Sep. 15, 1998

[54] HUMAN RETINOBLASTOMA-RELATED (PRB2/P130) GENOMIC DNA AND METHODS FOR DETECTING MUTATIONS THEREIN

[75] Inventors: Antonio Giordano, Philadelphia, Pa.; Alphonso Baldi, Naples, Italy

[73] Assignee: Thomas Jefferson University, Philadehia, Pa.

[21] Appl. No.: 832,883

[22] Filed: Apr. 4, 1997

Related U.S. Application Data

[60] Provisional application No. 60/014,943 Apr. 5, 1996.
[51] Int. Cl.[6] .............................. C12Q 1/68; C12P 19/34; C07H 21/04
[52] U.S. Cl. ......................... 435/6; 435/91.1; 435/91.2; 435/91.5; 536/23.1; 536/24.1; 536/24.3; 536/24.31; 536/24.33
[58] Field of Search .............................. 435/6, 91.2, 91.1, 435/91.5; 536/23.1, 24.1, 24.3, 24.31, 24.33

[56] References Cited

U.S. PATENT DOCUMENTS

| | | | |
|---|---|---|---|
| 5,340,739 | 8/1994 | Stevens et al. | 435/325 |
| 5,457,049 | 10/1995 | Giordano | 435/252.33 |
| 5,521,081 | 5/1996 | Inoaka et al. | 435/212 |
| 5,597,694 | 1/1997 | Munroe et al. | 435/6 |
| 5,654,170 | 8/1997 | Klinger et al. | 435/69.1 |

FOREIGN PATENT DOCUMENTS

| | | |
|---|---|---|
| 0 571 911 | 12/1993 | European Pat. Off. . |
| WO 93/06244 | 4/1993 | WIPO . |
| WO 94/11531 | 5/1994 | WIPO . |
| WO 95/02328 | 1/1995 | WIPO . |

OTHER PUBLICATIONS

Sinnett et al., in Database GenBank, Accession: M87919, Locus: HUMALNES53, NID: g174893, U.S. National Library of Medicine, National Institutes of Health, Apr. 1994.

Thomas et al., "A Polymorphic Dinucleotide Repeat in Instron 1 of the Human Tissue Plasminogen Acivator Gene" *Human Molecular Genetics*, 1992, vol. 1, No. 2, p. 138.

Slightrom et al., "Nucleotide Sequence Analysis of 77.7 kb of the Human V β T–Cell Receptor Gene Locus: Direct Primer–Walking Using Cosmid Template DNAs", *Genomics*, 1994, vol. 20, pp. 149–168.

Hirata et al., "Cloning and expression of cDNA for a human thromboyane $A_2$ receptor", *Nature* 14 Feb. 1991, vol. 349, pp. 617–620.

Stoppa–Lyonnet et al., "Clusters of intragenic Alu Repeats Predispose the Human C1 Inhibitor Locus to Deleterious Rearrangements", *Proc. Natl. Acad. Sci. USA*, Feb. 1990, vol. 87, pp. 1551–1555.

Whitehead et al., "Identification of Novel Members of the Serum Amyloid A Protein Superfamily as Constitutive Apo-lipoproteins of High Density Lipoprotein", *J. Biological Chemistry*, 25 Feb. 1992, vol. 267, No. 6 pp. 3862–3867.

Wilson et al., "2.2 Mb of contiguous Nucleotide Sequence from Chromosome III of C. elegans", *Nature* 3 Mar. 1994, vol. 368, pp. 32–38.

Wilson et al., "Human Hypoxanthine–Guanine Phosphori-bosyltransferase" *J. Biological Chemistry*, 25 May 1983, vol. 258, No. 10, pp. 6458–6460.

Vorechovsky et al., "Isolation of cosmid and cDNA clones in the region surrounding the TTK gene at Xq21.3–q22", *Genomics*, 1994, vol. 21 pp. 517–524.

Zheng et al., "Develoment of 124 sequence–tagged sites and cytogenetic localization of 217 cosmids for human chromo-some 10", *Genomics*, 1994 vol. 22, pp. 55–67.

Lifshitz et al., "bcr Genes and Transcripts", *Oncogene* 1988, vol. 2, pp. 113–117.

Hannon et al., *Genes & Development* 7:2378–2391 (1993).

Li et al., *Genes & Development* 7:2366–2377 (1993).

Cinti et al., *Nucleic Acids Research*, 21(24):5799–5800 (1993).

Hogg et al., *Oncogene* 7:1445–1451 (1992).

Hong et al., *Proc. Natl. Acad. Sci USA* 86:5502–5506 (Jul. 1989).

Harbour et al., *Science* 241:353–357 (15 Jul. 1988).

Baldi et al., *Journal of Cellular Biochemistry* 59:402–408 (1995).

Claudio et al., *Cancer Research* 54:5556–5560 (Nov. 1, 1994).

Sang et al., *Molecular and Cellular Differentiation* 3(1): 1–29 (1995).

Baldi et al., *Proc. Natl. Acad. Sci. USA* 93:4629–4632 (May 1996).

Claudio et al., *American Association for Cancer Research Proceedings* 36:195, #1164 (Mar. 1995).

Mayol et al., *Oncogene* 8:2561–2566 (1993).

*Primary Examiner*—Jasemine C. Chambers
*Assistant Examiner*—Scott D. Priebe
*Attorney, Agent, or Firm*—Seidel, Gonda, Lavorgina & Monaco, PC

[57] ABSTRACT

The invention provides methods for the detection of muta-tions and polymorphisms in the pRb2/p130 gene, which may be used to characterize genetic events associated with tumor formation, to trace the parental origin of mutatations, to identify carriers of germline mutations, and to identify individuals with a predisposition to cancer.

58 Claims, 3 Drawing Sheets

```
-311  CAGCCCTGTTGAATGTTCTCACGGTGGGGAGGTACGTGTTTAAAATACGG

-261  GGAAGGTGCTTTTATTTCACCCCTGGTGAAACTAGGGGAGCTAATTTTTT

-211  TAAACATGATTTTTGTCCCCCTTGAACCGCCGGCCTGGACTACGTTTCCC
                                            Ker1
-161  AGCAGCCCGTGCTCAAGACTACGGGT[GCCTGCAGGC]GGTCAGCGTCGTTT
                      →         Sp1           Sp1
-111  GCGACGGCGCAGACGCGGTGC[GGGCGG]CGGAC[GGGCGG]CGCTTCGCCGT
                                        MyoD
 -61  TTGAATTGCTGCGGGCCCGGGCCCTCACCT[CACCTG]AGGTCCGGCCGCCC

-11  AGGGGTGCGCTATGCCGTCGGGAGGTGACCAGTCGCCACCGCCCCGCCT
                 M  P  S  G  G  D  Q  S  P  P  P  P  P

40  CCCCCTCCGGCGGCGGCAGCCTCGGATGAGGAGGAGGAGGACGACGGCGA
       P  P  P  A  A  A  A  S  D  E  E  E  E  D  D  G  E

90  GGCGGAAGACGCCGCGCCGTCTGCCGAGTCGCCCACCCCTCAGATCCAGC
       A  E  D  A  A  P  S  A  E  S  P  T  P  Q  I  Q

140  AGCGGTTCGACGAGCTGTGCAGCCGCCTCAACATGGACGAGGCGGCGCGG
       Q  R  F  D  E  L  C  S  R  L  N  M  D  E  A  A  R

190  CCCGAGGCCTGGGACAGCTACCGCAGCATGAGCGAAAGCTACACGCTGGA
       P  E  A  W  D  S  Y  R  S  M  S  E  S  Y  T  L  E

240  Ggtgcgctcgc
```

FIG. 2

HUMAN RETINOBLASTOMA-RELATED (PRB2/P130) GENOMIC DNA AND METHODS FOR DETECTING MUTATIONS THEREIN

REFERENCE TO GOVERNMENT GRANT

The invention described herein was made, in part, in the course of work supported by United States Public Health Service grant CA-60999-01A1 awarded by the National Institutes of Health. The government has certain rights in the invention.

CROSS-REFERENCE TO RELATED APPLICATIONS

This application claims the benefit of U.S. provisional application Ser. No. 60/014,943 filed Apr. 5, 1996.

FIELD OF THE INVENTION

This invention relates to the gene encoding the tumor suppressor pRb2/p130, a member of the retinoblastoma protein family, and methods for screening for mutations and polymorphisms in the pRb2/p130 gene.

BACKGROUND OF THE INVENTION

Many types of human cancer are believed to be caused by an imbalance of growth regulators within a cell. A decrease in negative control growth regulators and/or their deactivation can cause a cancerous condition. Alternatively, an increase in positive control growth regulators can also cause a cancerous condition.

Since the identification of the first tumor suppressor gene, much effort in cancer research has been focused on the identification of new tumor suppressor genes and their involvement in human cancer. Many types of human cancers are thought to develop by a loss of heterozygosity of putative tumor suppressor genes not yet identified (Lasko et al., *Annu. Rev. Genetics*, 25, 281–296 (1991)) according to Knudson's "two-hit" hypothesis (Knudson, *Proc. Natl. Acad. Sci. USA,* 68, 820–823 (1971)).

One of the most studied tumor suppressor genes is the retinoblastoma susceptibility gene (Rb), whose gene product (pRb, p105, or pRb/p105) has been shown to play a key role in the regulation of cell division. In interphasic cells, pRb contributes to maintaining the quiescent state of the cell by repressing transcription of genes required for the cell cycle through interaction with transcription factors, such as E2F (Wagner et al., *Nature,* 352, 189–190 (1991); Nevins, *Science,* 258, 424–429 (1992); and Hiebert et al., *Genes Develop.,* 6, 177–185 (1992)). The loss of this activity can induce cell transformation as evidenced by the reversion of the transformed phenotype in pRb cells after replacement of a functional pRb (Huang et al., *Science* 242 1563–1565 (1988); Bookstein et al., *Science,* 247:712–715 (1990); and Sumegi et al., *Cell Growth Differ.,* 1 247–250 (1990)).

Upon entrance into the cell cycle, pRb seems to be phosphorylated by cell cycle-dependent kinases (Lees et al., *EMBO J.* 10:4279–4290 (1991); Hu et al., *Mol. Cell. Biol.,* 12:971–980 (1992); Hinds et al., *Cell,* 70:993–1006 (1992); and Matsushime et al., *Nature,* 35:295–300)) which is thought to permit its dissociation from transcription factors and, hence, the expression of genes required for progression through the cell cycle.

It has been found that the retinoblastoma protein family includes at least three members. Two other proteins, p107, and the recently cloned pRb2/p130, share regions of homology with pRb/p105, especially in two discontinuous domains which make up the "pocket region". Ewen et al., *Cell* 66:1155–1164 (1993); Mayol et al., *Oncogene* 8:1561–2566 (1993); Li et al., *Genes Dev.* 7:2366–2377 (1993); and Hannon et al., *Genes Dev.* 7:2378–2391 (1993). The pocket domain is required for binding with several viral transforming oncoproteins (Moran, *Curr. Opin. Genet. Dev.* 3:63–70 (1993)).

The pRb2/p130 cDNA and putative amino acid sequence are set forth by Li et al. The p107 cDNA and putative amino acid sequence are set forth by Ewen et al. The entire disclosures of Li et al. and Ewen et al. are incorporated herein by reference.

It has been found that pRb2/p130, as well as p107 and pRb, act as negative regulators of cell cycle progression, blocking the cells in the G1 phase (Goodrich et al., *Cell* 67:293–302 (1991); Zhu et al., *Genes Dev.* 7:1111–1125 (1993); Claudio et al., *Cancer Res.* 54:5556–5560 (1994); and Zhu et al., *EMBO J.* 14:1904–1913 (1995)). However, the three proteins exhibit different growth suppressive properties in selected cell lines, suggesting that although the different members of the retinoblastoma protein family may complement each other, they are not fully functionally redundant (Claudio et al., supra).

The mechanisms by which these three proteins exert their control on cell cycle progression are not fully understood but likely include complex formation and modulation of the activity of several transcription factors (Sang et al., *Mol. Cell. Differ.* 3:1–29 (1995)). The most studied of these complexes is the one with the E2F family of transcription factors. E2F's are heterodimeric transcription factors composed of E2F-like and DP-like subunits that regulate the expression of genes required for progression through $G_0/G_1$ S phase of the cell cycle (Lan Thangue, N. B., *Trends Biochem. Sci.* 19:108–114 (1994)).

The three proteins bind and modulate the activity of distinct E2F/DP1 complexes in different phases of the cell cycle (Sang et al., supra; Chellapan et al., *Cell* 65:1053–1061 (1991); Shirodkar et al., *Cell* 66:157–166 (1992); Cobrinik et al., *Genes Dev.* 7:2392–2404 (1993); Hijmans et al., *Mol. Cell. Biol.* 15:3082–3089 (1995); and Vairo et al., *Genes Dev.* 9:869–881 (1995)). This suggests distinct roles for these related proteins in the regulation of the cell cycle.

It has been demonstrated that the growth suppressive properties of pRb2/p130 are specific for the G1 phase. D-type cyclins, as well as transcription factor E2F-1 and E1A viral oncoproteins, were able to rescue pRb2/p130-mediated G1-growth arrest in tumor cells. This suggests that, like other Rb family proteins, the phosphorylation of pRb2/p130 is controlled by the cell cycle machinery, and that pRb2/p130 may indeed be another key G1-S phase regulator. Claudio et al., *Cancer Res.* 56, 2003–2008 (1996).

The association of pRb with transcription factors, such as E2F, has been shown to occur by interactions at a region known as the "pocket region" (Raychaudhuri et al., *Genes Develop.,* 5 1200–1207 (1991)). Recently, p107 has also been shown to exert such a binding profile (Cao et al., *Nature,* 355 176–179 (1992)). Domains A and B, along with a spacer, are believed to correspond with the "pocket region" in the pRb2/p130 gene described herein. Moreover, mutations have been found in the pocket region for several human cancers where a lack of function for the pRb protein is thought to be involved in the acquisition of the transformed phenotype (Hu et al., *EMBO J.,* 9 1147–1153 (1990); Huang et al., *Mol. Cell. Biol.,* 10:3761–3769 (1990)).

The Rb, p107, and pRb2/p130 proteins may play a key role in cell cycle regulation in that all three proteins interact with several cyclin/cdk complexes. pRb can be regulated by cyclin/cdk complexes, such as cyclin A/cdk2, cyclin E/cdk2 and cyclin D/cdk4, even if stable interaction between pRb and cyclin A/cdk2 or cyclin A/cdk2 has not been found in vivo (MacLachlan et al., *Eukaryotic Gene Exp.* 5:127–156 (1995)). On the other hand, both p107 and pRb2/p130 stably interact in vivo with cyclin E/cdk2 and cyclin A/cdk2 complexes (Li et al., supra; Ewen et al., *Science* 255:85–87 (1992); and Faha et al., *Science* 255:87–90 (1992)). These complexes may be responsible for the existence of different phosphorylated forms of pRb, p107 and pRb2/p130 in the various phases of the cell cycle (Chen et al., *Cell* 58:1193–1198 (1989); De Caprio et al., *Proc., Natl. Acad. Sci. USA* 89:1795–1798 (1992); and Beijersbergen et al., *Genes Dev.* 9:1340–1353 (1993)). In that pRb's functional activities are enhanced by these phosphorylations, it is likely that pRb2/p130 is also affected in the same manner by this post-translational modification. Since pRb2/p130 demonstrates similar, even if not redundant, functional properties to pRb, it is proposed that pRb2/p130 acts, like pRb, as a tumor suppressor gene. It has also been found that pRb2/p130 maps on the long arm of chromosome 16. This finding reinforces the notion of pRb2/p130 as a tumor suppressor gene. Chromosome 16 is a region frequently reported to show loss of heterozygosity (LOH) in several human neoplasias, such as breast, ovarian, hepatocellular and prostatic carcinomas (Yeung et al., *Oncogene* 8:3465–3468 (1993)). Chromosome 16, and specifically pRb2/p130, has also been implicated in a rare human skin disease known as hereditary cylindromatosis (HR). HR has been reported as mapping to loci on chromosome 16q12-q13. In that the pRb2/p130 gene maps to chromosome 16q12-q13, it has been put forth as a likely candidate for the tumor suppressor gene involved with the onset of this disease. Biggs et al., *Nature Genetics* 11:441–443 (December 1995).

There is a need for improved methods for identification of individuals at risk for cancer, and for the detection and evaluation of cancers.

Because the pRb2/p130 gene is a tumor suppressor gene and because it maps to a chromosomal region known to be associated with various carcinomas, there is a need for a method to screen individuals for mutations in this gene. There is also a need to identify sequence polymorphisms in this gene. It is believed that mutations, both within the exon coding sequences and the exon-intron junctions, can occur that will affect pRb2/p130's function. Direct DNA sequence analysis of individual exons taken from genomic DNA extracted from tumors has been used successfully to identify mutations of the p53 gene in ovarian carcinomas and the Rb gene in retinoblastoma tumors. Milner et al., *Cancer Research* 53:2128–2132 (1993); Yandell et al., *N. E. J. Medicine* 321:1689–1695 (1989). However, direct sequencing of exons is an undesirable approach because it is a time intensive process. An understanding of the genomic structure of the pRb2/p130 gene will enable those skilled in the art to screen a patient's DNA for polymorphisms and sequence mutations in the pRb2/p130 gene. Identification of sequence mutations will also enable the diagnosis of carriers of germline mutations of the pRb2/p130 gene and enable prenatal screening in these cases.

SUMMARY OF THE INVENTION

The present invention relates to the human pRb2/p130 gene, and methods for the detection of mutations and polymorphisms therein.

It is an object of the invention to provide a DNA segment consisting essentially of an intron of the pRb2/p130 gene, or an at least 15 nucleotide segment thereof.

Another object of the invention is to provide an amplification primer of at least 15 nucleotides consisting essentially of a DNA segment having a nucleotide sequence substantially complementary to a segment of a pRb2/p130 intron exclusive of the splice signal dinucleotides of said intron.

A further object of the invention is to provide methods for identifying polymorphisms and mutations in an exon of a human pRb2/p130 gene.

One embodiment of the invention includes a method for amplifying and identifying polymorphisms and mutations in an exon of a human pRb2/p130 gene, which method comprises:

(a) treating, under amplification conditions, a sample of genomic DNA containing the exon with a primer pair comprising a first primer which hybridizes to the promoter region or to an intron upstream of said exon and a second primer which hybridizes to an intron or to the 3'-noncoding region, said treatment producing an amplification product containing said exon;

(b) determining the nucleotide sequence of said amplification product to provide the nucleotide sequence of said exon; and (c) comparing the sequence of said exon obtained in step b to a sequence for the sequence of a corresponding wild type exon.

Each primer of the PCR primer pair consists of an amplification primer of at least 15 nucleotides consisting essentially of a DNA segment from the promoter region, from a pRb2/p130 intron exclusive of the splice signal dinucleotides, or from the 3'-noncoding region.

The amplification primer described above has a nucleotide sequence substantially complementary to the 3'-noncoding region, the promoter region given as SEQ ID NO:3, or an intron having a nucleotide sequence selected from the group consisting of SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, and SEQ ID NO:68.

In a preferred embodiment, the amplification primer as described above has a nucleotide sequence selected from the group consisting of SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO: 100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, and SEQ ID NO:112.

Another embodiment of the invention includes a method for identifying polymorphisms and mutations in an exon of a human pRb2/p130 gene, which method comprises:

(a) forming a polymerase chain reaction admixture by combining in a polymerase chain reaction buffer, a sample of genomic DNA containing said exon, a primer pair comprising a first primer which hybridizes to the promoter region or to an intron upstream of said exon and a second primer which hybridizes to the 3'-noncoding region or to an intron downstream of said exon, a mixture of one or more deoxynucleotide triphosphates, and a compound capable of radioactively labeling said primer pair, and a DNA polymerase;

(b) subjecting said admixture to a plurality of polymerase chain reaction thermocycles to produce a pRb2/p130 amplification product;

(c) denaturing said pRb2/p130 amplification product;

(d) electrophoretically separating said denatured pRb2/p130 amplification product;

(e) exposing the electrophoretically separated product of step d to a film to produce a photographic image; and (e) comparing the mobility of the bands in said photographic image of said pRb2/p130 amplification product to a electrophoretically separated amplification product for a corresponding wild type exon.

In another embodiment, the invention includes a method for identifying mutations in a human chromosomal sample containing an exon of a human pRb2/p130 gene, which method comprises:

(a) forming an admixture by combining in a buffer, a chromosomal sample containing said exon, a primer pair comprising a first primer which hybridizes to the promoter region or to an intron upstream of said exon and a second primer which hybridizes to the 3'-noncoding region or to an intron downstream of said exon, a mixture of one or more deoxynucleotide triphosphates including at least one deoxynucleotide triphosphate that is labeled, and a DNA polymerase;

(b) subjecting said admixture to a temperature and time sufficient to produce a pRb2/p130 amplification product; and (c) visualizing said pRb2/p130 amplification product with a fluorochrome conjugate specific to said label; and (d) comparing the visualized pRb2/p130 amplification product obtained in step a to a visualized amplification product for a corresponding wild type exon.

Another object of the present invention is a kit comprising some or all of the reagents, compositions, and supplies needed to carry out the methods, procedures, and techniques disclosed herein.

These and other objects will be apparent to those skilled in the art from the following discussion.

BRIEF DESCRIPTION OF THE FIGURES

FIG. 2 is the nucleotide sequence (SEQ ID NO:4) of the 5' end and 5' upstream region of the human pRb2/p130 gene showing the transcription start site (→) and the sequence complementary to a primer utilized for a primer extension analysis (underlined). Position +1 is assigned to the A of the ATG translation start codon (bold and underlined). The sequences corresponding to the Sp1 factor recognition motif are boxed. Also boxed are the sequence motifs corresponding to the MyoD and Ker1 transcription factors. The nucleotides beginning at position 1 through position 240 correspond to exon 1 of the pRb2/p130 gene (encoding the protein sequence SEQ ID NO:5). The lowercase letters beginning at position 241 represent the first ten nucleotides of intron 1.

DETAILED DESCRIPTION OF THE INVENTION

A. Abbreviations and Definitions

1. Abbreviations

Figure 1A:
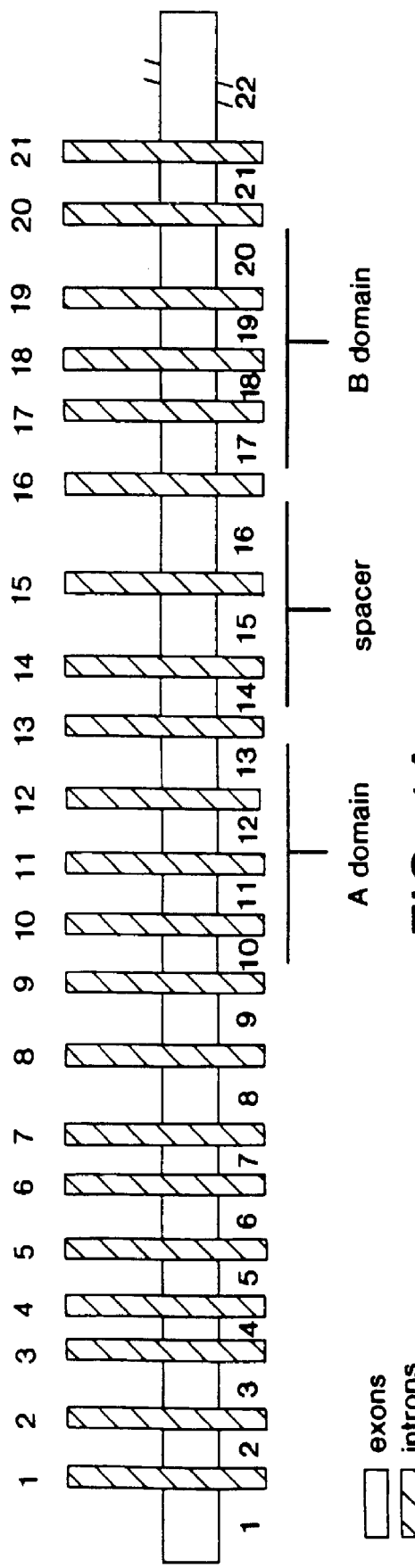
FIG. 1A is a schematic representation of the human pRb2/p130 gene. Exons are represented by open rectangles, while the introns are represented by hatched vertical bars. Exons 10–13, 14–16, and 17–20, represent domain A, a spacer, and domain B, respectively.

| | |
|---|---|
| bp | base pairs |
| BSA | Bovine Serum Albumin |
| dATP | deoxyadenosine triphosphate |
| dCTP | deoxycytidine triphosphate |
| dGTP | deoxyguanosine triphosphate |
| DIG DNA | Digoxigenin-labeled DNA |
| DIG-dUTP | Digoxigenin-deoxyuridine triphosphate |
| DNA | deoxyribonucleic acid |
| dTTP | deoxythymine triphosphate |
| EDTA | ethylene diamine tetraacetate |
| FITC | fluorescein isothiocyanate |
| PCR | polymerase chain reaction |
| PHA | phytohemagglutinin |
| PRINS | oligonucleotide-PRimed IN Situ synthesis |
| RNA | ribonucleic acid |
| SDS | sodium dodecyl sulfate |
| SSC | standard saline citrate |
| SSCP | single-strand conformation polymorphism |
| TBE | buffer mixture of 0.09M tris, 0.09M boric acid, and 2.5 mM EDTA |

2. Definitions

"Allele" refers to one or more alternative forms of a gene occupying a given locus on a chromosome.

"Amplification product" refers to a nucleic acid segment produced under amplification procedures such as PCR, SSCP, and PRINS, which product is complementary to the template segment amplified.

"Downstream" identifies sequences which are located in the direction of expression, i.e., on the 3'-side of a given site in a nucleic acid.

"Genomic DNA" refers to all of the DNA sequences composing the genome of a cell or organism. In the invention described herein it includes the exons, introns, and regulatory elements for the pRb2/p130 gene.

"Hybridization" means the Watson-Crick base-pairing of essentially complementary nucleotide sequences (polymers of nucleic acids) to form a double-stranded molecule.

"3'-noncoding region" means those nucleic acid sequences downstream of the termination codon.

"Polymorphic" refers to the simultaneous occurrence in the population of genomes showing allelic variations. As used herein the term encompasses alleles producing different phenotypes, as well as proteins for which amino acid variants exist in a population, but for which the variants do not destroy the protein's function.

"Primer" refers to an oligonucleotide which contains a free 3' hydroxyl group that forms base pairs with a complementary template strand and is capable of acting as the starting point for nucleic acid synthesis by a polymerase. The primer can be single-stranded or double-stranded, however, if in double-stranded form, the primer is first treated in such a way so as to separate it from its complementary strand.

"pRb2/p130 gene" means the gene which encodes the pRb2/p130 protein, the cDNA of which is set out as SEQ ID NO: 1, and all allelic variations and mutants thereof.

"pRb2/p130 intron" as used herein means a wild type intron segment of the pRb2/p130 gene, as well as any allelic variations thereof.

"pRb2/p130 protein" means the translation product of the pRb2/p130 gene, including all allelic variations and mutants thereof.

"Splice junction" or "exon-intron junction" refers to the nucleotide sequence immediately surrounding an exon-intron boundary of a nuclear gene. As used herein the term includes the sites of breakage and reunion in the mechanism of RNA splicing.

"Splice signal dinucleotide" refers to the first two nucleotides (5'-terminal) or the last two nucleotides (3'-terminal) of an intron. In highly conserved genes the 5'-terminal dinucleotide is GT and the 3'-terminal dinucleotide is AG. Alternatively, the 5'-terminal dinucleotide and the 3'-terminal dinucleotide are referred to as the "donor" and "acceptor" sites, respectively.

"Substantially complementary nucleotide sequence" means, as between two nucleotide sequences, a relationship such that the sequences demonstrate sufficient Watson-Crick base-pair matching to enable formation of a hybrid duplex under hybridization conditions. It is not required, however, that the base-pair matchings be exact.

"Upstream" identifies sequences which are located in the direction opposite from expression, i.e. on the 5'-side of a given site in a nucleic acid.

B. The Genomic Structure of pRb2/p130

The genomic structure of the human pRb2/p130 gene is described herein. The pRb2/p130 genomic DNA has been cloned and sequenced. The pRb2/p130 gene has been mapped to the long arm of chromosome 16, an area previously reported to show loss of heterozygosity (LOH) for human neoplasias. The putative promoter for pRb2/p130 has been identified, cloned and sequenced. The complete intron-exon organization of the gene has been elucidated. The pRb2/p130 gene contains 22 exons and 21 introns, spanning over 50 kb of genomic DNA. The length of the individual exons ranges from 65 bp to 1517 bp, while the length of individual introns ranges from 82 bp to 9837 bp. The organization of these exons and introns are shown in FIG. 1A. The location and size of each exon and intron of pRb2/p130, as well as the nucleotide sequences at the exon-intron junctions are shown below in Table 1. (SEQ ID NOS:6–47). The exon sequences are shown in upper case letters, while the intron sequences are in lower case letters. The superscript numbers correspond to the nucleotide positions of the exon-intron boundaries on SEQ ID NO: 1.

All the exons were completely sequenced and no discrepancies were found in comparing the genomic sequence of the exons and the cDNA sequence previously reported. Li, Y. et al., Genes 7:2366–2377 (1993). The exon-intron boundaries were determined by comparing the sequence of the genomic DNA described herein to the published cDNA sequence of Li et al., supra. The exon-intron boundaries were identified as the positions where the genomic DNA sequence diverged from that of the cDNA.

With the exception of exon 22, the largest of all the exons (1517 bp in length), the exons found were relatively small, with the shortest, exons 4 and 7, comprising only 65 nucleotides each. Exons 10 through 20 code for the region of the pRb2/p130 protein which form the "pocket region". Exons 10 through 13 and 17 through 20 translate to Domain A and Domain B, respectively. Exons 14, 15, and 16 code for the region of the pRb2/p130 protein, known as the "spacer." The spacer lies between Domains A and B.

The introns have been completely sequenced. The shortest intron, intron 16, lying between exons 16 and 17, is only 82 bp in length, whereas the largest intron, intron 21, spans 9837 bp. Intron 21 is located between exons 21 and 22. The complete sequences for the introns are given as SEQ ID NOS: 48–68. All of the intron sequences of pRb2/p130 conform to the GT-AG rule found to be characteristic of other human genes. Breathnach, R. et al., Annu. Rev. Biochem. 50:349–383 (1981). This rule identifies the generic sequence of an intron as GT... ...AG. Introns having this generic form are characterized as conforming to the GT-AG rule. The two dinucleotides, GT and AG, known as the "splice signal dinucleotides," act as signals for splicing out the introns during the processing of the pRb2/p130 mRNA. Point mutations in splice signal dinucleotides have been associated with aberrant splicing in other genes in vivo and in vitro. See generally, Genes V, B. Lewin, Oxford University Press, pp. 913–916, New York (1994) and Yandell et al., supra at p. 1694. Thus, it is important to identify any mutations to the splice signal dinucleotides or other sequences that are excluded from the RNA transcript during splicing.

The pRb2/p130 genomic structure and intron sequences described herein may be used to delineate mutations and rearrangements associated with tumor formation. The genomic structure and intron sequences herein may also be used to screen for naturally occurring polymorphisms at the nucleotide level. Knowledge of a specific single polymorphism can be used to eliminate a mutation in pRb2/p130 as a causative factor in a tumor if the purported mutation displays the same pattern as the polymorphism. Knowledge of polymorphisms in pRb2/p130 can be used to determine the genetic linkage of an identical mutation, and in turn, the tracing of parental origin and family histories without the need for time for time intensive sequencing if mutation is of germline origin. These polymorphisms can then be utilized for the development of diagnostic approaches for human neoplasias. However, it should be noted that not all polymorphisms are of equal utility in these applications. It is preferable to seek out mutations in the exons, as these mutations are most likely to lead to tumor development. Further, because the coding regions of the gene are generally more stable and less likely to mutate over time, it follows that polymorphisms in the exon region are typically less common. The detection of a polymorphism in the exon region of pRb2/p130 would enable screening of both genomic DNA and cDNA.

In the examples that follow, several screening methods are exemplified to identify pRb2/p130 mutations and polymorphisms.

C. Transcriptional Control of pRb2/p130

There is evidence that tumor suppressor gene products directly interact with transcription factors, such as MyoD, which regulate not only cell growth, but also cell differentiation. Sang et al., supra at p. 8. Mutations in the sequence region motifs for these transcription factors would be expected to effect the function of the tumor suppressor genes. Accordingly, in addition to identifying the genomic structure of the pRb2/p130 gene, additional experiments were conducted to define the 5'-flanking promoter sequence of pRb2/p130. Part of the putative promotor sequence for pRb2/p130, along with the entire sequence of the first exon and the beginning of the first intron is shown in FIG. 2 (SEQ ID NO:4). The full sequence for the putative promoter region is given in SEQ ID NO:3.

Figure 3:
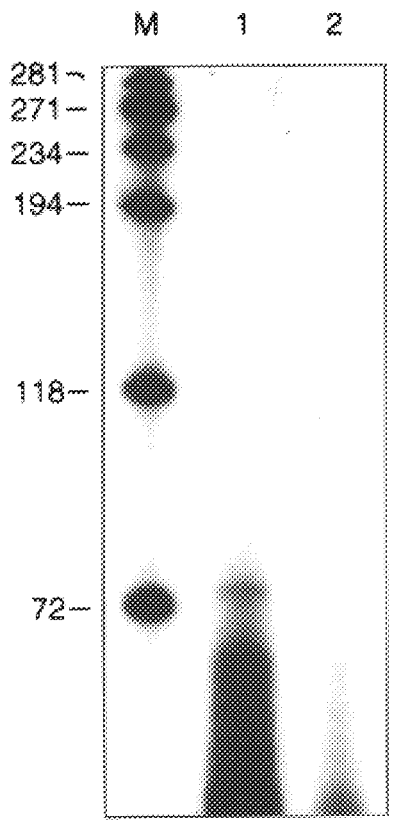
FIG. 3 shows the products of a primer extension experiment done to identify the transcription start site for the human pRb2/p130 gene. Cytoplasmatic RNA was hybridized overnight to an oligonucleotide complementary to the twenty four nucleotides beginning at position –22 of FIG. 2 (SEQ ID NO:4). Lane M contains the molecular-weight marker (φχ174 DNA/Hae III, Promega). Lanes 1 and 2 contain the primer-extended product of pRb2/p130 from HeLa cells and tRNA as template, respectively.

To characterize the pRb2/p130 promoter, a primer extension analysis was performed to locate the transcription initiation site. The protocol for the primer-extension analysis is given in the examples that follow. A twenty four nucleotide segment (SEQ ID NO: 113) containing the antisense-strand sequence 26 to 50 nucleotides upstream from the putative ATG codon (See FIG. 2) was end-labeled and used as a primer for an extension reaction on cyctoplasmatic RNA from HeLa cells. As shown in FIG. 3, a major extended fragment of 78 bp was detected (lane 1) from the primer extension done with HeLa cells as the template. The additional bands detected by the primer extension analysis could represent additional initiation sites. This finding (lane 1) is consistent with a transcription initiation site 99 nucleotides upstream of the start codon. On the contrary, there was no primer extension product observed when tRNA was used as a template (lane 2). The probable position of the identified transcription initiation site within the promoter sequence is indicated by the arrow in FIG. 2. The primer extension analysis was repeated three times, and similar results were produced in each instance.

The putative transcription factor-binding sites were identified by their similarity to consensus sequences for known transcription factor-binding sites by use of the SIGNAL SCAN program. A description of this program is included in the examples that follow. The most recognizable sequence motifs are for the transcription factors Sp1 (two sites), Ker1 and MyoD. FIG. 2 shows the location of these motifs. Ker1 is involved in keratinocyte-specific transcription, while MyoD is involved in myogenesis. Leask et al., *Genes Dev.* 4:1985–1998 (1990); Weintraub, H., *Cell* 75:1241–1244 (1993). The presence in the promoter region for pRb2/p130 of these sequence motifs supports a hypothesis of an involvement of this gene in the complex pathways regulating differentiation of specific cell systems.

D. Detection of Mutations in pRb2/p130

The present invention provides a method for amplifying the genomic DNA of pRb2/p130 and for screening polymorphisms and mutations therein. The assay methods described herein can be used to diagnose and characterize certain cancers or to identify a heterozygous carrier state. While examples of methods for amplifying and detecting mutations in pRb2/p130 are given, the invention is not limited to the specific methods exemplified. Other means of amplification and identification that rely on the use of the genomic DNA sequence for pRb2/p130 and/or the use of the primers described herein are also contemplated by this invention.

Generally, the methods described herein involve preparing a nucleic acid sample for screening and then assaying the sample for mutations in one or more alleles. The nuclei acid sample is obtained from cells. Cellular sources of genomic DNA include cultured cell lines, or isolated cells or cell types obtained from tissue (or whole organs or entire organisms). Preferably, the cell source is peripheral blood lymphocytes. Methods of DNA extraction from blood and tissue samples are known to those skilled in the art. See, for example, Blin et al., *Nuc. Acids Res.* 3:2303–2308 (1976); and Sambrook et al., Molecular *Cloning:A Laboratory Manual*, Second Edition, pp. 9.16–9.23, Cold Spring Harbor Laboratory Press, Cold Spring Harbor, N.Y. (1989), the entire disclosure of which is incorporated herein by reference. If the patient sample to be screened is in the form of double-stranded genomic DNA, it is first denatured using methods known to those skilled in the art. Denaturation can be carried out either by melting or subjecting the strands to agents that destabilize the hydrogen bonds, such as alkaline solutions and concentrated solutions of formamide or urea.

In one embodiment of the invention, prior to screening the genomic DNA sample, the pRb2/p130 genomic DNA sample is amplified by use of the polymerase chain reaction (PCR), using a primer pair, a buffer mixture, and an enzyme capable of promoting chain elongation. Methods of conducting PCR are well known to those skilled in the art. See, for example, Beutler et al., U.S. Pat. No. 5,234,811, or Templeton, N. S., *Diag. Mol. Path.* 1(1):58–72 (1992), which are incorporated herein by reference as if set forth at length. The amplification product produced from PCR can then be used to screen for mutations using the techniques known as Single Strand Conformational Polymorphism (SSCP) or Primed In-Situ DNA synthesis (PRINS). Of course, mutations can also be identified through the more laborious task of sequencing the gene isolates of a patient and comparing the sequence to that for the corresponding wild type pRb2/p130 segment.

PCR is carried out by thermocycling, i.e., repeated cycles of heating and cooling the PCR reaction mixture, within a temperature range whose lower end is 37° C. to 55° C. and upper end is around 90° C. to 100° C. The specific temperature range chosen is dependent upon the enzyme chosen and the specificity or stringency required. Lower end temperatures are typically used for annealing in amplifications in which high specificity is not required and conversely, higher end temperatures are used where greater stringency is necessary. An example of the latter is when the goal is to amplify one specific target DNA from genomic DNA. A higher annealing temperature will produce fewer DNA segments that are not of the desired sequence. Preferably, for the invention described herein, the annealing temperature is between 50° C. and 65° C. Most preferably, the annealing temperature is 55° C.

The PCR is generally performed in a buffered aqueous solution, i.e., a PCR buffer, preferably at a pH of 7–9, most preferably about 8. Typically, a molar excess of the primar is mixed with the buffer containing the template strand. For genomic DNA, this ratio is typically $10^6$:1 (primer: template). The PCR buffer also contains the deoxynucleotide triphosphates (dATP, dCTP, dGTP, and dTTP) and a polymerase. Polymerases suitable for use in PCR include, but are not limited to, *E. coli* DNA polymerase I, the Klenow fragment of *E. coli* DNA polymerase I, T4 DNA polymerase, T7 DNA polymerase, Taq DNA polymerase (*Thermus aquaticus* DNA polymerase I), and other heat-stable enzymes which will facilitate the formation of amplification products.

The primers used herein can be naturally occurring oligonucleotides purified from a nucleic acid restriction digest or produced synthetically using any suitable method, which methods are known to those skilled in the art. The primers used herein can be synthesized using automated methods.

Because a mutation can occur in both the exon itself and the splice junction, it is necessary to design primers that will ensure that the entire exon region to be analyzed is amplified. To amplify the entire exon, the oligonucleotide primer for any given exon must be designed such that it includes a portion of the complementary sequence for the promoter region, for the 3'-noncoding region, or for the introns flanking the exon to be amplified, provided however that the primer sequence should not include the sequence for the splice signal dinucleotides. It is important to exclude the complementary sequence for the splice signal dinucleotides from the primer in order to ensure that the entire region, including the splice signal dinucleotide, is amplified. Including the complementary sequences to the splice signal dinucleotides could result in an amplification product that "plasters over" the splice junction and masks any potential mutation that could occur therein. It should be noted, however, that the introns flanking the exon are not limited to the introns immediately adjacent to the exon to be amplified. The oligonucleotide primer can be designed such that it includes a portion of the complementary sequence for the introns upstream or downstream from the exon to exon to be amplified. In the latter instance, the amplification product produced would include more than one exon. Preferably at least 20 to 25 nucleotides of the sequence for each flanking intron are included in the primer sequence.

The primers used herein are selected to be substantially complementary to each strand of the pRb2/p130 segment to be amplified. There must be sufficient base-pair matching to enable formation of a hybrid duplex under hybridization conditions. It is not required, however, that the base-pair matchings be exact. Therefore, the primer sequence may or may not reflect the exact sequence of the pRb2/p130 segment to be amplified. Non-complementary bases or longer sequences can be interspersed into the primer, provided the primer sequence retains sufficient complementarity with the segment to be amplified and thereby form an amplification product.

The primers must be sufficiently long to prime the synthesis of amplification products in the presence of a polymerizing agent. The exact length of the primer to be used is dependent on many factors including, but not limited to, temperature and the source of the primer. Preferably the primer is comprised of 15 to 30 nucleotides, more preferably 18 to 27 nucleotides, and most preferably 24 to 25 nucleotides. Shorter primers generally require cooler annealing temperatures with which to form a stable hybrid complex with the template.

Primer pairs are usually the same length, however, the length of some primers was altered to obtain primer pairs with identical annealing temperatures. Primers of less than 15 bp are generally considered to generate non-specific amplification products.

According to one embodiment of this invention, SSCP is used to analyze polymorphisms and mutations in the exons of pRb2/p130. SSCP has the advantages over direct sequencing in that it is simple, fast, and efficient. The analysis is performed according to the method of Orita et al., *Genomics* 5:874–879 (1989), the entire disclosure of which is incorporated herein by reference. The target sequence is amplified and labeled simultaneously by the use of PCR with radioactively labeled primers or deoxynucleotides. Neither in situ hybridization nor the use of restriction enzymes is necessary for SSCP.

SSCP detects sequence changes, including single-base substitutions (point mutations), as shifts in the electrophoretic mobility of a molecule within a gel matrix. A single nucleotide difference between two similar sequences is sufficient to alter the folded structure of one relative to the other. This conformational change is detected by the appearance of a band shift in the tumor DNA, when compared with the banding pattern for a corresponding wild type DNA segment. Single base pair mutations can be detected following SSCP analysis of PCR products up to about 400 bp. PCR products larger than this size must first be digested with a restriction enzyme to produce smaller fragments.

In another embodiment of the invention, sequence mutations in pRb2/p130 can be detected utilizing the PRINS technique. The PRINS method represents a versatile technique, which combines the accuracy of molecular and cytogenetic techniques, to provide a physical localization of the genes in nuclei and chromosomes. See Cinti et al., *Nuc. Acids Res.* Vol 21, No. 24:5799–5800 (1993), the entire disclosure of which is incorporated herein by reference. The PRINS technique is based on the sequence specific annealing of unlabeled oligodeoxynucleotides in situ. The oligodeoxynucleotides operate as a primer for in situ chain elongation catalyzed by Taq I polymerase. Labeled nucleotides, labeled with a substance such as biotin or Digoxigenin, act as substrate for chain elongation. The labeled DNA chain is visualized by exposure to a fluorochrome-conjugated antibody specific for the label substance. Preferably, the label is Digoxigenin and the fluorochrome conjugated antibody is anti-Digoxigenin-FITC. This results in the incorporation of a number of labeled nucleotides far greater than the number of nucleotides in the primer itself. Additionally, the specificity of the hybridization is not vulnerable to the problems that arise when labeled nucleotides are placed in the primer. The bound label will only be found in those places where the primer is annealed and elongated.

Neither the SSCP nor the PRINS technique will characterize the specific nature of the polymorphism or mutation detected. If a band shift is detected through use of SSCP analysis, one must still sequence the sample segment and compare the sequence to that of the corresponding wild type pRb2/p130 segment. Similarly, if the absence of one or both of the alleles for a given exon segment is detected by the PRINS technique, the sequence of the segment must be determined and compared to the nucleotide sequence for the corresponding wild type in order to determine the exact location and nature of the mutation, i.e., point mutation, deletion or insertion. The PRINS technique is not capable of detecting polymorphisms.

Protocols for the use of the SSCP analysis and the PRINS technique are included in the examples that follow.

The PRINS method of detecting mutations in the pRb2/p130 gene may be practiced in kit form. In such an embodiment, a carrier is compartmentalized to receive one or more containers, such as vials or test tubes, in close confinement. A first container may contain one or more subcontainers, segments or divisions to hold a DNA sample for drying, dehydrating or denaturing. A second container may contain the PRINS reaction mixture, which mixture is comprised of a PCR buffer, a DIG DNA labeling mixture, a polymerase such as Taq I DNA polymerase, and the primers designed in accordance with this invention (see Example 3, Table 2). The DIG DNA labeling mixture is comprised of a mixture of labeled and unlabeled deoxynucleotides. Preferably, the labeled nucleotides are labeled with either biotin or Digoxigenin. More preferably, the label is Digoxigenin. A third container may contain a fluorochrome conjugated antibody specific to the label. The fluorochrome conjugated antibody specific for Digoxigenin is anti-Digoxigenin-FITC. Suitable conjugated fluorochromes for biotin include avidin-FITC or avidin Texas Red. The fourth container may contain a staining compound, preferably Propidium Iodide (PI). The kit may further contain appropriate washing and dilution solutions.

EXAMPLES

The following examples illustrate the invention. These examples are illustrative only, and do not limit the scope of the invention.

EXAMPLE 1

Isolation and Characterization of Genomic Clones

A. Isolation of Genomic Clones

To isolate the entire human pRb2/p130 gene, a human P1 genomic library (Genome System Inc., St. Louis, Mo.) was screened by using two primers made from the published cDNA sequence, Li et al., *Genes Dev.* 7:2366–2377 (1993). The sequences for the primers used to isolate the genomic clones are GTATACCATTTAGCAGCTGTCCGCC (SEQ ID NO:115) and the complement to the sequence GTGT-GCCATTTATGTGATGGCAAAG (SEQ ID NO:114).

Figure 1B:
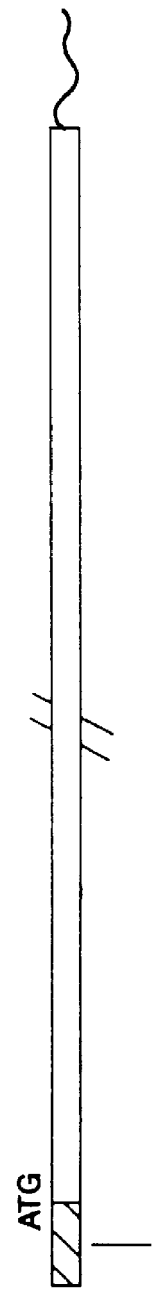
FIG. 1B is a schematic representation of the human pRb2/p130 genomic clones derived from the P1 and λ phage libraries.

One of the clones identified upon screening the P1 genomic library (clone no. 1437, FIG. 1B) was confirmed by Southern blot hybridization to contain a part of the pRb2/p130 gene. To obtain the additional 5' flanking sequence of the pRb2/p130 gene containing the putative promoter region, a human placenta genomic DNA phage library (EMBL3 SP6/T7) from Clontech, Palo Alto, Calif. was screened with a cDNA probe according to the method of Sambrook et al., *Molecular Cloning:A Laboratory Manual*, Second Edition, pp. 12.30–12.38, Cold Spring Harbor Laboratory Press, Cold Spring Harbor, N.Y. (1989), the entire disclosure of which is incorporated herein by reference. The cDNA probe, labeled with [$\gamma$-$^{32}$P], corresponded to the first 430 bp after the start codon of the published cDNA sequence, Li et al., supra. Of the two positive clones obtained, one, identified as $\phi$SCR3 (FIG. 1B), was determined to contain the 5' flanking region of the pRb2/p130 gene.

B. Identification of Exon/intron Boundaries

To precisely characterize the position of the exons and the exon/intron boundaries in the genomic DNA, a set of oligonucleotide primers were used to sequence the genomic DNA clones. The primers were synthesized based upon the cDNA nucleotide sequence of pRb2/p130 such that they annealed to the genomic DNA at roughly 150 bp intervals. The exon/intron boundaries were identified from those positions in which the genomic DNA sequence differed from that of the published cDNA sequence.

C. Sequencing of Clones

Sequencing of the recombinant clones was carried out in part by automated DNA sequencing using the dideoxy terminator reaction chemistry for sequence analysis on the Applied Biosystem Model 373A DNA sequencer and, in part, by using a dsDNA Cycle Sequencing System kit purchased from GIBCO BRL, Gaithersburg, Md., according to the instructions of the manufacturer.

D. Synthesis of Oligonucleotide Primers

All oligonucleotide primers used herein were synthesized using Applied Biosystems DNA-RNA synthesizer Model 394, using beta-cyanoethyl phosphoramidite chemistry.

E. Results of the Genomic Clones Characterization

The human pRb2/p130 gene consists of 22 exons and 21 introns and spans more than 50 kb of genomic DNA. The organization of these exons and introns are shown in FIG. 1A. The location and size of each exon and intron of pRb2/p130, as well as the nucleotide sequences at the exon-intron boundaries are shown in Table 1 (SEQ ID NOS:6–47). The exons range in size from 65 to 1517 bp in length. The introns, which range in size from 82–9837 bp in length, have been completely sequenced. The nucleotide sequences are given as SEQ ID NOS:48–68.

TABLE 1

Exon-Intron Boundaries of the Human pRb2/p130 Gene

| Exon No. (bp) | 5' Donor sequence | 3' Acceptor sequence | Intron No. (bp) |
|---|---|---|---|
| 1(240) | ACGCTGGAG$^{309}$gtgcgctcgc (SEQ ID NO: 6) | tcttttacag$^{310}$GGAAATGAT (SEQ ID NO: 7) | 1(4220) (SEQ ID NO: 66) |
| 2(131) | AGAGCAGAG$^{440}$gtaactatgt (SEQ ID NO: 8) | ttaataccag$^{441}$CTTAATCGA (SEQ ID NO: 9) | 2(3507) (SEQ ID NO: 67) |
| 3(201) | GAAACAGCG$^{641}$gtaggtttc (SEQ ID NO: 10) | tcccccaaag$^{642}$GCGACAGCC (SEQ ID NO: 11) | 3(3865) (SEQ ID NO: 48) |
| 4(65) | ATGCAAAAG$^{706}$gtaagaaaat (SEQ ID NO: 12) | aatcctgcag$^{707}$GTAATTTCC (SEQ ID NO: 13) | 4(4576) (SEQ ID NO: 49) |
| 5(129) | ATTTTAAAG$^{835}$gtaggtttgt (SEQ ID NO: 14) | acaccatag$^{836}$GCTTATCTG (SEQ ID NO: 15) | 5(1618) (SEQ ID NO: 50) |
| 6(161) | GAAAAAAAG$^{996}$gtttgtaagt (SEQ ID NO: 16) | ttcatcatag$^{997}$CTCCTTAAG (SEQ ID NO: 17) | 6(92) (SEQ ID NO: 51) |
| 7(65) | AGAGAGTTT$^{1061}$gtgagtactt (SEQ ID NO: 18) | ttcctatag$^{1062}$TAAAGCCAT (SEQ ID NO: 19) | 7(889) (SEQ ID NO: 52) |
| 8(187) | TTTGACAAG$^{1248}$gtgagtttag (SEQ ID NO: 20) | ttttcttag$^{1249}$TCCAAAGCA (SEQ ID NO: 21) | 8(4586) (SEQ ID NO: 53) |
| 9(167) | GATTCTCAG$^{1415}$gttagtttga (SEQ ID NO: 22) | cctttttag$^{1416}$GACATGTTC (SEQ ID NO: 23) | 9(2127) (SEQ ID NO: 54) |
| 10(90) | GTGCTAAAG$^{1525}$gtaattgtgc (SEQ ID NO: 24) | atttctacag$^{1526}$AAATTGCCA (SEQ ID NO: 25) | 10(716) (SEQ ID NO: 55) |
| 11(104) | GATTTATCT$^{1629}$gtgagtaaaa (SEQ ID NO: 26) | attttatag$^{1630}$GGTATTCTG (SEQ ID NO: 27) | 11(837) (SEQ ID NO: 56) |
| 12(138) | TTTTATAAG$^{1767}$gtatttccca (SEQ ID NO: 28) | tttatttcag$^{1768}$GTGATAGAA (SEQ ID NO: 29) | 12(1081) (SEQ ID NO: 57) |
| 13(165) | TGTGAAGAG$^{1932}$gtgaaaatca (SEQ ID NO: 30) | tcttcatag$^{1933}$GTCATGCCA (SEQ ID NO: 31) | 13(1455) (SEQ ID NO: 58) |
| 14(112) | TTGGAAGGA$^{2044}$gtaagtttaa (SEQ ID NO: 32) | ttgacccctag$^{2045}$GCATAACAT (SEQ ID NO: 33) | 14(2741) (SEQ ID NO: 59) |
| 15(270) | CTGTGCAAG$^{2314}$gtaaggaagg | ctgtcactag$^{2315}$GTATTGCCA | 15(197) |

TABLE 1-continued

Exon-Intron Boundaries of the Human pRb2/p130 Gene

| Exon No. (bp) | 5' Donor sequence | 3' Acceptor sequence | Intron No. (bp) |
|---|---|---|---|
| | (SEQ ID NO: 34) | (SEQ ID NO: 35) | (SEQ ID NO: 60) |
| 16(281) | TTTAGAAAG$^{2595}$gtaatttttc | tatctcctag$^{2596}$GTATACCAT | 16(82) |
| | (SEQ ID NO: 36) | (SEQ ID NO: 37) | (SEQ ID NO: 61) |
| 17(177) | ATGGCAAAG$^{2772}$gtgagtacca | gtttgccag$^{2773}$GTCACAAAA | 17(1079) |
| | (SEQ ID NO: 38) | (SEQ ID NO: 39) | (SEQ ID NO: 62) |
| 18(72) | CGGAGCCAG$^{2844}$gtaactacat | ttctctaaag$^{2845}$GTGTATAGA | 18(659) |
| | (SEQ ID NO: 40) | (SEQ ID NO: 41) | (SEQ ID NO: 63) |
| 19(107) | AAGATAGAA$^{2950}$gtgggatctt | ctggctgcag$^{2951}$CCAGTAGAG | 19(572) |
| | (SEQ ID NO: 42) | (SEQ ID NO: 43) | (SEQ ID NO: 64) |
| 20(202) | CAGGCAAAT$^{3153}$gtaagtatga | tttttaaacag$^{3154}$ATGGGATGC | 20(901) |
| | (SEQ ID NO: 44) | (SEQ ID NO: 45) | (SEQ ID NO: 65) |
| 21(165) | CCTTCAAAG$^{3318}$gtgagcctaa | cccaccatag$^{3319}$AGACTGAGA | 21(9837) |
| | (SEQ ID NO: 46) | (SEQ ID NO: 47) | (SEQ ID NO: 68) |
| 22(1517) | to the polyadenylation signal | | |

EXAMPLE 2

Characterization of Transcriptional Control Elements

A. Cell Culture and RNA Extraction

The human HeLa (cervix epithelioid carcinoma) cell line was obtained from the American Type Culture Collection and maintained in culture in Dulbecco's modified Eagle medium (DHEM) with 10% fetal calf serum (FCS) at 37° C. in a 10% $CO_2$-containing atmosphere. Cytoplasmatic RNA was extracted utilizing the RNAzol B method (CINNA/BIOTECX, Friendswood, Tex.).

B. Primer Extension Analysis

To characterize the pRb2/p130 promoter, a primer extension analysis was performed to locate the transcription initiation site. The primer for this analysis was an oligonucleotide, 5'ACCTCAGGTGAGGTGAGGGC-CCGG 3' (SEQ ID NO: 113), complementary to the pRb2/p130 genomic DNA sequence starting at position −22 (See FIG. 2, SEQ ID NO:4). The primer was end labeled with [$\gamma^{32}$P]ATP and hybridized overnight with 20 μg of HeLa cytoplasmatic RNA at 42° C. The primer-annealed RNA was converted into cDNA by avian myeloblastosis virus reverse transcriptase in the presence of 2 mM deoxynucleotides at 42° C. for 45 minutes. The cDNA product was then analyzed on 7% sequencing gel containing 8M urea. The position of the transcription start site was mapped from the length of the resulting extension product.

C. SIGNAL SCAN Program

Several of the transcription factor-binding motifs were identified through the use of SIGNAL SCAN VERSION 4.0. SIGNAL SCAN is a computer program that was developed by Advanced Biosciences Computing Center at the University of Minnesota, St. Paul, Minn. This program aids molecular biologists in finding potential transcription factor binding sites and other elements in a DNA sequence. A complete description of the program can be found in Prestridge, D. S., *CABIOS* 7:203–206 (1991), the entire disclosure of which is incorporated herein as if set forth at length.

SIGNAL SCAN finds sequence homologies between published signal sequences and an unknown sequence. A signal, as defined herein, is any short DNA sequence that may have known significance. Most of the known signals represent transcriptional elements. The program does not interpret the significance of the identified homologies; interpretation of the significance of sequences identified is left up to the user. The significance of the signal elements varies with the signal length, with matches to short segments having a higher probability of random occurrence.

D. Results of the Primer Extension Analysis And SIGNAL SCAN

FIG. 3 shows the results of the primer extension analysis done to locate the transcription initiation site for pRb2/p130. A major extended fragment of 78 bp was detected (lane 1) from the primer extension done with HeLa Cells as the template. The probable position of the identified transcription start site is indicated by the arrow in FIG. 2. Putative transcription factor-binding sites were identified by their similarity to consensus sequences for known transcription factor-binding sites. The sequence motifs corresponding to Sp1, Ker1, and MyoD are also indicated in FIG. 2.

EXAMPLE 3

Detection of Heterozygous Mutations By PCR

A. Preparation of Genomic DNA

The genomic DNA used herein was obtained from human peripheral blood lymphocytes. The samples were prepared by the methods of Sambrook et al., *Molecular Cloning:A Laboratory Manual*, Second Edition, pp. 9.16–9.23, Cold Spring Harbor Laboratory Press, Cold Spring Harbor, N.Y. (1989).

B. Synthesis Of PCR Primers

The PCR primers used herein were synthesized as described in Example 1D. The specific primer sequences used and their annealing temperatures are given in Table 2, as SEQ ID NOS:69 to 112.

TABLE 2

| Exon Amplified | Sequence Of Primer (5'-3') | Annealing Temperature (°C.) | Size Of PCR Product (bp) |
|---|---|---|---|
| Exon 1 | TTCGCCGTTTGAATTGCTGC (SEQ ID NO: 93) | 55 | 359 |
| Exon 1 (rev) | ACCGGTTCACACCAACTAGG (SEQ ID NO: 94) | | |
| Exon 2 | GAGATAGGGTCATCATTGAAAC (SEQ ID NO: 95) | 55 | 206 |
| Exon 2 (rev) | CATTAGCCATACTCTACTTGT (SEQ ID NO: 96) | | |
| Exon 3 | GCTAATTAACTCTGTAACTGC (SEQ ID NO: 97) | 55 | 327 |
| Exon 3 | CACTGCAGCACAGACTAATGTGT | | |

TABLE 2-continued

| Exon Amplified | Sequence Of Primer (5'-3') | Annealing Temperature (°C.) | Size Of PCR Product (bp) |
|---|---|---|---|
| (rev) | (SEQ ID NO: 98) | | |
| Exon 4 | TCTCTCCCTTTAACTGTGGGTTT (SEQ ID NO: 99) | 55 | 245 |
| Exon 4 (rev) | GGAGTTGACGAGATTAATACCTG (SEQ ID NO: 100) | | |
| Exon 5 | CTCTGTAACTGCTTATAATCCTG (SEQ ID NO: 69) | 55 | 235 |
| Exon 5 (rev) | CTAGGAAACCTGTACAACTCC (SEQ ID NO: 70) | | |
| Exon 6 | GGCTTATTGTGTGCTGATATC (SEQ ID NO: 71) | 55 | 289 |
| Exon 6 (rev) | AGAGATCCTTAAGTCGTCATG (SEQ ID NO: 72) | | |
| Exon 7 | CATGACGACTTAAGGATCTCTT (SEQ ID NO: 101) | 55 | 196 |
| Exon 7 (rev) | CTCAGTTTCCAGAGTACAAAC (SEQ ID NO: 102) | | |
| Exon 8 | CAGTTTCTGTGAGAGAGTACA (SEQ ID NO: 73) | 55 | 283 |
| Exon 8 (rev) | GGCTTACCTGCTCCTGTATTT (SEQ ID NO: 74) | | |
| Exon 9 | GTGAATTAAAGTCTTTCTGGCC (SEQ ID NO: 103) | 55 | 277 |
| Exon 9 (rev) | ATCTTAGAAAGCAGACAGGGC (SEQ ID NO: 104) | | |
| Exon 10 | GAGACATTTTATCCCCTTGTG (SEQ ID NO: 105) | 55 | 289 |
| Exon 10 (rev) | TCCATGCCTCCAGTCTAAAGT (SEQ ID NO: 106) | | |
| Exon 11 | GAGGAGGAATGGGCCTTTATT (SEQ ID NO: 75) | 55 | 244 |
| Exon 11 (rev) | AACCCACAGAATAGGGCAGGA (SEQ ID NO: 76) | | |
| Exon 12 | CACTTAAGTTGCACTGGGTA (SEQ ID NO: 107) | 55 | 273 |
| Exon 12 (rev) | CAACAGGAAGTTGGTCTCATC (SEQ ID NO: 108) | | |
| Exon 13 | TAAAAGGAAGAGCGGCTGTTT (SEQ ID NO: 109) | 55 | 378 |
| Exon 13 (rev) | TTAAACCTAACTGCCACCCTC (SEQ ID NO: 110) | | |
| Exon 14 | GGATACTGGCATTCTGTGTAAC (SEQ ID NO: 77) | 55 | 197 |
| Exon 14 (rev) | ATTTCCAGATAGTAAGCCCCA (SEQ ID NO: 78) | | |
| Exon 15 | AGCTTGGACGGAAGTCAGATC (SEQ ID NO: 79) | 55 | 413 |
| Exon 15 (rev) | TCTAGCCAAACCTCGGGTAAC (SEQ ID NO: 80) | | |
| Exon 16 | AATTGTAAACCTCTGCCC (SEQ ID NO: 81) | 55 | 394 |
| Exon 16 (rev) | ATTTCCAAGCTCATGCT (SEQ ID NO: 82) | | |
| Exon 17 | AGCATGAGCTTGGGAAAT (SEQ ID NO: 83) | 55 | 277 |
| Exon 17 (rev) | TGAAGACCTATCTTTGCC (SEQ ID NO: 84) | | |
| Exon 18 | GTTCACAGAGCTCCTCACACT (SEQ ID NO: 85) | 55 | 230 |
| Exon 18 (rev) | AGGCCACAGAGTCAACTATGG (SEQ ID NO: 86) | | |
| Exon 19 | AGGTCCTATCACCAAGGGTGT (SEQ ID NO: 87) | 55 | 250 |
| Exon 19 (rev) | GCTTAGTTACTTCTTCAAGGC (SEQ ID NO: 88) | | |
| Exon 20 | GTAGCTGTTCCCTTTCTCCTA (SEQ ID NO: 89) | 55 | 364 |
| Exon 20 (rev) | CCTCAACACTCATGAGAGTGA (SEQ ID NO: 90) | | |
| Exon 21 | TGGTTTAGCACACCTCTTCAC (SEQ ID NO: 91) | 55 | 325 |
| Exon 21 (rev) | GCTTAGCACAAACCCTGTTTC (SEQ ID NO: 92) | | |
| Exon 22 | CTGAGCTATGTGCATTTGCA (SEQ ID NO: 111) | 55 | 232 |
| Exon 22 (rev) | AAGGCTGCTGCTAAACAGAT (SEQ ID NO: 112) | | |

C. PCR Amplification

The sample DNA was amplified in a Perkin-Elmer Cetus thermocycler. The PCR was performed in a 100 μl reaction volume using 2.5 units of recombinant Taq DNA-polymerase and 40 ng of genomic DNA. The reaction mixture was prepared according to the recommendations given in the Gene Amp DNA Amplification kit (Perkin-Elmer Cetus). The reaction mixture consisted of 50 mM/l KCl, 10 mM/l Tris-HCl (pH 8.3), 1.5 mM MgCl, 200 μM each deoxynucleotide triphosphate and 1 μM of each primer. Thirty five (35) PCR cycles were carried out, with each cycle consisting of an initial denaturation step at 95° C. for one minute, one minute at the annealing temperature (55° C.), an extension step at 72° C. for one minute, and followed by a final incubation period at 72° C. for seven minutes. Suitable annealing temperatures are shown in Table 2 for each of the primers designed in accordance with this invention. Minor adjustments in the annealing temperatures may be made to accommodate other primers designed in accordance with this invention.

D. Amplification Products of PCR

The size of the amplification products produced by PCR are shown in Table 2 above. The lengths of the PCR products ranged from 196 bp to 413 bp.

E. Sequencing of PCR Products

Sequencing of the amplification products of pRb2/p 130 can be conducted according to the method set forth in Example 1C above. Sequencing can also be performed by the chain termination technique described by Sanger et al., *Proc. Nat'l. Acad. Sci., U.S.A.* 74:5463–5467 (1977) or Sambrook et al., *Molecular Cloning: A Laboratory Manual*, Second Edition, pp. 13.42–13.77, Cold Spring Harbor Laboratory Press, Cold Spring Harbor, N.Y. (1989) with appropriate primers based on the pRb2/p130 genomic sequence described herein.

EXAMPLE 4

Detecting Mutations By SSCP Analysis

A. General Methods

The SSCP analysis was performed according to the methods of Orita et al., *Genomics* 5:874–879 (1989) and Hogg et al., *Oncogene* 7:1445–1451 (1992), each of which is incorporated herein by reference. For the SSCP analysis, amplification of the individual exons was, in some experiments, performed as described in Example 3 with the exception that 1 μCi of [$^{32}$P]dCTP (3000 Ci mmol$^{-1}$) was added to the mixture in order to obtain a labeled product. A 10% aliquot of the PCR-amplified product was diluted with a mixture of 10–20 μl of 0.1% SDS and 10 mM EDTA. Following a 1:1 dilution with 95% formamide, 2mM EDTA, 0.05% bromophenol blue, and 0.05% xylene cyanol loading solution (United States Biochemicals, Ohio), the diluted sample was run on a 6% non-denaturing gel. The DNA was electrophoresed in TBE (0.09M Tris base, 0.09M boric acid and 2.5 mM EDTA) running buffer at constant wattage at room temperature. The gel was dried on filter paper and exposed to X-ray film for 12 to 72 hours without an intensifying screen.

Polymorphisms and mutations were detected by observing a shift in the electrophoretic mobility pattern of the denatured PCR-amplified product relative to a corresponding wild type sample or normal tissue sample from the same patient. Once a band shift was identified, the segment was sequenced to confirm the exact nature of the polymorphism or mutation.

B. Detection Of pRb2/p130 Gene Mutations In the CCRF-CEM Cell Line

DNA was extracted from the CCRF-CEM line (human lymphoblastoid cells), and amplified. For the amplification, 50 µl of the PCR reaction mix containing 4 ng of genomic DNA, 0.2 mM of each deoxynucleotide triphosphates, 2 U of Taq polymerase and 0.4 µM of each primer were used. Fifty-Five cycles of denaturation (95° C., 1 minute), annealing (55° C., 1 minute) and extension (72° C., 1 minute) were carried out in a thermal cycler. The SSCP analysis was performed using an MDE mutation detection kit (AT Biochem). The PCR products were heated to 95° C. for two minutes and placed directly on ice for several minutes. The samples were run through the MDE gel at 8 Watts constant power for eight hours at room temperature, in 0.6× TBE running buffer. The gel was stained for 15 minutes at room temperature in a 1 µg/ml ethidium bromide solution, made in 0.6× TBE buffer, and placed on a UV-transilluminator to visualize the bands. Exon 20 showed a different migration relative to the control, suggesting the presence of mutations.

The sequences of the PCR products were determined by automated DNA sequencing, using dideoxy-terminator reaction chemistry. A point mutation was identified: CCT to CGT at position 3029 of SEQ ID NO: 1, resulting in a proline to arginine substitution.

C. Detection of pRb2/p130 Gene Mutations in Other Cell Lines

Using the SSCP and DNA sequencing methods described above, mutations in the pRb2/p130 gene, including point mutations, insertions, and deletions in exons 19–22, were identified in the following human tumor cell lines:

Jurkat cell line (human leukemia, T-cell lymphoblast);

K562 cell line (human chronic myelogenous leukemia, erythroblastoid cells);

Molt-4 cell line (human T-cell leukemia, peripheral blood lymphoblast);

Daudi cell line (human thyroid lymphoma, lymphoblast B cell);

Cem cell line (lymphoblastoid cell line, T-lymphocytes);

Saos-2 cell line (human primary osteogenic sarcoma);

U2-Os cell line (human primary osteogenic sarcoma);

MG63 cell line (human osteosarcoma);

Hos cell line (human osteogenic sarcoma, TE85);

U1752 cell line (human lung tumor);

H69 cell line (human lung tumor);

H82 cell line (human lung tumor); and

Hone cell line (human nasopharyngeal carcinoma).

D. Detection of pRb2/p130 Gene Mutations in Primary Tumors

Using the SSCP and DNA sequencing methods described above, mutations in the pRb2/p130 gene were identified in the following primary human tumors:

13 NPC primary tumor (human nasopharyngeal carcinoma);

5 NPC primary tumor (human nasopharyngeal carcinoma);

EXAMPLE 5

Detecting Mutations By The PRINS Technique

The PRINS technique was performed according to the method of Cinti et al., *Nuc. Acids Res*. Vol. 21, No. 24:5799–5800 (1993) using human peripheral lymphocytes as the source of genomic DNA. The oligonucleotide primers were designed such that they included portions of the introns flanking exon 20. The sequences of the primers utilized to amplify exon 20 are listed in Table 2 above (SEQ ID NOS:89 and 90).

Human fixed metaphase chromosomes or interphase nuclei from PHA stimulated peripheral blood lymphocytes were spread onto glass slides and allowed to air dry for ten days. The DNA was dehydrated in an ethanol series (70%, 90%, and 100%) and then denatured by heating to 94° C. for 5 minutes. Using a reaction mixture containing 200 pmol of each oligonucleotide primer, 5 µl of 10×PCR Buffer II (AmpliTaq, Perkin-Elmer), 2 µl DIG DNA labeling mixture (1 mM dATP, 1 mM dCTP, 1 mM dGTP, 0.65 mM dTTP, 0.35 mM DIG-dUTP, Boehringer-Mannheim) and 2 Units of Taq I DNA polymerase (AmpliTaq, Perkin-Elmer), the samples were incubated for 10 minutes at 55° C. and for 30 minutes at 72° C. Suitable annealing temperatures for other primers designed in accordance with this invention are shown in Table 2. The samples were then washed two times in 2×SSC (pH 7.0) and in 4×SSC (pH 7.0) for 5 minutes at room temperature. The DNA samples were then placed in a solution of 4×SSC and 0.5% Bovine Serum Albumin (BSA) (pH 7.0), incubated at room temperature for 45 minutes with anti-Digoxigenin-FITC (Boehringer-Mannheim), and diluted 1:100 in 4×SSC and 0.5% BSA (pH 7.0). After washing the samples in 4×SSC and 0.05% Triton X-100, the samples were counterstained with 1 µg/ml Propidium Iodide (PI).

The slides were examined under a Confocal Laser Scanning Microscope (CLSM Sarastro, Molecular Dynamics). The FITC and PI signals were detected simultaneously, independently elaborated and the final projections were superimposed with a Silicon Graphic Computer Personal IRIS-4D/20 workstation.

Figure 4:
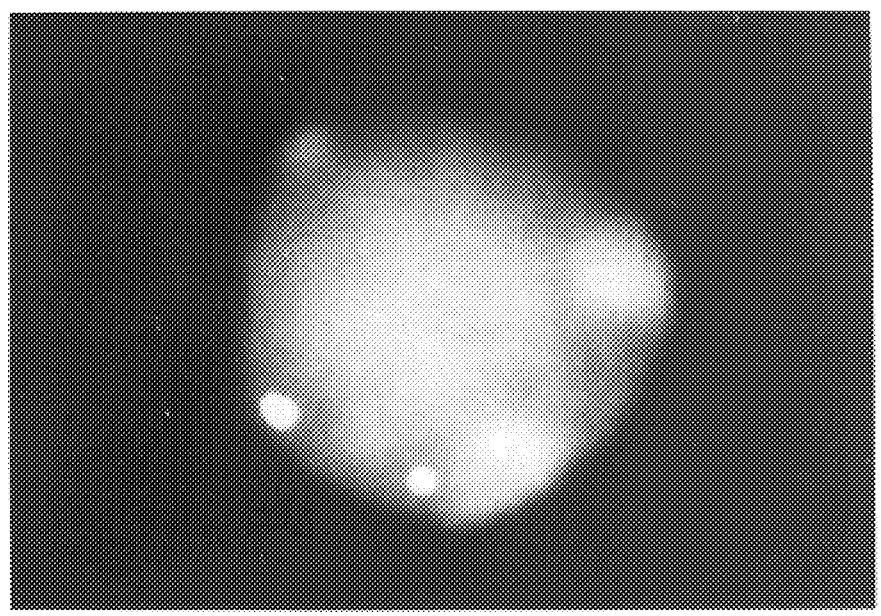
FIG. 4 illustrates two alleles containing exon 20 of the pRb2/p130 gene in the nucleus of a peripheral blood lymphocyte visualized through the use of the PRINS technique.

FIG. 4 shows the results of a PRINS reaction on normal human interphase nuclei. The bright spots correspond to a DNA segment containing exon 20 of pRb2/p130. This individual is homozygous for the presence of exon 20 of pRb2/p130. Had there been a mutation in exon 20 of this individual, either one or both of these areas would have been diminished in intensity or not visible in its entirety. To determine the exact nature of this mutation, the patient's pRb2/p130 DNA segment would be sequenced by methods known to those skilled in the art and compared to a wild type sample of pRb2/p130 DNA.

All the references discussed herein are incorporated by reference.

One skilled in the art will readily appreciate that the present invention is well adapted to carry out the ends and advantages mentioned, as well as those inherent therein. The nucleic acids, compositions, methods, procedures, and techniques described herein are presented as representative of the preferred embodiments, and are intended to be exemplary and not limitations on the scope of the invention. The present invention may be embodied in other specific forms without departing from the spirit or essential attributes thereof and, accordingly, reference should be made to the appended claims, rather than to the foregoing specification, as defining the scope of the invention.

I claim:

1. A DNA segment consisting of an intron of the human pRb2/p130 gene, or an at least 15 nucleotide segment of said intron.

2. The DNA segment according to claim 1 consisting of pRb2/p130 intron 1, or an at least 15 nucleotide segmeny of said intron.

3. The DNA segment according to claim 2 consisting of the nucleotide sequence set forth as SEQ ID NO:66, or an at least 15 nucleotide segment of said sequence.

4. The DNA segment according to claim 1 consisting of pRb2/p130 intron 2, or an at least 15 nucleotide segment of said intron.

5. The DNA segment according to claim 4 consisting of the nucleotide sequence set forth as SEQ ID NO:67. or an at least 15 nucleotide segment of said sequence.

6. The DNA segment according to claim, I consisting of pRb2/p130 intron 3, or an at least 15 nucleotide segment of said intron.

7. The DNA segment according to claim 6 consisting of the nucleotide sequence set forth as SEQ ID NO:48, or an at least 15 nucleotide segment of said segment.

8. The DNA segment according to claim 1 consisting of pRb2/p130 intron 4, or an at least 15 nucleotide segment of said intron.

9. The DNA segment according to claim 8 consisting of the nucleotide sequence set forth as SEQ ID NO;49, or an at least 15 nucleotide segment of said sequence.

10. The DNA segment according to claim 1 consisting of pRb2/p130 intron 5, or an at least 15 nucleotide segment of said intron.

11. The DNA segment according to claim 10 consisting of the nucleotide sequence set forth as SEQ ID NO:50, or an at least 15 nucleotide segment of said sequence.

12. The DNA segment according to claim 1 consisting of pRb2/p130 intron 6, or an at least 15 nucleotide segment of said intron.

13. The DNA segment according to claim 12 consisting of the nucleotide sequence set forth as SEQ ID NO:51, or an at least 15 nucleotide segment of said sequence.

14. The DNA segment according to claim 1 consisting of pRb2/p130 intron 7, or an at least 15 nucleotide segment of said intron.

15. The DNA segment according to claim 14 consisting of the nucleotide sequence set forth as SEQ ID NO:52. or an at least 15 nucleotide segment of said sequence.

16. The DNA segment according to claim 1 consisting of pRb2/p130 intron 8, or an at least 15 nucleotide segment of said intron.

17. The DNA segment according to claim 16 consisting of the nucleotide sequence set forth as SEQ ID NO:53, or an at least 15 nucleotide segment of said sequence.

18. The DNA segment according to claim 1 consisting of pRb2/p130 intron 9, or an at least 15 nucleotide segment of said intron.

19. The DNA segment according to claim 18 consisting of the nucleotide sequence set forth as SEQ ID NO:54, or an at least 15 nucleotide segment of said sequence.

20. The DNA segment according to claim 1 consisting of pRb2/p130 intron 10, or an at least 15 nucleotide segment of said intron.

21. The DNA segment according to claim 20 consisting of the nucleotide sequence set forth as SEQ ID NO:55, or an at least 15 nucleotide segment of said sequence.

22. The DNA segment according to claim 1 consisting of pRb2/p130 intron 11, or an at least 15 nucleotide segment of said intron.

23. The DNA segment according to claim 22 consisting of the nucleotide sequence set forth as SEQ ID NO:56, or an at least 15 nucleotide segment of said sequence.

24. The DNA segment according to claim 1 consisting of pRb2/p130 intron 12, or an at least 15 nucleotide segment of said intron.

25. The DNA segment according to claim 24 consisting of the nucleotide sequence set forth as SEQ ID NO:57, or an at least 15 nucleotide segment of said sequence.

26. The DNA segment according to claim 1 consisting of pRb2/p130 intron 13, or an at least 15 nucleotide segment of said intron.

27. The DNA segment according to claim 26 consisting of the nucleotide sequence set forth as SEQ ID NO:58, or an at least 15 nucleotide segment of said sequence.

28. The DNA segment according to claim 1 consisting of pRb2/p130 intron 14, or an at least 15 nucleotide segment of said intron.

29. The DNA segment according to claim 28 consisting of the nucleotide sequence set forth as SEQ ID NO:59, or an at least 15 nucleotide segment of said sequence.

30. The DNA segment according to claim 1 consisting of pRb2/p130 intron 15, or an at least 15 nucleotide segment of said intron.

31. The DNA segment according to claim 30 consisting of the nucleotide sequence set forth as SEQ ID NO:60, or an at least 15 nucleotide segment of said sequence.

32. The DNA segment according to claim 1 consisting of pRb2/p130 intron 16, or an at least 15 nucleotide segment of said intron.

33. The DNA segment according to claim 32 consisting of the nucleotide sequence set forth as SEQ ID NO:61, or an at least 15 nucleotide segment of said sequence.

34. The DNA segment according to claim 1 consisting of pRb2/p130 intron 17, or an at least 15 nucleotide segment of said intron.

35. The DNA segment according to claim 34 consisting of the nucleotide sequence set forth as SEQ ID NO:62. or an at least 15 nucleotide segment of said sequence.

36. The DNA segment according to claim 1 consisting of pRb2/p130 intron 18, or an at least 15 nucleotide segment of said intron.

37. The DNA segment according to claim 36 consisting of the nucleotide sequence set forth as SEQ ID NO:63, or an at least 15 nucleotide segment of said sequence.

38. The DNA segment according to claim 1 consisting of pRb2/p130 intron 19, or an at least 15 nucleotide segment of said intron.

39. The DNA segment according to claim 38 consisting of the nucleotide sequence set forth as SEQ ID NO:64, or an at least 15 nucleotide segment of said sequence.

40. The DNA segment according to claim 1 consisting of pRb2/p130 intron 20, or an at least 15 nucleotide segment of said intron.

41. The DNA segment according to claim 40 consisting of the nucleotide sequence set forth as SEQ ID NO:65, or an at least 15 nucleotide segment of said sequence.

42. The DNA segment according to claim 1 consisting of pRb2/p130 intron 21, or at least an 18 nucleotide segment of said intron.

43. The DNA segment according to claim 42 consisting of the nucleotide sequence set forth as SEQ ID NO:68. or in at least 15 nucleotide segment of said sequence.

44. An amplification primer of at least 15 nucleotides consisting of a DNA segment which is substantially complementary to a segment of a human pRb2/p130 intron exclusive of the splice signal dinucleotides of said intron.

45. The amplification primer according to claim 44 wherein the primer contains from 15 to 30 nucleotides.

46. The amplification primer according to claim 45 wherein the primer contains from 18 to 27 nucleotides.

47. The amplification primer according to claim 44 wherein the primer is substantially complementary to an intron wherein the nucleotide sequence of the intron is selected from the group consisting of SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, and SEQ ID NO:68.

48. THe amplification primer according to claim 44 wherein the nucleotide sequence of the primer is selected from the group consisting of SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:94, SEQ ID NO: 95, SEQ ID NO: , SEQ ID NO: 97, SEQ ID NO:98, SEQ ID NO:99, SEQ ID NO: 100, SEQ ID NO: 106, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO:110, and SEQ ID NO:111.

49. The method for identifying a polymorphism or a mutation in an exon of a human pRb2/p130 gene, which method comprises:
  (a) incubating, under amplification conditions, a sample of genomic DNA containing the exon with a primer pair comprising a first primer which hybridizes to a promoter region or to an intron upstream of said exon and a second primer which hybridizes to the 3'-noncoding region or to an intron downstream of said exon, wherein at least one primer of the primer pair hybridizes to an intron, said treatment producing an amplification product containing said exon;
  (b) determining the nucleotide sequence of said amplification product to provide the nucleotide sequence of said exon; and
  (c) comparing the sequence of said exon obtained in step (b) to the sequence of a corresponding wild type exon, wherein a polymorphism or mutation is identified as a difference in sequence.

50. The method according to claim 49 wherein each primer of said primer pair is substantially complementary to the 3'-noncoding region, to the promoter region given as SEQ ID NO:3, or to an intron consisting of a nucleotide sequence selected from the group consisting of SEQ ID NO:48, SEQ ID NO:49, SEQ ID NO:50, SEQ ID NO:51, SEQ ID NO.:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, and SEQ ID NO:68.

51. The method according to claim 49 wherein each primer of said primer pair consists of a nucleotide sequence selected from the group consisting of SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO: 100, SEQ ID NO: 101, SEQ ID NO: 102, SEQ ID NO: 103, SEQ ID NO: 104, SEQ ID NO:105, SEQ ID NO: 106, SEQ ID NO:107, SEQ ID NO: 108, SEQ ID NO:109, SEQ ID NO:110, SEQ ID NO:111, and SEQ ID NO:112.

52. The method for detecting polymorphisms and mutations in an exon of a human pRb2/p130 gene, which method comprises:
  (a) forming a polymerase chain reaction admixture by combining in a polymerase chain reaction buffer, a sample of genomic DNA containing said exon, a primer pair comprising a first primer which hybridizes to a promoter region or to an intron upstream of said exon and a second primer which hybridizes to the 3'-noncoding region or to an intron downstream of said exon, wherein at least one primer of the primer pair hybridizes to an intron a mixture of one or more deoxynucleotide triphosphates, and a compound capable of radioactively labeling said primer pair, and a DNA polymerase;
  (b) subjecting said admixture to a plurality of polymerase chain reaction thermocycles to produce a pRb2/p130 amplification product;
  (c) denaturing said pRb2/p130 amplification product;
  (d) electrophoretically separating said denatured pRb2/p130 amplification product;
  (e) exposing the electrophoretically separated product of step (d) to a film to produce a photographic image; and
  (e) comparing the mobility of the bands in said photographic image of said pRb2/p130 amplification product to a electrophoretically separated amplification product for a corresponding wild type exon, wherein polymorphisms and mutations are detected as differences in mobility.

53. The method according to claim 52 wherein each primer of said primer pair is substantially complementary to the 3'-noncoding region, the promoter region given as SEQ ID NO:3, or an intron consisting of a nucleotide sequence selected from the group consisting of SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61. SEQ ID NO:62, SEQ ID NO:63, SEQ ID NO:64, SEQ ID NO:65, SEQ ID NO:66, SEQ ID NO:67, and SEQ ID NO:68.

54. The method according to claim 52 wherein each primer of said primer pair consists of a nucleotide sequence selected from the group consisting of SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO: 100, SEQ ID NO:101, SEQ ID NO:102, SEQ ID NO: 103, SEQ ID NO:104, SEQ ID NO:105, SEQ ID NO: 106, SEQ ID NO: 107, SEQ ID NO:108, SEQ ID NO: 109, SEQ ID NO:110, SEQ ID NO:111, and SEQ ID NO:112.

55. The method for detecting mutations in a human chromosomal sample containing an exon of a human pRb2/p130 gene, which method comprises:

(a) denaturing the DNA in a sample of human fixed dehydrated metaphase chromosomes or interphase nuclei;

(b) forming an admixture by combining in a buffer, the metaphase chromosomes or nuclei, a primer pair comprising a first primer which hybridizes to the promoter region or to an intron upstream of said exon and a second primer which hybridizes to the 3'-noncoding region or to an intron downstream of said exon, wherein at least one primer of the primer pair hybridizes to an intron, a mixture of one or more deoxynucleotide triphosphates including at least one deoxynucleotide triphosphate that is labeled, and a DNA polymerase, (c) subjecting said admixture to a temperature and time sufficient to produce a pRb2/p130 amplification product, whereby the amplification product is labeled;

(d) mixing the labeled amplification product with a fluorochrome conjugate which specifically binds to the labeled amplification product;

(e) visualizing signals produced by the fluorochrome conjugate bound to the labeled amplification product; and (f) comparing the number and intensity of the signals obtained in step (e) to the signals for a corresponding wild type exon, wherein mutations are detected as differences in number or intensity.

56. The method according to claim 55 wherein each primer of said primer pair is substantially complementary to the 3'-noncoding region, a promoter region given as SEQ ID NO:3, or an intron consisting of a nucleotide sequence selected from the group consisting of SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, and SEQ ID NO:68.

57. The method according to claim 55 wherein each primer of said primer pair consists of a nucleotide sequence selected from the group consisting of SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO: 100, SEQ ID NO: 101, SEQ ID NO:102, SEQ ID NO:103, SEQ ID NO: 104, SEQ ID NO:105, SEQ ID NO: 106, SEQ ID NO: 107, SEQ ID NO:108, SEQ ID NO:109, SEQ ID NO:110, SEQ ID NO:111, and SEQ ID NO:112.

58. A kit for the detection of mutations in an exon of a human pRb2/p130 gene comprising:

a carrier for receiving one or more containers;

a first container comprising one or more subcontainers for holding a glass slide for drying, dehydrating and denaturing a sample of human DNA;

a second container comprising a reaction mixture comprised of a buffer, a labeling mixture, the primer according to claim 44, and a polymerase for amplifying a sample of human DNA;

a third container comprising a fluorochrome conjugate specific to said labeling mixture; and a fourth container comprising a staining compound.

* * * * *

SEQUENCE LISTING ( 1 ) GENERAL INFORMATION:

( i i i ) NUMBER OF SEQUENCES: 115

( 2 ) INFORMATION FOR SEQ ID NO:1:

( i ) SEQUENCE CHARACTERISTICS:
( A ) LENGTH: 4853 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 70..3489

( x i ) SEQUENCE DESCRIPTION: SEQ ID NO:1:

```
TTCGCCGTTT  GAATTGCTGC  GGGCCCGGGC  CCTCACCTCA  CCTGAGGTCC  GGCCGCCAG           60

GGGTGCGCT ATG CCG TCG GGA GGT GAC CAG TCG CCA CCG CCC CCG CCT                 108
          Met Pro Ser Gly Gly Asp Gln Ser Pro Pro Pro Pro Pro
           1               5                    10

CCC CCT CCG GCG GCG GCA GCC TCG GAT GAG GAG GAG GAG GAC GAC GGC               156
Pro Pro Pro Ala Ala Ala Ala Ser Asp Glu Glu Glu Glu Asp Asp Gly
        15              20                  25

GAG GCG GAA GAC GCC GCG CCG TCT GCC GAG TCG CCC ACC CCT CAG ATC               204
Glu Ala Glu Asp Ala Ala Pro Ser Ala Glu Ser Pro Thr Pro Gln Ile
 30              35                  40                  45

CAG CAG CGG TTC GAC GAG CTG TGC AGC CGC CTC AAC ATG GAC GAG GCG               252
Gln Gln Arg Phe Asp Glu Leu Cys Ser Arg Leu Asn Met Asp Glu Ala
                50                  55                  60

GCG CGG CCC GAG GCC TGG GAC AGC TAC CGC AGC ATG AGC GAA AGC TAC               300
Ala Arg Pro Glu Ala Trp Asp Ser Tyr Arg Ser Met Ser Glu Ser Tyr
             65                  70                  75

ACG CTG GAG GGA AAT GAT CTT CAT TGG TTA GCA TGT GCC TTA TAT GTG               348
Thr Leu Glu Gly Asn Asp Leu His Trp Leu Ala Cys Ala Leu Tyr Val
         80                  85                  90

GCT TGC AGA AAA TCT GTT CCA ACT GTA AGC AAA GGG ACA GTG GAA GGA               396
Ala Cys Arg Lys Ser Val Pro Thr Val Ser Lys Gly Thr Val Glu Gly
     95                 100                 105

AAC TAT GTA TCT TTA ACT AGA ATC CTG AAA TGT TCA GAG CAG AGC TTA               444
Asn Tyr Val Ser Leu Thr Arg Ile Leu Lys Cys Ser Glu Gln Ser Leu
110                 115                 120                 125

ATC GAA TTT TTT AAT AAG ATG AAG AAG TGG GAA GAC ATG GCA AAT CTA               492
Ile Glu Phe Phe Asn Lys Met Lys Lys Trp Glu Asp Met Ala Asn Leu
                130                 135                 140

CCC CCA CAT TTC AGA GAA CGT ACT GAG AGA TTA GAA AGA AAC TTC ACT               540
Pro Pro His Phe Arg Glu Arg Thr Glu Arg Leu Glu Arg Asn Phe Thr
            145                 150                 155

GTT TCT GCT GTA ATT TTT AAG AAA TAT GAA CCC ATT TTT CAG GAC ATC               588
Val Ser Ala Val Ile Phe Lys Lys Tyr Glu Pro Ile Phe Gln Asp Ile
        160                 165                 170

TTT AAA TAC CCT CAA GAG GAG CAA CCT CGT CAG CAG CGA GGA AGG AAA               636
```

-continued

| | | | | | | | | | | | | | | | |
|---|---|---|---|---|---|---|---|---|---|---|---|---|---|---|---|
| Phe | Lys | Tyr | Pro | Gln | Glu | Glu | Gln | Pro | Arg | Gln | Gln | Arg | Gly | Arg | Lys |
| | 175 | | | | 180 | | | | | 185 | | | | | |

| CAG | CGG | CGA | CAG | CCC | TGT | ACT | GTG | TCT | GAA | ATT | TTC | CAT | TTT | TGT | TGG | 684 |
|---|---|---|---|---|---|---|---|---|---|---|---|---|---|---|---|---|
| Gln | Arg | Arg | Gln | Pro | Cys | Thr | Val | Ser | Glu | Ile | Phe | His | Phe | Cys | Trp | |
| 190 | | | | | 195 | | | | | 200 | | | | | 205 | |

| GTG | CTT | TTT | ATA | TAT | GCA | AAA | GGT | AAT | TTC | CCC | ATG | ATT | AGT | GAT | GAT | 732 |
|---|---|---|---|---|---|---|---|---|---|---|---|---|---|---|---|---|
| Val | Leu | Phe | Ile | Tyr | Ala | Lys | Gly | Asn | Phe | Pro | Met | Ile | Ser | Asp | Asp | |
| | | | | 210 | | | | | 215 | | | | | 220 | | |

| TTG | GTC | AAT | TCT | TAT | CAC | CTG | CTG | CTG | TGT | GCT | TTG | GAC | TTA | GTT | TAT | 780 |
|---|---|---|---|---|---|---|---|---|---|---|---|---|---|---|---|---|
| Leu | Val | Asn | Ser | Tyr | His | Leu | Leu | Leu | Cys | Ala | Leu | Asp | Leu | Val | Tyr | |
| | | | 225 | | | | | 230 | | | | | 235 | | | |

| GGA | AAT | GCA | CTT | CAG | TGT | TCT | AAT | CGT | AAA | GAA | CTT | GTG | AAC | CCT | AAT | 828 |
|---|---|---|---|---|---|---|---|---|---|---|---|---|---|---|---|---|
| Gly | Asn | Ala | Leu | Gln | Cys | Ser | Asn | Arg | Lys | Glu | Leu | Val | Asn | Pro | Asn | |
| | | 240 | | | | | 245 | | | | | 250 | | | | |

| TTT | AAA | GGC | TTA | TCT | GAA | GAT | TTT | CAT | GCT | AAA | GAT | TCT | AAA | CCT | TCC | 876 |
|---|---|---|---|---|---|---|---|---|---|---|---|---|---|---|---|---|
| Phe | Lys | Gly | Leu | Ser | Glu | Asp | Phe | His | Ala | Lys | Asp | Ser | Lys | Pro | Ser | |
| | 255 | | | | | 260 | | | | | 265 | | | | | |

| TCT | GAC | CCC | CCT | TGT | ATC | ATT | GAG | AAA | CTG | TGT | TCC | TTA | CAT | GAT | GGC | 924 |
|---|---|---|---|---|---|---|---|---|---|---|---|---|---|---|---|---|
| Ser | Asp | Pro | Pro | Cys | Ile | Ile | Glu | Lys | Leu | Cys | Ser | Leu | His | Asp | Gly | |
| 270 | | | | | 275 | | | | | 280 | | | | | 285 | |

| CTA | GTT | TTG | GAA | GCA | AAG | GGG | ATA | AAG | GAA | CAT | TTC | TGG | AAA | CCC | TAT | 972 |
|---|---|---|---|---|---|---|---|---|---|---|---|---|---|---|---|---|
| Leu | Val | Leu | Glu | Ala | Lys | Gly | Ile | Lys | Glu | His | Phe | Trp | Lys | Pro | Tyr | |
| | | | | 290 | | | | | 295 | | | | | | 300 | |

| ATT | AGG | AAA | CTT | TAT | GAA | AAA | AAG | CTC | CTT | AAG | GGA | AAA | GAA | GAA | AAT | 1020 |
|---|---|---|---|---|---|---|---|---|---|---|---|---|---|---|---|---|
| Ile | Arg | Lys | Leu | Tyr | Glu | Lys | Lys | Leu | Leu | Lys | Gly | Lys | Glu | Glu | Asn | |
| | | | 305 | | | | | 310 | | | | | 315 | | | |

| CTC | ACT | GGG | TTT | CTA | GAA | CCT | GGG | AAC | TTT | GGA | GAG | AGT | TTT | AAA | GCC | 1068 |
|---|---|---|---|---|---|---|---|---|---|---|---|---|---|---|---|---|
| Leu | Thr | Gly | Phe | Leu | Glu | Pro | Gly | Asn | Phe | Gly | Glu | Ser | Phe | Lys | Ala | |
| | | 320 | | | | | 325 | | | | | 330 | | | | |

| ATC | AAT | AAG | GCC | TAT | GAG | GAG | TAT | GTT | TTA | TCT | GTT | GGG | AAT | TTA | GAT | 1116 |
|---|---|---|---|---|---|---|---|---|---|---|---|---|---|---|---|---|
| Ile | Asn | Lys | Ala | Tyr | Glu | Glu | Tyr | Val | Leu | Ser | Val | Gly | Asn | Leu | Asp | |
| | 335 | | | | | 340 | | | | | 345 | | | | | |

| GAG | CGG | ATA | TTT | CTT | GGA | GAG | GAT | GCT | GAG | GAG | GAA | ATT | GGG | ACT | CTC | 1164 |
|---|---|---|---|---|---|---|---|---|---|---|---|---|---|---|---|---|
| Glu | Arg | Ile | Phe | Leu | Gly | Glu | Asp | Ala | Glu | Glu | Glu | Ile | Gly | Thr | Leu | |
| 350 | | | | | 355 | | | | | 360 | | | | | 365 | |

| TCA | AGG | TGT | CTG | AAC | GCT | GGT | TCA | GGA | ACA | GAG | ACT | GCT | GAA | AGG | GTG | 1212 |
|---|---|---|---|---|---|---|---|---|---|---|---|---|---|---|---|---|
| Ser | Arg | Cys | Leu | Asn | Ala | Gly | Ser | Gly | Thr | Glu | Thr | Ala | Glu | Arg | Val | |
| | | | | 370 | | | | | 375 | | | | | 380 | | |

| CAG | ATG | AAA | AAC | ATC | TTA | CAG | CAG | CAT | TTT | GAC | AAG | TCC | AAA | GCA | CTT | 1260 |
|---|---|---|---|---|---|---|---|---|---|---|---|---|---|---|---|---|
| Gln | Met | Lys | Asn | Ile | Leu | Gln | Gln | His | Phe | Asp | Lys | Ser | Lys | Ala | Leu | |
| | | | 385 | | | | | 390 | | | | | 395 | | | |

| AGA | ATC | TCC | ACA | CCA | CTA | ACT | GGT | GTT | AGG | TAC | ATT | AAG | GAG | AAT | AGC | 1308 |
|---|---|---|---|---|---|---|---|---|---|---|---|---|---|---|---|---|
| Arg | Ile | Ser | Thr | Pro | Leu | Thr | Gly | Val | Arg | Tyr | Ile | Lys | Glu | Asn | Ser | |
| | | 400 | | | | | 405 | | | | | 410 | | | | |

| CCT | TGT | GTG | ACT | CCA | GTT | TCT | ACA | GCT | ACG | CAT | AGC | TTG | AGT | CGT | CTT | 1356 |
|---|---|---|---|---|---|---|---|---|---|---|---|---|---|---|---|---|
| Pro | Cys | Val | Thr | Pro | Val | Ser | Thr | Ala | Thr | His | Ser | Leu | Ser | Arg | Leu | |
| | 415 | | | | | 420 | | | | | 425 | | | | | |

| CAC | ACC | ATG | CTG | ACA | GGC | CTC | AGG | AAT | GCA | CCA | AGT | GAG | AAA | CTG | GAA | 1404 |
|---|---|---|---|---|---|---|---|---|---|---|---|---|---|---|---|---|
| His | Thr | Met | Leu | Thr | Gly | Leu | Arg | Asn | Ala | Pro | Ser | Glu | Lys | Leu | Glu | |
| 430 | | | | | 435 | | | | | 440 | | | | | 445 | |

| CAG | ATT | CTC | AGG | ACA | TGT | TCC | AGA | GAT | CCA | ACC | CAG | GCT | ATT | GCT | AAC | 1452 |
|---|---|---|---|---|---|---|---|---|---|---|---|---|---|---|---|---|
| Gln | Ile | Leu | Arg | Thr | Cys | Ser | Arg | Asp | Pro | Thr | Gln | Ala | Ile | Ala | Asn | |
| | | | | 450 | | | | | 455 | | | | | 460 | | |

| AGA | CTG | AAA | GAA | ATG | TTT | GAA | ATA | TAT | TCT | CAG | CAT | TTC | CAG | CCA | GAC | 1500 |
|---|---|---|---|---|---|---|---|---|---|---|---|---|---|---|---|---|
| Arg | Leu | Lys | Glu | Met | Phe | Glu | Ile | Tyr | Ser | Gln | His | Phe | Gln | Pro | Asp | |
| | | | 465 | | | | | 470 | | | | | 475 | | | |

| GAG | GAT | TTC | AGT | AAT | TGT | GCT | AAA | GAA | ATT | GCC | AGC | AAA | CAT | TTT | CGT | 1548 |
|---|---|---|---|---|---|---|---|---|---|---|---|---|---|---|---|---|
| Glu | Asp | Phe | Ser | Asn | Cys | Ala | Lys | Glu | Ile | Ala | Ser | Lys | His | Phe | Arg | |
| | | 480 | | | | | 485 | | | | | 490 | | | | |

| TTT | GCG | GAG | ATG | CTT | TAC | TAT | AAA | GTA | TTA | GAA | TCT | GTT | ATT | GAG | CAG | 1596 |

|     |     |     |     |     |     |     |     |     |     |     |     |     |     |     |     |
|-----|-----|-----|-----|-----|-----|-----|-----|-----|-----|-----|-----|-----|-----|-----|-----|
| Phe | Ala | Glu | Met | Leu | Tyr | Tyr | Lys | Val | Leu | Glu | Ser | Val | Ile | Glu | Gln |
|     | 495 |     |     |     | 500 |     |     |     |     | 505 |     |     |     |     |     |

| GAA | CAA | AAA | AGA | CTA | GGA | GAC | ATG | GAT | TTA | TCT | GGT | ATT | CTG | GAA | CAA | 1644 |
|-----|-----|-----|-----|-----|-----|-----|-----|-----|-----|-----|-----|-----|-----|-----|-----|------|
| Glu | Gln | Lys | Arg | Leu | Gly | Asp | Met | Asp | Leu | Ser | Gly | Ile | Leu | Glu | Gln |      |
| 510 |     |     |     |     | 515 |     |     |     | 520 |     |     |     |     |     | 525 |      |

| GAT | GCA | TTC | CAC | AGA | TCT | CTC | TTG | GCC | TGC | TGC | CTT | GAG | GTC | GTC | ACT | 1692 |
|-----|-----|-----|-----|-----|-----|-----|-----|-----|-----|-----|-----|-----|-----|-----|-----|------|
| Asp | Ala | Phe | His | Arg | Ser | Leu | Leu | Ala | Cys | Cys | Leu | Glu | Val | Val | Thr |      |
|     |     |     |     | 530 |     |     |     |     | 535 |     |     |     |     | 540 |     |      |

| TTT | TCT | TAT | AAG | CCT | CCT | GGG | AAT | TTT | CCA | TTT | ATT | ACT | GAA | ATA | TTT | 1740 |
|-----|-----|-----|-----|-----|-----|-----|-----|-----|-----|-----|-----|-----|-----|-----|-----|------|
| Phe | Ser | Tyr | Lys | Pro | Pro | Gly | Asn | Phe | Pro | Phe | Ile | Thr | Glu | Ile | Phe |      |
|     |     |     | 545 |     |     |     |     |     | 550 |     |     |     | 555 |     |     |      |

| GAT | GTG | CCT | CTT | TAT | CAT | TTT | TAT | AAG | GTG | ATA | GAA | GTA | TTC | ATT | AGA | 1788 |
|-----|-----|-----|-----|-----|-----|-----|-----|-----|-----|-----|-----|-----|-----|-----|-----|------|
| Asp | Val | Pro | Leu | Tyr | His | Phe | Tyr | Lys | Val | Ile | Glu | Val | Phe | Ile | Arg |      |
|     |     | 560 |     |     |     |     | 565 |     |     |     |     | 570 |     |     |     |      |

| GCA | GAA | GAT | GGC | CTT | TGT | AGA | GAG | GTG | GTA | AAA | CAC | CTT | AAT | CAG | ATT | 1836 |
|-----|-----|-----|-----|-----|-----|-----|-----|-----|-----|-----|-----|-----|-----|-----|-----|------|
| Ala | Glu | Asp | Gly | Leu | Cys | Arg | Glu | Val | Val | Lys | His | Leu | Asn | Gln | Ile |      |
|     | 575 |     |     |     |     | 580 |     |     |     |     | 585 |     |     |     |     |      |

| GAA | GAA | CAG | ATC | TTA | GAT | CAT | TTG | GCA | TGG | AAA | CCA | GAG | TCT | CCA | CTC | 1884 |
|-----|-----|-----|-----|-----|-----|-----|-----|-----|-----|-----|-----|-----|-----|-----|-----|------|
| Glu | Glu | Gln | Ile | Leu | Asp | His | Leu | Ala | Trp | Lys | Pro | Glu | Ser | Pro | Leu |      |
| 590 |     |     |     |     | 595 |     |     |     | 600 |     |     |     |     |     | 605 |      |

| TGG | GAA | AAA | ATT | AGA | GAC | AAT | GAA | AAC | AGA | GTT | CCT | ACA | TGT | GAA | GAG | 1932 |
|-----|-----|-----|-----|-----|-----|-----|-----|-----|-----|-----|-----|-----|-----|-----|-----|------|
| Trp | Glu | Lys | Ile | Arg | Asp | Asn | Glu | Asn | Arg | Val | Pro | Thr | Cys | Glu | Glu |      |
|     |     |     |     | 610 |     |     |     |     | 615 |     |     |     |     | 620 |     |      |

| GTC | ATG | CCA | CCT | CAG | AAC | CTG | GAA | AGG | GCA | GAT | GAA | ATT | TGC | ATT | GCT | 1980 |
|-----|-----|-----|-----|-----|-----|-----|-----|-----|-----|-----|-----|-----|-----|-----|-----|------|
| Val | Met | Pro | Pro | Gln | Asn | Leu | Glu | Arg | Ala | Asp | Glu | Ile | Cys | Ile | Ala |      |
|     |     |     | 625 |     |     |     |     | 630 |     |     |     |     | 635 |     |     |      |

| GGC | TCC | CCT | TTG | ACT | CCC | AGA | AGG | GTG | ACT | GAA | GTT | CGT | GCT | GAT | ACT | 2028 |
|-----|-----|-----|-----|-----|-----|-----|-----|-----|-----|-----|-----|-----|-----|-----|-----|------|
| Gly | Ser | Pro | Leu | Thr | Pro | Arg | Arg | Val | Thr | Glu | Val | Arg | Ala | Asp | Thr |      |
|     |     | 640 |     |     |     |     | 645 |     |     |     |     | 650 |     |     |     |      |

| GGA | GGA | CTT | GGA | AGG | AGC | ATA | ACA | TCT | CCA | ACC | ACA | TTA | TAC | GAT | AGG | 2076 |
|-----|-----|-----|-----|-----|-----|-----|-----|-----|-----|-----|-----|-----|-----|-----|-----|------|
| Gly | Gly | Leu | Gly | Arg | Ser | Ile | Thr | Ser | Pro | Thr | Thr | Leu | Tyr | Asp | Arg |      |
| 655 |     |     |     |     |     | 660 |     |     |     |     | 665 |     |     |     |     |      |

| TAC | AGC | TCC | CCA | CCA | GCC | AGC | ACT | ACC | AGA | AGG | CGG | CTA | TTT | GTT | GAG | 2124 |
|-----|-----|-----|-----|-----|-----|-----|-----|-----|-----|-----|-----|-----|-----|-----|-----|------|
| Tyr | Ser | Ser | Pro | Pro | Ala | Ser | Thr | Thr | Arg | Arg | Arg | Leu | Phe | Val | Glu |      |
| 670 |     |     |     |     | 675 |     |     |     |     | 680 |     |     |     |     | 685 |      |

| AAT | GAT | AGC | CCC | TCT | GAT | GGA | GGG | ACG | CCT | GGG | CGC | ATG | CCC | CCA | CAG | 2172 |
|-----|-----|-----|-----|-----|-----|-----|-----|-----|-----|-----|-----|-----|-----|-----|-----|------|
| Asn | Asp | Ser | Pro | Ser | Asp | Gly | Gly | Thr | Pro | Gly | Arg | Met | Pro | Pro | Gln |      |
|     |     |     |     | 690 |     |     |     |     | 695 |     |     |     |     | 700 |     |      |

| CCC | CTA | GTC | AAT | GCT | GTC | CCT | GTG | CAG | AAT | GTA | TCT | GGG | GAG | ACT | GTT | 2220 |
|-----|-----|-----|-----|-----|-----|-----|-----|-----|-----|-----|-----|-----|-----|-----|-----|------|
| Pro | Leu | Val | Asn | Ala | Val | Pro | Val | Gln | Asn | Val | Ser | Gly | Glu | Thr | Val |      |
|     |     |     | 705 |     |     |     |     | 710 |     |     |     |     | 715 |     |     |      |

| TCT | GTC | ACA | CCA | GTT | CCT | GGA | CAG | ACT | TTG | GTC | ACC | ATG | GCA | ACC | GCC | 2268 |
|-----|-----|-----|-----|-----|-----|-----|-----|-----|-----|-----|-----|-----|-----|-----|-----|------|
| Ser | Val | Thr | Pro | Val | Pro | Gly | Gln | Thr | Leu | Val | Thr | Met | Ala | Thr | Ala |      |
|     |     | 720 |     |     |     |     | 725 |     |     |     |     | 730 |     |     |     |      |

| ACT | GTC | ACA | GCC | AAC | AAT | GGG | CAA | ACG | GTA | ACC | ATT | CCT | GTG | CAA | GGT | 2316 |
|-----|-----|-----|-----|-----|-----|-----|-----|-----|-----|-----|-----|-----|-----|-----|-----|------|
| Thr | Val | Thr | Ala | Asn | Asn | Gly | Gln | Thr | Val | Thr | Ile | Pro | Val | Gln | Gly |      |
|     |     |     | 735 |     |     |     |     | 740 |     |     |     |     | 745 |     |     |      |

| ATT | GCC | AAT | GAA | AAT | GGA | GGG | ATA | ACA | TTC | TTC | CCT | GTC | CAA | GTC | AAT | 2364 |
|-----|-----|-----|-----|-----|-----|-----|-----|-----|-----|-----|-----|-----|-----|-----|-----|------|
| Ile | Ala | Asn | Glu | Asn | Gly | Gly | Ile | Thr | Phe | Phe | Pro | Val | Gln | Val | Asn |      |
| 750 |     |     |     |     | 755 |     |     |     |     | 760 |     |     |     |     | 765 |      |

| GTT | GGG | GGG | CAG | GCA | CAA | GCT | GTG | ACA | GGC | TCC | ATC | CAG | CCC | CTC | AGT | 2412 |
|-----|-----|-----|-----|-----|-----|-----|-----|-----|-----|-----|-----|-----|-----|-----|-----|------|
| Val | Gly | Gly | Gln | Ala | Gln | Ala | Val | Thr | Gly | Ser | Ile | Gln | Pro | Leu | Ser |      |
|     |     |     |     | 770 |     |     |     |     | 775 |     |     |     |     | 780 |     |      |

| GCT | CAG | GCC | CTG | GCT | GGA | AGT | CTG | AGC | TCT | CAA | CAG | GTG | ACA | GGA | ACA | 2460 |
|-----|-----|-----|-----|-----|-----|-----|-----|-----|-----|-----|-----|-----|-----|-----|-----|------|
| Ala | Gln | Ala | Leu | Ala | Gly | Ser | Leu | Ser | Ser | Gln | Gln | Val | Thr | Gly | Thr |      |
|     |     |     |     | 785 |     |     |     |     | 790 |     |     |     |     | 795 |     |      |

| ACT | TTG | CAA | GTC | CCT | GGT | CAA | GTG | GCC | ATT | CAA | CAG | ATT | TCC | CCA | GGT | 2508 |
|-----|-----|-----|-----|-----|-----|-----|-----|-----|-----|-----|-----|-----|-----|-----|-----|------|
| Thr | Leu | Gln | Val | Pro | Gly | Gln | Val | Ala | Ile | Gln | Gln | Ile | Ser | Pro | Gly |      |
|     |     | 800 |     |     |     |     | 805 |     |     |     |     | 810 |     |     |     |      |

| GGC | CAA | CAG | CAG | AAG | CAA | GGC | CAG | TCT | GTA | ACC | AGC | AGT | AGT | AAT | AGA | 2556 |
|-----|-----|-----|-----|-----|-----|-----|-----|-----|-----|-----|-----|-----|-----|-----|-----|------|

| | | | | | | | | | | | | | | | |
|---|---|---|---|---|---|---|---|---|---|---|---|---|---|---|---|
| Gly | Gln | Gln | Gln | Lys | Gln | Gly | Gln | Ser | Val | Thr | Ser | Ser | Ser | Asn | Arg |
| | 815 | | | | 820 | | | | | 825 | | | | | |

| CCC | AGG | AAG | ACC | AGC | TCT | TTA | TCG | CTT | TTC | TTT | AGA | AAG | GTA | TAC | CAT | 2604 |
|---|---|---|---|---|---|---|---|---|---|---|---|---|---|---|---|---|
| Pro | Arg | Lys | Thr | Ser | Ser | Leu | Ser | Leu | Phe | Phe | Arg | Lys | Val | Tyr | His | |
| 830 | | | | | 835 | | | | 840 | | | | | | 845 | |

| TTA | GCA | GCT | GTC | CGC | CTT | CGG | GAT | CTC | TGT | GCC | AAA | CTA | GAT | ATT | TCA | 2652 |
|---|---|---|---|---|---|---|---|---|---|---|---|---|---|---|---|---|
| Leu | Ala | Ala | Val | Arg | Leu | Arg | Asp | Leu | Cys | Ala | Lys | Leu | Asp | Ile | Ser | |
| | | | | 850 | | | | | 855 | | | | | 860 | | |

| GAT | GAA | TTG | AGG | AAA | AAA | ATC | TGG | ACC | TGC | TTT | GAA | TTC | TCC | ATA | ATT | 2700 |
|---|---|---|---|---|---|---|---|---|---|---|---|---|---|---|---|---|
| Asp | Glu | Leu | Arg | Lys | Lys | Ile | Trp | Thr | Cys | Phe | Glu | Phe | Ser | Ile | Ile | |
| | | | 865 | | | | | 870 | | | | | 875 | | | |

| CAG | TGT | CCT | GAA | CTT | ATG | ATG | GAC | AGA | CAT | CTG | GAC | CAG | TTA | TTA | ATG | 2748 |
|---|---|---|---|---|---|---|---|---|---|---|---|---|---|---|---|---|
| Gln | Cys | Pro | Glu | Leu | Met | Met | Asp | Arg | His | Leu | Asp | Gln | Leu | Leu | Met | |
| | | 880 | | | | | 885 | | | | | 890 | | | | |

| TGT | GCC | ATT | TAT | GTG | ATG | GCA | AAG | GTC | ACA | AAA | GAA | GAT | AAG | TCC | TTC | 2796 |
|---|---|---|---|---|---|---|---|---|---|---|---|---|---|---|---|---|
| Cys | Ala | Ile | Tyr | Val | Met | Ala | Lys | Val | Thr | Lys | Glu | Asp | Lys | Ser | Phe | |
| | 895 | | | | | 900 | | | | | 905 | | | | | |

| CAG | AAC | ATT | ATG | CGT | TGT | TAT | AGG | ACT | CAG | CCG | CAG | GCC | CGG | AGC | CAG | 2844 |
|---|---|---|---|---|---|---|---|---|---|---|---|---|---|---|---|---|
| Gln | Asn | Ile | Met | Arg | Cys | Tyr | Arg | Thr | Gln | Pro | Gln | Ala | Arg | Ser | Gln | |
| 910 | | | | | 915 | | | | | 920 | | | | | 925 | |

| GTG | TAT | AGA | AGT | GTT | TTG | ATA | AAA | GGG | AAA | AGA | AAA | AGA | AGA | AAT | TCT | 2892 |
|---|---|---|---|---|---|---|---|---|---|---|---|---|---|---|---|---|
| Val | Tyr | Arg | Ser | Val | Leu | Ile | Lys | Gly | Lys | Arg | Lys | Arg | Arg | Asn | Ser | |
| | | | | 930 | | | | | 935 | | | | | 940 | | |

| GGC | AGC | AGT | GAT | AGC | AGA | AGC | CAT | CAG | AAT | TCT | CCA | ACA | GAA | CTA | AAC | 2940 |
|---|---|---|---|---|---|---|---|---|---|---|---|---|---|---|---|---|
| Gly | Ser | Ser | Asp | Ser | Arg | Ser | His | Gln | Asn | Ser | Pro | Thr | Glu | Leu | Asn | |
| | | | 945 | | | | | 950 | | | | | 955 | | | |

| AAA | GAT | AGA | ACC | AGT | AGA | GAC | TCC | AGT | CCA | GTT | ATG | AGG | TCA | AGC | AGC | 2988 |
|---|---|---|---|---|---|---|---|---|---|---|---|---|---|---|---|---|
| Lys | Asp | Arg | Thr | Ser | Arg | Asp | Ser | Ser | Pro | Val | Met | Arg | Ser | Ser | Ser | |
| | | 960 | | | | | 965 | | | | | 970 | | | | |

| ACC | TTG | CCA | GTT | CCA | CAG | CCC | AGC | AGT | GCT | CCT | CCC | ACA | CCT | ACT | CGC | 3036 |
|---|---|---|---|---|---|---|---|---|---|---|---|---|---|---|---|---|
| Thr | Leu | Pro | Val | Pro | Gln | Pro | Ser | Ser | Ala | Pro | Pro | Thr | Pro | Thr | Arg | |
| | 975 | | | | | 980 | | | | | 985 | | | | | |

| CTC | ACA | GGT | GCC | AAC | AGT | GAC | ATG | GAA | GAA | GAG | GAG | AGG | GGA | GAC | CTC | 3084 |
|---|---|---|---|---|---|---|---|---|---|---|---|---|---|---|---|---|
| Leu | Thr | Gly | Ala | Asn | Ser | Asp | Met | Glu | Glu | Glu | Glu | Arg | Gly | Asp | Leu | |
| 990 | | | | | 995 | | | | | 1000 | | | | | 1005 | |

| ATT | CAG | TTC | TAC | AAC | AAC | ATC | TAC | ATC | AAA | CAG | ATT | AAG | ACA | TTT | GCC | 3132 |
|---|---|---|---|---|---|---|---|---|---|---|---|---|---|---|---|---|
| Ile | Gln | Phe | Tyr | Asn | Asn | Ile | Tyr | Ile | Lys | Gln | Ile | Lys | Thr | Phe | Ala | |
| | | | | 1010 | | | | | 1015 | | | | | 1020 | | |

| ATG | AAG | TAC | TCA | CAG | GCA | AAT | ATG | GAT | GCT | CCT | CCA | CTC | TCT | CCC | TAT | 3180 |
|---|---|---|---|---|---|---|---|---|---|---|---|---|---|---|---|---|
| Met | Lys | Tyr | Ser | Gln | Ala | Asn | Met | Asp | Ala | Pro | Pro | Leu | Ser | Pro | Tyr | |
| | | | 1025 | | | | | 1030 | | | | | 1035 | | | |

| CCA | TTT | GTA | AGA | ACA | GGC | TCC | CCT | CGC | CGA | ATA | CAG | TTG | TCT | CAA | AAT | 3228 |
|---|---|---|---|---|---|---|---|---|---|---|---|---|---|---|---|---|
| Pro | Phe | Val | Arg | Thr | Gly | Ser | Pro | Arg | Arg | Ile | Gln | Leu | Ser | Gln | Asn | |
| | | | 1040 | | | | | 1045 | | | | | 1050 | | | |

| CAT | CCT | GTC | TAC | ATT | TCC | CCA | CAT | AAA | AAT | GAA | ACA | ATG | CTT | TCT | CCT | 3276 |
|---|---|---|---|---|---|---|---|---|---|---|---|---|---|---|---|---|
| His | Pro | Val | Tyr | Ile | Ser | Pro | His | Lys | Asn | Glu | Thr | Met | Leu | Ser | Pro | |
| | 1055 | | | | | 1060 | | | | | 1065 | | | | | |

| CGA | GAA | AAG | ATT | TTC | TAT | TAC | TTC | AGC | AAC | AGT | CCT | TCA | AAG | AGA | CTG | 3324 |
|---|---|---|---|---|---|---|---|---|---|---|---|---|---|---|---|---|
| Arg | Glu | Lys | Ile | Phe | Tyr | Tyr | Phe | Ser | Asn | Ser | Pro | Ser | Lys | Arg | Leu | |
| 1070 | | | | | 1075 | | | | | 1080 | | | | | 1085 | |

| AGA | GAA | ATT | AAT | AGT | ATG | ATA | CGC | ACA | GGA | GAA | ACT | CCT | ACT | AAA | AAG | 3372 |
|---|---|---|---|---|---|---|---|---|---|---|---|---|---|---|---|---|
| Arg | Glu | Ile | Asn | Ser | Met | Ile | Arg | Thr | Gly | Glu | Thr | Pro | Thr | Lys | Lys | |
| | | | | 1090 | | | | | 1095 | | | | | 1100 | | |

| AGA | GGA | ATT | CTT | TTG | GAA | GAT | GGA | AGT | GAA | TCA | CCT | GCA | AAA | AGA | ATT | 3420 |
|---|---|---|---|---|---|---|---|---|---|---|---|---|---|---|---|---|
| Arg | Gly | Ile | Leu | Leu | Glu | Asp | Gly | Ser | Glu | Ser | Pro | Ala | Lys | Arg | Ile | |
| | | | 1105 | | | | | 1110 | | | | | 1115 | | | |

| TGC | CCA | GAA | AAT | CAT | TCT | GCC | TTA | TTA | CGC | CGT | CTC | CAA | GAT | GTA | GCT | 3468 |
|---|---|---|---|---|---|---|---|---|---|---|---|---|---|---|---|---|
| Cys | Pro | Glu | Asn | His | Ser | Ala | Leu | Leu | Arg | Arg | Leu | Gln | Asp | Val | Ala | |
| | | | 1120 | | | | | 1125 | | | | | 1130 | | | |

| AAT | GAC | CGT | GGT | TCC | CAC | TGA | GGTTAGTCTC | TTGTATTAAA | CTCTTCACAA | 3519 |
|---|---|---|---|---|---|---|---|---|---|---|

```
Asn  Asp  Arg  Gly  Ser  His   *
          1135                1140
```

| | | | | |
|---|---|---|---|---|
| AATCTGTTTA | GCAGCAGCCT | TTAATGCATC | TAGATTATGG | AGCTTTTTTC | CTTAATCCAG | 3579 |
| CTGATGAGTT | ACAGCCTGTT | AGTAACATGA | GGGGACATTT | TGGTGAGAAA | TGGGACTTAA | 3639 |
| CTCCTTCCAG | TGTCCTTAGA | ACATTTTAAT | TCATCCCAAC | TGTCTTTTTT | TCCCTACCAC | 3699 |
| TCAGTGATTA | CTGTCAAGGC | TGCTTACAAT | CCAAACTTGG | GTTTTTGGCT | CTGGCAAAGC | 3759 |
| TTTTAGAAAT | ACTGCAAGAA | ATGATGTGTA | CCCAACGTGA | GCATAGGAGG | CTTCTGTTGA | 3819 |
| CGTCTCCAAC | AGAAGAACTG | TGTTTCAAGT | TCAATCCTAC | CTGTTTTGTG | GTCAGCTGTA | 3879 |
| GTCCTCATAA | AAAGCAAAAC | AAAAATTAGG | TATTTTGTCC | TAAAACACCT | GGTAGGAGTG | 3939 |
| TGTGATTTTT | TGCATTCCTG | ACAAAGGAGA | GCACACCCAG | GTTTGGAGGT | CCTAGGTCAT | 3999 |
| TAGCCCTCGT | CTCCCGTTCC | CTTTGTGCAC | ATCTTCCCTC | TCCCCATTCG | GTGTGGTGCA | 4059 |
| GTGTGAAAAG | TCCTTGATTG | TTCGGGTGTG | CAATGTCTGA | GTGAACCTGT | ATAAGTGGAG | 4119 |
| GCACTTTAGG | GCTGTAAAAT | GCATGATTTT | GTAACCCAGA | TTTTGCTGTA | TATTTGTGAT | 4179 |
| AGCACTTTCT | ACAATGTGAA | CTTTATTAAA | TACAAAACTT | CCAGGCTAAA | CATCCAATAT | 4239 |
| TTTCTTTAAT | GCTTTTATAT | TTTTTAAAA | TGTTAAAACC | CCTATAGCCA | CCTTTTGGGA | 4299 |
| ATGTTTTAAA | TTCTCCAGTT | TTTTGTTATA | TAGGGATCAA | CCAGCTAAGA | AAAGATTTTA | 4359 |
| AGTCAAGTTG | AATTGAGGGG | ATTAATATGA | AAACTTATGA | CCTCTTCCTT | TAGGAGGGAG | 4419 |
| TTATCTAAAA | GAAATGTCTA | TTAAGGTGAT | ATATTTAAAA | ATATTTTTGG | GTGTTCCTGG | 4479 |
| CAGTTTAAAA | AAATTGGTTG | GAGAATTTAG | GTTTTTATTA | GTACCATAGT | ACCATTTATA | 4539 |
| CAAATTAGAA | AATGTTATTT | AACAGCTGAA | TTATCTATAC | ATATCTTTAT | TAATCACTAT | 4599 |
| TGTTCCAGCA | GTTTTCAAGT | CAAATTAATA | ATCTTATTAG | GGAGAAAATT | CAATTGTAAA | 4659 |
| TTGAATCAGT | ATAAACAAG | TTACTAGGTA | ACTTCATATT | GCTGAGAGAA | ATATGGAACT | 4719 |
| TACATTGTTC | AATTAGAATA | GTGTTCTCCC | CAAATATTTA | TAAAACTTCT | CAAGATACTG | 4779 |
| CTACGTGTAA | TTTTATATGA | AGATAAGTGT | ATTTTTCAAT | AAAGCATTTA | TAAATTAAAA | 4839 |
| AAAAAAAAAA | AAAA | | | | | 4853 |

( 2 ) INFORMATION FOR SEQ ID NO:2:

( i ) SEQUENCE CHARACTERISTICS:
        ( A ) LENGTH: 1139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Pro  Ser  Gly  Gly  Asp  Gln  Ser  Pro  Pro  Pro  Pro  Pro  Pro  Pro
 1              5                   10                      15

Ala  Ala  Ala  Ala  Ser  Asp  Glu  Glu  Glu  Asp  Asp  Gly  Glu  Ala  Glu
              20                  25                      30

Asp  Ala  Ala  Pro  Ser  Ala  Glu  Ser  Pro  Thr  Pro  Gln  Ile  Gln  Gln  Arg
              35                  40                      45

Phe  Asp  Glu  Leu  Cys  Ser  Arg  Leu  Asn  Met  Asp  Glu  Ala  Ala  Arg  Pro
              50                  55                      60

Glu  Ala  Trp  Asp  Ser  Tyr  Arg  Ser  Met  Ser  Glu  Ser  Tyr  Thr  Leu  Glu
 65                  70                  75                      80

Gly  Asn  Asp  Leu  His  Trp  Leu  Ala  Cys  Ala  Leu  Tyr  Val  Ala  Cys  Arg
                    85                  90                      95

Lys  Ser  Val  Pro  Thr  Val  Ser  Lys  Gly  Thr  Val  Glu  Gly  Asn  Tyr  Val
```

|     |     |     |     |     | 100 |     |     |     |     | 105 |     |     |     |     | 110 |     |
| --- | --- | --- | --- | --- | --- | --- | --- | --- | --- | --- | --- | --- | --- | --- | --- | --- |

Ser Leu Thr Arg Ile Leu Lys Cys Ser Glu Gln Ser Leu Ile Glu Phe
                115              120              125

Phe Asn Lys Met Lys Lys Trp Glu Asp Met Ala Asn Leu Pro Pro His
    130              135              140

Phe Arg Glu Arg Thr Glu Arg Leu Glu Arg Asn Phe Thr Val Ser Ala
145              150              155              160

Val Ile Phe Lys Lys Tyr Glu Pro Ile Phe Gln Asp Ile Phe Lys Tyr
                165              170              175

Pro Gln Glu Gln Pro Arg Gln Arg Gly Arg Lys Gln Arg Arg
                180              185              190

Gln Pro Cys Thr Val Ser Glu Ile Phe His Phe Cys Trp Val Leu Phe
            195              200              205

Ile Tyr Ala Lys Gly Asn Phe Pro Met Ile Ser Asp Asp Leu Val Asn
    210              215              220

Ser Tyr His Leu Leu Leu Cys Ala Leu Asp Leu Val Tyr Gly Asn Ala
225              230              235              240

Leu Gln Cys Ser Asn Arg Lys Glu Leu Val Asn Pro Asn Phe Lys Gly
                245              250              255

Leu Ser Glu Asp Phe His Ala Lys Asp Ser Lys Pro Ser Ser Asp Pro
            260              265              270

Pro Cys Ile Ile Glu Lys Leu Cys Ser Leu His Asp Gly Leu Val Leu
        275              280              285

Glu Ala Lys Gly Ile Lys Glu His Phe Trp Lys Pro Tyr Ile Arg Lys
    290              295              300

Leu Tyr Glu Lys Lys Leu Leu Lys Gly Lys Glu Glu Asn Leu Thr Gly
305              310              315              320

Phe Leu Glu Pro Gly Asn Phe Gly Glu Ser Phe Lys Ala Ile Asn Lys
                325              330              335

Ala Tyr Glu Glu Tyr Val Leu Ser Val Gly Asn Leu Asp Glu Arg Ile
            340              345              350

Phe Leu Gly Glu Asp Ala Glu Glu Ile Gly Thr Leu Ser Arg Cys
        355              360              365

Leu Asn Ala Gly Ser Gly Thr Glu Thr Ala Glu Arg Val Gln Met Lys
370              375              380

Asn Ile Leu Gln Gln His Phe Asp Lys Ser Lys Ala Leu Arg Ile Ser
385              390              395              400

Thr Pro Leu Thr Gly Val Arg Tyr Ile Lys Glu Asn Ser Pro Cys Val
            405              410              415

Thr Pro Val Ser Thr Ala Thr His Ser Leu Ser Arg Leu His Thr Met
            420              425              430

Leu Thr Gly Leu Arg Asn Ala Pro Ser Glu Lys Leu Glu Gln Ile Leu
        435              440              445

Arg Thr Cys Ser Arg Asp Pro Thr Gln Ala Ile Ala Asn Arg Leu Lys
    450              455              460

Glu Met Phe Glu Ile Tyr Ser Gln His Phe Gln Pro Asp Glu Asp Phe
465              470              475              480

Ser Asn Cys Ala Lys Glu Ile Ala Ser Lys His Phe Arg Phe Ala Glu
                485              490              495

Met Leu Tyr Tyr Lys Val Leu Glu Ser Val Ile Glu Gln Glu Gln Lys
            500              505              510

Arg Leu Gly Asp Met Asp Leu Ser Gly Ile Leu Glu Gln Asp Ala Phe
        515              520              525

| His | Arg | Ser | Leu | Leu | Ala | Cys | Cys | Leu | Glu | Val | Val | Thr | Phe | Ser | Tyr |
| | 530 | | | | 535 | | | | | 540 | | | | | |

| Lys | Pro | Pro | Gly | Asn | Phe | Pro | Phe | Ile | Thr | Glu | Ile | Phe | Asp | Val | Pro |
| 545 | | | | | 550 | | | | 555 | | | | | | 560 |

| Leu | Tyr | His | Phe | Tyr | Lys | Val | Ile | Glu | Val | Phe | Ile | Arg | Ala | Glu | Asp |
| | | | | 565 | | | | | 570 | | | | | 575 | |

| Gly | Leu | Cys | Arg | Glu | Val | Val | Lys | His | Leu | Asn | Gln | Ile | Glu | Glu | Gln |
| | | | 580 | | | | | 585 | | | | | 590 | | |

| Ile | Leu | Asp | His | Leu | Ala | Trp | Lys | Pro | Glu | Ser | Pro | Leu | Trp | Glu | Lys |
| | | | 595 | | | | 600 | | | | | 605 | | | |

| Ile | Arg | Asp | Asn | Glu | Asn | Arg | Val | Pro | Thr | Cys | Glu | Glu | Val | Met | Pro |
| | 610 | | | | | 615 | | | | | 620 | | | | |

| Pro | Gln | Asn | Leu | Glu | Arg | Ala | Asp | Glu | Ile | Cys | Ile | Ala | Gly | Ser | Pro |
| 625 | | | | | 630 | | | | | 635 | | | | | 640 |

| Leu | Thr | Pro | Arg | Arg | Val | Thr | Glu | Val | Arg | Ala | Asp | Thr | Gly | Gly | Leu |
| | | | | 645 | | | | | 650 | | | | | 655 | |

| Gly | Arg | Ser | Ile | Thr | Ser | Pro | Thr | Thr | Leu | Tyr | Asp | Arg | Tyr | Ser | Ser |
| | | | | 660 | | | | 665 | | | | | 670 | | |

| Pro | Pro | Ala | Ser | Thr | Thr | Arg | Arg | Leu | Phe | Val | Glu | Asn | Asp | Ser |
| | | | 675 | | | | 680 | | | | | 685 | | |

| Pro | Ser | Asp | Gly | Gly | Thr | Pro | Gly | Arg | Met | Pro | Pro | Gln | Pro | Leu | Val |
| | | 690 | | | | | 695 | | | | | 700 | | | |

| Asn | Ala | Val | Pro | Val | Gln | Asn | Val | Ser | Gly | Glu | Thr | Val | Ser | Val | Thr |
| 705 | | | | | 710 | | | | | 715 | | | | | 720 |

| Pro | Val | Pro | Gly | Gln | Thr | Leu | Val | Thr | Met | Ala | Thr | Ala | Thr | Val | Thr |
| | | | | 725 | | | | | 730 | | | | | 735 | |

| Ala | Asn | Asn | Gly | Gln | Thr | Val | Thr | Ile | Pro | Val | Gln | Gly | Ile | Ala | Asn |
| | | | 740 | | | | | 745 | | | | | 750 | | |

| Glu | Asn | Gly | Gly | Ile | Thr | Phe | Phe | Pro | Val | Gln | Val | Asn | Val | Gly | Gly |
| | | 755 | | | | | 760 | | | | | 765 | | | |

| Gln | Ala | Gln | Ala | Val | Thr | Gly | Ser | Ile | Gln | Pro | Leu | Ser | Ala | Gln | Ala |
| | 770 | | | | | 775 | | | | | 780 | | | | |

| Leu | Ala | Gly | Ser | Leu | Ser | Ser | Gln | Gln | Val | Thr | Gly | Thr | Thr | Leu | Gln |
| 785 | | | | | 790 | | | | | 795 | | | | | 800 |

| Val | Pro | Gly | Gln | Val | Ala | Ile | Gln | Gln | Ile | Ser | Pro | Gly | Gly | Gln | Gln |
| | | | | 805 | | | | | 810 | | | | | 815 | |

| Gln | Lys | Gln | Gly | Gln | Ser | Val | Thr | Ser | Ser | Ser | Asn | Arg | Pro | Arg | Lys |
| | | | 820 | | | | | 825 | | | | | 830 | | |

| Thr | Ser | Ser | Leu | Ser | Leu | Phe | Phe | Arg | Lys | Val | Tyr | His | Leu | Ala | Ala |
| | | 835 | | | | | 840 | | | | | 845 | | | |

| Val | Arg | Leu | Arg | Asp | Leu | Cys | Ala | Lys | Leu | Asp | Ile | Ser | Asp | Glu | Leu |
| | 850 | | | | | 855 | | | | | 860 | | | | |

| Arg | Lys | Lys | Ile | Trp | Thr | Cys | Phe | Glu | Phe | Ser | Ile | Ile | Gln | Cys | Pro |
| 865 | | | | | 870 | | | | | 875 | | | | | 880 |

| Glu | Leu | Met | Met | Asp | Arg | His | Leu | Asp | Gln | Leu | Leu | Met | Cys | Ala | Ile |
| | | | | 885 | | | | | 890 | | | | | 895 | |

| Tyr | Val | Met | Ala | Lys | Val | Thr | Lys | Glu | Asp | Lys | Ser | Phe | Gln | Asn | Ile |
| | | | 900 | | | | | 905 | | | | | 910 | | |

| Met | Arg | Cys | Tyr | Arg | Thr | Gln | Pro | Gln | Ala | Arg | Ser | Gln | Val | Tyr | Arg |
| | | 915 | | | | | 920 | | | | | 925 | | | |

| Ser | Val | Leu | Ile | Lys | Gly | Lys | Arg | Lys | Arg | Arg | Asn | Ser | Gly | Ser | Ser |
| | 930 | | | | | 935 | | | | | 940 | | | | |

| Asp | Ser | Arg | Ser | His | Gln | Asn | Ser | Pro | Thr | Glu | Leu | Asn | Lys | Asp | Arg |
| 945 | | | | | 950 | | | | | 955 | | | | | 960 |

| | | | | | | | | | | | | | |
|---|---|---|---|---|---|---|---|---|---|---|---|---|---|
|Thr|Ser|Arg|Asp|Ser|Ser|Pro|Val|Met|Arg|Ser|Ser|Thr|Leu|Pro|
| | | | |965| | | |970| | | |975| |

Val Pro Gln Pro Ser Ser Ala Pro Pro Thr Pro Thr Arg Leu Thr Gly
            980                 985                     990

Ala Asn Ser Asp Met Glu Glu Glu Glu Arg Gly Asp Leu Ile Gln Phe
        995                 1000                1005

Tyr Asn Asn Ile Tyr Ile Lys Gln Ile Lys Thr Phe Ala Met Lys Tyr
        1010            1015            1020

Ser Gln Ala Asn Met Asp Ala Pro Pro Leu Ser Pro Tyr Pro Phe Val
1025            1030            1035            1040

Arg Thr Gly Ser Pro Arg Arg Ile Gln Leu Ser Gln Asn His Pro Val
            1045            1050            1055

Tyr Ile Ser Pro His Lys Asn Glu Thr Met Leu Ser Pro Arg Glu Lys
            1060            1065            1070

Ile Phe Tyr Tyr Phe Ser Asn Ser Pro Ser Lys Arg Leu Arg Glu Ile
        1075            1080            1085

Asn Ser Met Ile Arg Thr Gly Glu Thr Pro Thr Lys Lys Arg Gly Ile
    1090            1095            1100

Leu Leu Glu Asp Gly Ser Glu Ser Pro Ala Lys Arg Ile Cys Pro Glu
1105            1110            1115            1120

Asn His Ser Ala Leu Leu Arg Arg Leu Gln Asp Val Ala Asn Asp Arg
            1125            1130            1135

Gly Ser His
        1140

( 2 ) INFORMATION FOR SEQ ID NO:3:

( i ) SEQUENCE CHARACTERISTICS:
    ( A ) LENGTH: 2461 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:3:

```
TGCCCGCCTT GGCCTCCCAA CGTGTAGGGA TTACAGGCGT GAGTCACCGC GCCTTGCCAA      60
ATTATTTATT ATTATTTTTT GGAGACAGGG TCTCTGTTGC CCAAGCTGTA GTGGTATGGC     120
CACAGTTCAC TGCAGACTCC CCAGGATTAG GCGTTCCTCC CACCTCAGTC TCCCAAGTAG     180
CTAGGATTAC AGGCGTCTAC CACCACTCTG GGTTAATTTT TCTATTTTTT GGAGAGACAG     240
GGTTTCACTA TGTCGCCCAG GCTGGACCTC GAACTCCTGT CTCAAGCAGC CCCCCCACCT     300
CGCCTCCCAA AGTGCTGGAT TTACAGGTGT GATCCACAAC GTCCAGCCTA TATACTTAAG     360
ATACTTCTAA ACCATTGTG  TTCAACTTCT GTTCTTGCCC CATAGTCACC TTGAGACTCA     420
TCACTTAGCC AACTCCAAAA GCATTGCTGA TTACTGTGAA TTTTACTAAG GTTTTCTTAA     480
GAGGGTTCCA TTGTCTCAAA ATTGTTCCTG AAATATCCTG TTACCTGTCT ACCTGATTTT     540
CTCCTATCTT CAGAGTTCCA TTTCCTGTCC TCCCGCCTGT CATTATACCT TCCATAAGCC     600
CCTACTTTTG TCCCAGCACT TTTCCCTCTG TCAGTTTACA TATCCCACCA AGCAAAACAA     660
AAATAGCAAA ACAGTAATGC CTTCTGAATC CTCAAATTGC TCAATCCTCA GATTGCTCCT     720
CAATCTGGAA AATGTTTTAT ATCAAGCCCA TTTATAAATC AAGGATTGGC AATTTAAAAA     780
ATTAAAATAA AGAAAGGAGA ATTGGAAATA AAATGAATTG GCTGGGCACG GTGGCTCACG     840
CCTGTAATCC CAGAACTTTG GGAGGCCGAG GTGGGTGGAT CACTTGAGGT CAGGAGTGCG     900
```

-continued

| | | | | | |
|---|---|---|---|---|---|
| AGACCAGCCT | GGCCAACATG | GTGAAACCCT | GCCTGTTCTG | AAAATCCAAA | AATCAGCTGG | 960 |
| GTGCGGCGGC | GCACACCTGT | AATCCCAGAT | ACTCAGGAGG | CTGAGGCAGG | AGAATCGCTT | 1020 |
| GATCCCAGGA | GGCGGAGGTT | GCAGCGAGCC | GAGATCGTGC | CACTACACTC | CAGTCTGGCC | 1080 |
| AACAGAGCCA | GACTCTGTCT | CACAAAAAAA | AAAAGTTTA | ATTCACGGAG | AGCCAGCTGA | 1140 |
| ACGGCAGACA | GGAGTTTGGT | TATCCAAATC | AGCCTACCAG | AAATTGGAGA | CTGGGGTTTT | 1200 |
| TAAAAGAATG | ACTTGGCGGG | TAGGGCCCA | GGGATTGGCG | AATGCTAATT | TGTCAGGTGG | 1260 |
| GAGGTGAAAT | CACAGGGGGT | TGAAGTGGGC | TCTTGCTGTC | TTCTGTTACT | GAGTGGAATT | 1320 |
| GCAGAACTTG | TTGAGCCAGA | TTATGGTCTG | AGTGGCGCCA | GCTAGTGCAT | CGGAATGCGC | 1380 |
| GGTCTGAAAA | GTATCTCCAG | CACCAATCTT | AGGTTTTACA | ATAGTGATGT | TATCCCTGAG | 1440 |
| AGCAATTGGG | GAGGTCAGGA | ATCTTATAGC | CTCTGGCTGC | AAGCCTCCTA | AATCATAATT | 1500 |
| TCTAATCTTG | TGGCTAATTT | GTTAGTTCTA | CAAAGGCAGA | CTGATCCCCA | GGCAAGAATG | 1560 |
| GGGTTTGTTT | TTGGAAAGGA | CTGTTACAAT | CTTTGTTTCA | AAGTGAAATT | AGAAATTAAA | 1620 |
| TTCCTCCTGT | AGTTAGTTAG | GTCTTCGCCC | AGGAATGAAC | AAGGGCAGCT | CGGAAGTGAG | 1680 |
| AAGCGTGGAG | TCATTTAGGT | CAGATTCCTT | GCACTGTCAT | AACTTTCTCA | CTGTTAGGAT | 1740 |
| TTTTGCAAAG | GCAGTTTCGT | GAACGTACAG | AGACAGGCCC | TTGCTATTAT | CCCTATTTTT | 1800 |
| TAGATAAGGA | TATCCAGCCG | ATGAGGAAGT | TTTACTTCTG | GAACAGCCTG | GATACGAAAC | 1860 |
| CTTCACACGT | CAGTGTCTTT | TGGACATTTT | CTCGTCAGTA | CAGCCCTGTT | GAATGTTCTC | 1920 |
| ACGGTGGGGA | GGTACGTGTT | TAAAATACGG | GGAAGGTGCT | TTTATTTCAC | CCCTGGTGAA | 1980 |
| ACTAGGGGAG | CTAATTTTTT | TAAACATGAT | TTTTGTCCCC | CTTGAACCGC | CGGCCTGGAC | 2040 |
| TACGTTTCCC | AGCAGCCCGT | GCTCAAGACT | ACGGGTGCCT | GCAGGCGGTC | AGCGTCGTTT | 2100 |
| GCGACGGCGC | AGACGCGGTG | CGGGCGGCGG | ACGGGCGGGC | GCTTCGCCGT | TTGAATTGCT | 2160 |
| GCGGGCCCGG | GCCCTCACCT | CACCTGAGGT | CCGGCCGCCC | AGGGGTGCGC | TATGCCGTCG | 2220 |
| GGAGGTGACC | AGTCGCCACC | GCCCCCGCCT | CCCCCTCCGG | CGGCGGCAGC | CTCGGATGAG | 2280 |
| GAGGAGGAGG | ACGACGGCGA | GGCGGAAGAC | GCCGCGCCGT | CTGCCGAGTC | GCCCACCCCT | 2340 |
| CAGATCCAGC | AGCGGTTCGA | CGAGCTGTGC | AGCCGCCTCA | ACATGGACGA | GGCGGCGCGG | 2400 |
| CCCGAGGCCT | GGGACAGCTA | CCGCAGCATG | AGCGAAAGCT | ACACGCTGGA | GGTGCGCTCG | 2460 |
| C | | | | | | 2461 |

( 2 ) INFORMATION FOR SEQ ID NO:4:

( i ) SEQUENCE CHARACTERISTICS:
        ( A ) LENGTH: 561 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 312..551

( x i ) SEQUENCE DESCRIPTION: SEQ ID NO:4:

| | | | | | |
|---|---|---|---|---|---|
| CAGCCCTGTT | GAATGTTCTC | ACGGTGGGGA | GGTACGTGTT | TAAAATACGG | GGAAGGTGCT | 60 |
| TTTATTTCAC | CCCTGGTGAA | ACTAGGGGAG | CTAATTTTTT | TAAACATGAT | TTTTGTCCCC | 120 |
| CTTGAACCGC | CGGCCTGGAC | TACGTTTCCC | AGCAGCCCGT | GCTCAAGACT | ACGGGTGCCT | 180 |
| GCAGGCGGTC | AGCGTCGTTT | GCGACGGCGC | AGACGCGGTG | CGGGCGGCGG | ACGGGCGGGC | 240 |
| GCTTCGCCGT | TTGAATTGCT | GCGGGCCCGG | GCCCTCACCT | CACCTGAGGT | CCGGCCGCCC | 300 |

```
AGGGGTGCGC T ATG CCG TCG GGA GGT GAC CAG TCG CCA CCG CCC CCG CCT      350
              Met Pro Ser Gly Gly Asp Gln Ser Pro Pro Pro Pro Pro
               1               5                   10

CCC CCT CCG GCG GCG GCA GCC TCG GAT GAG GAG GAG GAG GAC GAC GGC      398
Pro Pro Pro Ala Ala Ala Ala Ser Asp Glu Glu Glu Glu Asp Asp Gly
     15              20                  25

GAG GCG GAA GAC GCC GCG CCG TCT GCC GAG TCG CCC ACC CCT CAG ATC      446
Glu Ala Glu Asp Ala Ala Pro Ser Ala Glu Ser Pro Thr Pro Gln Ile
 30              35                  40                      45

CAG CAG CGG TTC GAC GAG CTG TGC AGC CGC CTC AAC ATG GAC GAG GCG      494
Gln Gln Arg Phe Asp Glu Leu Cys Ser Arg Leu Asn Met Asp Glu Ala
             50                  55                      60

GCG CGG CCC GAG GCC TGG GAC AGC TAC CGC AGC ATG AGC GAA AGC TAC      542
Ala Arg Pro Glu Ala Trp Asp Ser Tyr Arg Ser Met Ser Glu Ser Tyr
                 65              70                  75

ACG CTG GAG GTGCGCTCGC                                                561
Thr Leu Glu
         80
```

( 2 ) INFORMATION FOR SEQ ID NO:5:

( i ) SEQUENCE CHARACTERISTICS:
        ( A ) LENGTH: 80 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Pro Ser Gly Gly Asp Gln Ser Pro Pro Pro Pro Pro Pro Pro Pro
 1               5                   10                      15

Ala Ala Ala Ala Ser Asp Glu Glu Glu Glu Asp Asp Gly Glu Ala Glu
             20                  25                  30

Asp Ala Ala Pro Ser Ala Glu Ser Pro Thr Pro Gln Ile Gln Gln Arg
         35                  40                  45

Phe Asp Glu Leu Cys Ser Arg Leu Asn Met Asp Glu Ala Ala Arg Pro
     50                  55                  60

Glu Ala Trp Asp Ser Tyr Arg Ser Met Ser Glu Ser Tyr Thr Leu Glu
 65              70                  75                      80
```

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

```
ACGCTGGAGG TGCGCTCGC                                                   19
```

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

TCTTTTACAG GGAAATGAT 19

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

AGAGCAGAGG TAACTATGT 19

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

TTAATACCAG CTTAATCGA 19

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

GAAACAGCGG TAGGTTTTC 19

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

TCCCCCAAAG GCGACAGCC 19

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:12:

ATGCAAAAGG TAAGAAAAT 19

(2) INFORMATION FOR SEQ ID NO:13:

( i ) SEQUENCE CHARACTERISTICS:
    ( A ) LENGTH: 19 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:13:

AATCCTGCAG GTAATTTCC    19

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

ATTTTAAAGG TAGGTTTGT    19

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

ACACCATAGG CTTATCTG    18

( 2 ) INFORMATION FOR SEQ ID NO:16:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:16:

GAAAAAAGG TTTGTAAGT    19

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

TTCATCATAG CTCCTTAAG    19

( 2 ) INFORMATION FOR SEQ ID NO:18:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear (i i) MOLECULE TYPE: DNA (genomic)

(x i) SEQUENCE DESCRIPTION: SEQ ID NO:18:

AGAGAGTTTG TGAGTACTT 19

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:19:

TTCCTATAGT AAAGCCAT 18

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:20:

TTTGACAAGG TGAGTTTAG 19

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:21:

TTTTCTTTAG TCCAAAGCA 19

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:22:

GATTCTCAGG TTAGTTTGA 19

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:23:

CCTTTTTTAG GACATGTTC         19

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:24:

GTGCTAAAGG TAATTGTGC         19

(2) INFORMATION FOR SEQ ID NO:25:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:25:

ATTTCTACAG AAATTGCCA         19

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:26:

GATTTATCTG TGAGTAAAA         19

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:27:

ATTTTATAGG GTATTCTG         18

(2) INFORMATION FOR SEQ ID NO:28:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:28:

TTTTATAAGG TATTTCCCA         19

(2) INFORMATION FOR SEQ ID NO:29:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:29:

TTTATTTCAG GTGATAGAA   19

( 2 ) INFORMATION FOR SEQ ID NO:30:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:30:

TGTGAAGAGG TGAAAATCA   19

( 2 ) INFORMATION FOR SEQ ID NO:31:

( i ) SEQUENCE CHARACTERISTICS:
  ( A ) LENGTH: 18 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:31:

TCTTCATAGG TCATGCCA   18

( 2 ) INFORMATION FOR SEQ ID NO:32:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:32:

TTGGAAGGAG TAAGTTTAA   19

( 2 ) INFORMATION FOR SEQ ID NO:33:

( i ) SEQUENCE CHARACTERISTICS:
  ( A ) LENGTH: 20 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:33:

TTGACCCCTA GGCATAACAT   20

( 2 ) INFORMATION FOR SEQ ID NO:34:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:34:

CTGTGCAAGG TAAGGAAGG 19

( 2 ) INFORMATION FOR SEQ ID NO:35:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:35:

CTGTCACTAG GTATTGCCA 19

( 2 ) INFORMATION FOR SEQ ID NO:36:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:36:

TTTAGAAAGG TAATTTTTC 19

( 2 ) INFORMATION FOR SEQ ID NO:37:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:37:

TATCTCCTAG GTATACCAT 19

( 2 ) INFORMATION FOR SEQ ID NO:38:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:38:

ATGGCAAAGG TGAGTACCA 19

( 2 ) INFORMATION FOR SEQ ID NO:39:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:39:

GTTTGCCAGG TCACAAAA 18

(2) INFORMATION FOR SEQ ID NO:40:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:40:

CGGAGCCAGG TAACTACAT 19

(2) INFORMATION FOR SEQ ID NO:41:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:41:

TTCTCTAAAG GTGTATAGA 19

(2) INFORMATION FOR SEQ ID NO:42:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:42:

AAGATAGAAG TGGGATCTT 19

(2) INFORMATION FOR SEQ ID NO:43:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:43:

CTGGCTGCAG CCAGTAGAG 19

(2) INFORMATION FOR SEQ ID NO:44:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:44:

CAGGCAAATG TAAGTATGA 19

(2) INFORMATION FOR SEQ ID NO:45:

( i ) SEQUENCE CHARACTERISTICS:
  ( A ) LENGTH: 20 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:45:

| | |
|---|---:|
| TTTTTAAACA GATGGGATGC | 20 |

( 2 ) INFORMATION FOR SEQ ID NO:46:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:46:

| | |
|---|---:|
| CCTTCAAAGG TGAGCCTAA | 19 |

( 2 ) INFORMATION FOR SEQ ID NO:47:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:47:

| | |
|---|---:|
| CCCACCATAG AGACTGAGA | 19 |

( 2 ) INFORMATION FOR SEQ ID NO:48:

( i ) SEQUENCE CHARACTERISTICS:
  ( A ) LENGTH: 3865 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:48:

| | | | | | | |
|---|---|---|---|---|---|---:|
| GTAGGTTTTC | TTGTTGGTTC | ATCAGGAATA | CACATTAGTC | TGTGCTGCAG | TGTTGATATT | 60 |
| CTGCTAGGTT | TTTTTTTTCT | GGTTTTAAAA | AGAAATAAG  | ATTTAAAAAA | TCTTTTTCCT | 120 |
| CAGTCGTTTT | CTTTTAATGA | TGCTTCCGGG | GCTTCACATT | GTGGGTTAGC | CATGAAGAGT | 180 |
| GGCTTTCACA | TATTGCTAAA | TGTATACAGG | TCTGTGTTTC | TATAAACTAC | ATGTGTCTTA | 240 |
| TTTCATTTTA | TTATTATTTA | CCTCCTCAGT | GATCCTTGTT | CTGAAACCTT | CCTTTTTCAT | 300 |
| TTAAGCAACA | AAAAATGCAG | ACTGTACAAG | TCAGACTTAG | GGATTTTCAC | CCTTTCGCCG | 360 |
| CCTTGGAGAG | TTCTGTATCT | GTATCGGAT  | ATATATATTT | TTTATTGCGC | AGGGGCCATG | 420 |
| CTAATCAATG | TATTGTTCCA | ATTTTAGTAT | ATGTGCTGCC | GAAGGGAGCA | CTGCCCTAGA | 480 |
| TATAGATCAC | TATATTAACC | ACTATATTTT | CTACTAGTGA | TTATATAGAC | TATTTTATGT | 540 |
| CAAACTGAGT | AATAAATAAT | CCCCTTGAAA | TGACTTCTCT | ATGTATTTTG | ATGTTTATAA | 600 |
| TGAATTCAGA | ATAGAGAGAC | TGGATTGGGA | AAAGACAGGA | GAACTGAAAC | TATTATGAAT | 660 |
| TTGTGCTTTC | TGATCACTTC | TGCAAAGTCT | ATAAGCATGC | TCTGACTCAG | TGTTTTCTAC | 720 |
| CTTTCCTGAT | AGATAAAGGC | AGTTATGGAA | TACACATTTT | CCTTCTTTAT | CATTGAAAGT | 780 |

```
TTTTTCATAA AGTAGAAATG AAAATTCTAA CAATTAAAAA AATGTTGACA AGAAAAGTAA    840
AGGGAAAGGA GTTAAAATTA TTTGGCTAGA ATAAATAATG TTTGCTTCTC TTTAAATATA    900
AAAGTTTTCC CAGACTGTGA AGGATGTTTA CATTAAGTGT AACCTTTTAA AATAAAATG     960
GAATGACAAA CCAGGAGGAA AAAAATTTA AAAAAACTAG AACTATTTAC ATTTTAATAT    1020
AGATGGCACC ACTGATACAG AAGCATCTGG TCTAGCTCAC TTACAGTTTT GGGGAATTGA   1080
CTATTTAAAA TGAAGCATTC TGAGCCAGGC GGGTTGGCTC ACGCCTGTAA TCCCAGCACT   1140
TTTATGAGGC TGAGGCAGGC GAATCACCTG AGTTCAGGAG TTCAATACCA GCCTGGCCAA   1200
CGTGGCAAAA CCCCGTCTCT ACTAAAAATA CAAAAATTAG CTGTGCATGG TGGTGCATGC   1260
CTATAATCCC AGCTACTCGG GAGGCTGAGT CAGTTGAATC CCTTGAACCG AGAAGCAGAG   1320
GTTGTGAGCC AAGATCGTAC CATTGCATTC GAGCCTGGGC GACAGAATGA AACTCCATCT   1380
CATAAATAAA TAAATAAACT AATAAAATGA CATATTCTCC TAGCACTTTG GGAGGCCGAG   1440
GCAGGTGGAT TGCTGGAGGT CAGGAGTTCA AGACTAGCTT GGCCAATGTG CCAAAACCCC   1500
ATTTCCATTA AAAATACAAA AATTAGGCAG GTATGGTGGT GTGTGCCTGT TGTCCCAGTT   1560
ACTTGAGGGC TGAGGCAGGT GAATCACTTG AACCCAGGAG TCGGAGGTTT CAGTGAGCTG   1620
CGATCGCGCC AATGCACTCC AGCTTAGGTG ACAGAGTGAG ACTTCGTCTC CAAATAAATA   1680
AATAAAAAAT GAAGTATTCT AAAGGTTTGA ATAGAAGCTT TGTACTGAGT CTGAGTGAGG   1740
CCAATGTGAT CATTTATGGG AAGATATCTT CTTTGTTTGG AGTATCTGGA AAATAATTTC   1800
AGATTGCACT TGTTTTGCTA TTTCTTAGGA TATATATACT ACCTAATTCT AATTAAGAGA   1860
ATTTTAAAAG GCCATGTGCA GTGGCTCACA CCTGATCCCC AGCACTTTGG GAGGCTGAAG   1920
TGGACAGATC ACTTGAGCCC AGGAGTTTGA GACCAGCCTG GACAGTATGG CGAAACTTCA   1980
TCTCCACAAA AAATACAAAA ATTAGCTTGG AGTGGTGGCG CACACCTGTG GTCCCAGCTA   2040
CTGGGGAGGC TGGAGGTGGG GGGATCACTT GAGCCTGGGA GGTTGAGGCT GCAGTGAGCT   2100
GTGCTCATAC CACTGTACTC CAGTTTGGGT GACAGAGCAA GACCTTGTTT CAAAAAAAA   2160
AAAAAAAGT AAATCACTTT ATTAGAGATT TTACATTTTA ATCACTTTGT ATACTTTCTG   2220
TTAGCTCTTT CTGTTAACTA TAGTCATAAT GTATAGCACT TACTGAGCAT TTACTTTGGG   2280
GCAGGGACTC TTAAGACTTC AATATGTATT ACTTCAGTTA ATCCCTCTGA CAACCTTGTG   2340
ATACTCATAC TATTGTTAGA TAGAGAAAAT TAACCGCAGA GAGGTTAAGT AATTTGGCCA   2400
GGGTCGCACA ACCAAGCGTG GAGTTCTTAT TGAAACTGAC TGCGGGAACC CATGTGCTTT   2460
ACTGTGACTA TATACTGCAT CTCTCACACA CTATCTGAAA ATGTGTCACT ATTTGTTTAG   2520
CACTTATCCA CAGGAAATAC TGTCAGGTAT TATGTAGGAC ACAAGCATTT TTAAAACAC    2580
CAAACCCCAC AGTTTTTGTT TTCTGAGAGC TTACAGTACA GTCAGCGAGA TGAGGCAGGT   2640
ATGAAGATTC CAGTGCATGC AATGCAGTGT GTTATAAAAG TCCCATGACT ACCAGAGGGA   2700
ATACAGATGT AAAACTTAGG AGGAAAAGAA ATCACTCTGG ATGAGCCAGT CAGGTAAGTT   2760
TACATGGAAT AAGTAGAAAT GGGTCTTGAA AGATGGGTAC GAGTTTGATA GGTGAATTTG   2820
AAGATACAGA TAGCACCTTC TGTGTAGAGG AAACAAGAAA AGACAAAAGC AGTAAAGCAA   2880
GAAGAAATGT GGGAGGTTAG TCAAGTTTTT TTTTCTAGAA TTCTCAAGTT GTAGAGCCAG   2940
AATTAAGAGT AGCTTAAGTG TTAAGCTAAA AAAAATTGAA TTTTATTTTG GTAGGCAACT   3000
AAAACTAGAA ATAGTTTATC ATGCGCCTAT GGTAGAGAGG ATACTTTTAA AAGCAGAACA   3060
CTGACATTTA ATCCTTGCCA TGGAGTGGTG AACTAAGTAC AGTATTGTAC CCAAGTAGAG   3120
TAATCTTTTG ACAGATGAAA TGACTAAGGC CCAGGTGAGC AAGTGTACCC TAGCTAATGG   3180
```

| | | | | | |
|---|---|---|---|---|---|
| CAGTGCTGGA | ACTAAATCTA | ATCTAATCTT | CTCCACGGAA | TTTCGTTCTT | CTGGGCACCT | 3240 |
| TGTTAGAATA | AGGCTGTTGG | GAGGTGGAGA | CCACAGATTT | CTTGTCTAAA | AGTTGTCAGA | 3300 |
| GGTTTTGGTA | GAAAAGCCAA | GCTTAAAGCA | GGTCTGAAAC | TTGGCAGACT | ACTTGGCAAT | 3360 |
| ATACAACAGG | TACTCTTAAT | GGATGGAAGT | ATAAGGAATT | ATAGGAAGCT | CATAATTTAC | 3420 |
| ATTAAAAGG | CCTTTTGTGA | TTTGATATAG | TCTGGAATAT | CTTTAAGGAG | GGAGGGAGGG | 3480 |
| ATACAGGTCA | TTAGCTATGA | TAAAGGAGAA | AAAAATAAGG | ACATATCTGA | CTGCATATAG | 3540 |
| TGGTCCTGAA | TCAGCATAGC | ATTGCTGTGT | CATCGAAAGA | ACTATTTTA | TTCATTTAT | 3600 |
| TTTCCACCTC | ACCTATCTTG | CCTTCACAAA | ACTTAAAAG | ATTCTTAAG | AATTTTCTTT | 3660 |
| TCTTTGAGAT | GGGCTCTTTC | CCTGGTACCC | AGCTATTTCC | TACCAATATT | TTGTTAAGGC | 3720 |
| AGAACGTCCA | CGTTTTCCAT | GTGAAGCTGA | ATCTGTTGTC | TCTCCCTTTA | ACTGTGGGTT | 3780 |
| TTATTTTACA | CCTGATTTAT | AATCATTTGG | GATTTTTTT | TCTGATCTTC | TGGTGTCTCG | 3840 |
| TGACTGGGGT | TTTCTTCCCC | CAAAG | | | | 3865 |

(2) INFORMATION FOR SEQ ID NO:49:

(i) SEQUENCE CHARACTERISTICS:
(A) LENGTH: 4576 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:49:

| | | | | | |
|---|---|---|---|---|---|
| GTAAGAAAAT | AGTAATATTT | ATTTAGATTT | AATATGTCTA | TTTACATTAC | CAGGTATTAA | 60 |
| TCTCGTCAAC | TCCTAATATG | TATCAGGAAA | AGATTTCCAC | TGAAAATTTT | CTCAAGGGTT | 120 |
| TTAATCCTAG | ATTCTTTTTT | AAGTATTGCC | TTTCCATCAA | AGGATCTATT | GGATTTCTTT | 180 |
| ACAATATCCA | AATCTCTCTT | ATTAAATGGA | AAGTCCATTA | ACTTCGTTGT | ATACAACATC | 240 |
| TTTCCTACCC | AAAGCTACTC | TCCTCAAATT | ATGAGCTGAA | AACACATAAT | CCTGTATATG | 300 |
| CTTGTATTGC | GAACTCTATC | TTCCATGAGA | TGTATCTTAT | TTAGTCTGAG | CGCAATTACT | 360 |
| GATCAACCTC | AGAGCTGTTC | AGATTTTTT | GTGTGTCTTG | TTCACATAAG | TATACTTAGT | 420 |
| CAAATGCTTT | TATATACTAT | TTATTTTCTT | TCCCTTTTT | CTTGTCTCAT | TTAACCTACC | 480 |
| CAAGGTCTGC | ATTCAGTGAA | ATACATGTCT | CTATTATTTT | TTGTCCTTTT | TGTATTTATT | 540 |
| TATTTATTTA | TTTATTTGAG | ATGGAATCTC | ATTCTGTCTC | CCAGGGCTAG | ATTGTAGTGG | 600 |
| CACAATCTCG | GCTCACTGCA | GGCTACACCT | CCCAGGTTCA | AGTAATTCTC | CTGCCTCAGC | 660 |
| CTCCCGAATA | GCCGTGATTA | CAGGCGCCCA | CCACCATGCC | CAGCTAATTT | TTGTGTTTTC | 720 |
| AGTAGAGATG | GGGTTTCACC | ATGTTGGCCA | GGCTGGTCTC | AAACTCCTGA | CCTCAGGTGA | 780 |
| TCTGCCTGCC | CTGGCCTCCC | ACAGTGCTGG | GATTATAGGC | ACGAGCCACT | GCGTCCAGCA | 840 |
| CCTTAGTATC | TTTCTATGTA | GAACGAATGC | TCCCAGGTAG | ATGGGAAAGT | GCAGATATAT | 900 |
| TATTATGTAG | TCAGCTCCTG | TATACCATGT | GGCTTGGCCT | TCGTCACTAA | GATGGCTCAC | 960 |
| TCTGAATGCA | AAGTTATCAC | AGAGTCTTAG | GTGCTGGAAG | GAGTTGCACA | GGTATCACTG | 1020 |
| AGACTCTCAT | TATTAGATTA | ACTAGCTTAA | CTTACTTTAT | TTTTTTTGA | GATGGAGTCT | 1080 |
| CACTCTGTTG | CCCAGGCTGG | AGTGCAGTGG | TGCGATCTCG | GCCCACTGCA | ACCTCTGCTG | 1140 |
| CCCGGGTTCA | AGCGATCTCC | TGCCTCAGCC | TCCCGAGTAG | CTGGGATTAC | AGGTGCCTGC | 1200 |
| CACTGTGCCC | GGCTAATTTT | TTGTCGTTTT | AGTAGACACG | GAGTTTCACC | ATCTTGGCCA | 1260 |

| | | | | | | |
|---|---|---|---|---|---|---|
| GGCTGGCCTT | GAACTCCTGA | CCTCGTGATC | CACCTGCGTC | AGCCTCCCAA | AGTGCTGGGC | 1320 |
| TTACAGGCGT | GAGCCATCGC | ACCCAGCCTA | GCTTAACTCA | GTTACTTTAT | TTTCTATTTT | 1380 |
| TATTTTTATT | TTTGACACAG | GATCTTGCTC | TGTTGCCCAG | GCTGGAGTGC | AGTGGTATGA | 1440 |
| TCTCTGCTCA | CTGCAACCTC | CGCCTCTTGT | GTTCAAGTTG | ATTCTTGTGG | CTCAGCCTCT | 1500 |
| TGAGTAGCTG | GGATTGCAGG | CATGCACCAT | TATACCTGGC | TAATTTTTGT | ATTTTTAGTA | 1560 |
| GTGTTGGGGT | TTTGCCATGT | TGGCCAGGGT | GGTCTCGAAC | TCCTGACCTC | AAGTGATCTG | 1620 |
| CCACCTCGGC | CTCCCAAAGT | GTTGGGATTA | CAGGTGTTGA | GCCACCATGC | TCAATCAGCT | 1680 |
| TAGTTACTTT | AAAGATTAGG | CAGCTGAGCC | CAGAAACTAG | CTGCTGGGAA | CAAAGCTAAG | 1740 |
| ATTGAACTCA | GATCTCCTGG | TTCCTGGTTC | TTAGTTTCAT | ACTGGCTGTG | AAGGCCTCTG | 1800 |
| GGAAGAATGT | GTTACATTGT | TGGTCTCCAG | GTTTGATTTG | TCCTGGTCCC | TCTCTGGCTA | 1860 |
| ATTAGGGTGA | GAGCCGCCAT | CCTTCCTTCC | CTGAGCTGCA | TGCTTGATTC | AAGAGAAAAA | 1920 |
| TCTTTCTTTT | GTCATACATG | ACACTGGCAT | GTTTCTTTAA | TGATGATAAA | GGCGACATGA | 1980 |
| TCAGTGGCAT | GAAATAAAGG | TTTTGGAGTA | TATAAACCAT | TTTTACAGCG | GCTACAAATT | 2040 |
| TTAGAATGTG | TGACTGCTAT | TATGTATGAT | GGTAATCTTT | TCATATGATT | GTATTGGGCA | 2100 |
| AGTATGTCTC | ATTTCTAGGG | TTTTTATCTG | TTTTGTTTGT | CTTTTATGGC | ATATGTGTAC | 2160 |
| TTAGAAGTAA | ATATAGTTGG | TACTATATAT | AATATGTACA | ATACAATAAA | AATAATTTC | 2220 |
| ATTGTCCTTA | TTTTGTTCTC | ACTGGACCTG | TTGGGGTGGT | TTTTTCTCTG | TAATTAACTC | 2280 |
| AGTGTTTGAC | TTTTATCTCA | TTAATTCAGT | TTATAATAAT | TCCACCTTAA | GAACCTTTGT | 2340 |
| GGATTGGGCA | TGTTGGCGTA | TGCCTGGAAC | CTAGCTACTT | GGGAAGTTGA | AGTGGGAAGC | 2400 |
| GGAGGCTGCA | GTGAGCTGAG | ATTGCACCTC | CAGTTTGGGC | GAATTTGAGA | CCGTGTTTCG | 2460 |
| AAAAAAAAAA | AAAAAAAAAA | AGAAACTTGG | TCCTTTCACA | GTCCACCACT | GTGATCTTTT | 2520 |
| ATAATACACG | ATGATCTTTT | TCTAATAGTC | ATTTAATTGC | TTTAATTCAG | TTCTCATTTA | 2580 |
| TTTGGGGGAA | AGGTGTACTC | TTTTATAGCC | ACCTTTCTAA | TGACAAATAA | GCCAACTCTG | 2640 |
| GAGATGAAAC | ATTTCTATTT | ACTTGTTATC | TTTGTTGATT | AAAAGATAAA | ATACCTCACA | 2700 |
| AAGTCAGATT | TATTTGTAAG | GTCAGGATTT | GAAATAGAAA | ATACGTCATG | TTGAGAGAGT | 2760 |
| CCTAGAATTT | AATTTAAATT | AGATTCTGAT | CTTTAGGGGC | ATTTCAGCTT | TTTATTAGAT | 2820 |
| GTTACGAGTA | CTGTTTTTTT | TTTTTTTTTT | TTTGCCTTCT | ATGGCAAGTG | CACACCAGTA | 2880 |
| ACAAGTTTAG | GCTTGTTGGT | GTGATGGGCT | TTGTAGCTTG | AAATCAGTAG | GTGCTACTTA | 2940 |
| CTTACTTTTT | TACACATGAG | GAACCAAGTA | TATTTTAATA | TTAAACCTCT | TTATAGGAGA | 3000 |
| GCCAAGCAAG | TTGGTTTGGC | TGTATCAATG | CGCAGTTTGA | TGTGGTGATT | ATCGTTTGCC | 3060 |
| TGCTTTGGCA | GAGGAGGATT | TTTTTTTCTC | TTTAGTTCAT | TTAAGTTGAT | TGTTGAATG | 3120 |
| TTTCCATCTA | AACAAAAAAG | AATTGCTTTG | TATACGCTGA | GGTAAGTGGT | AACTTTCTTT | 3180 |
| GGAGGAACAG | AGAGAAAGGG | AAACCTGAAA | CAAAACTGCA | GGTGTGTGTG | TGTGTGTACA | 3240 |
| TGTACACTTG | GGTAGGCGTT | AAGTGTGAAA | TGCTGAGGTT | TGGAAATAAT | TCTTCATATG | 3300 |
| TATGTTAGCT | TATTTAAATT | GAATTTATCT | GATGATACAA | GAATGTAAAA | TCACCATGAA | 3360 |
| GCATACATGT | GCAGTGTTTA | ACTAAAAAAG | GATGGGCTTG | AAGTTATAAA | ATAACTAGAA | 3420 |
| ATAATTCTTA | ATTTCTAGAA | AATTAAGATA | ATAATAAAAT | GGTTTAACTA | CACGTAAAAA | 3480 |
| TGTGTTCAGT | GTTAGAGTTC | AACCAGCACT | GCAGAAAATT | ACATGTTTCT | GTCAGTTTAG | 3540 |
| GTTTTTGATT | TCTTATTTCC | CTGTTACCAA | GCATCAGCAA | TTATTCTTGG | GATTATTAGC | 3600 |
| CCTGGAATTG | AAAGATATTT | AATGGTACTC | CTGTTGCATT | AATTTGTCTG | AGTTTATGTA | 3660 |

| | | | | | |
|---|---|---|---|---|---|
| GAAAAGTATT | AAAAATGTTA | CTGTTGGAGT | CTGATAAAAA | GTTCTGGTCT | TTTAAAAATA | 3720
| TGTGTATGAG | AAATAGCATG | AACTCAGGAG | GCAGAGCTTG | CAGTGAGCTG | AGATCGTGCC | 3780
| ACTGCACTCC | AGCCTGGGCG | ACAGTGAGAC | TCCATCTCAA | AAAAAAAAAA | TGTATATGAG | 3840
| AATAATTAAG | TGAATTATTT | TTTCGGCTGT | CTCCTAAGTA | TTTCTAATAA | TTTTCATGAC | 3900
| AGAAAAATGT | TTTCATGCAA | AACAATTTCC | TTACAGTTTG | AGATAATTTA | TAAATGTTTT | 3960
| GTGTTCAGAA | TTTTCAAAGA | AAAGACCAAT | GATAAAGTTT | TATTCAGCTA | CTAGGTATTT | 4020
| AATAAACACT | TAATGATGAA | TGGCATTTTT | AGTAAAGTTA | TAGTTTCAC | TAAGCTGTTA | 4080
| GACATTTATT | AATTTATTAA | AGGCCAGGCA | TGGTGGTTTA | CACCTGTAAT | CCTAGCACTT | 4140
| TGGGAGGCCA | AGGCAGAAGG | ATCACTTGAG | TCCAGGAGTT | CAAGACCAGC | CTGGGCAACA | 4200
| TAGCAAGACT | CCATCTCTAA | AAAAGTTTT | TAAATTAGCC | ATGTGTGGTG | GCGTGTACCT | 4260
| GTAATTTGCA | GCTGCCCAGG | AGGCTGAGAC | AGGAAGCCCT | TGAGCCCAAG | AGGTTGAGGG | 4320
| TGCAGTGAGC | CATGATCATA | CCACTGTACT | CCAGCCTGGG | TGACCCACCA | AGACTCTGTC | 4380
| TCTTGAAATA | AATAAATAAA | GAAATTTATT | AAGATATTAG | AGTAATATGT | CGGATGTAAA | 4440
| TTTGCCAAAA | CACTTATTGT | AATGAGTCAA | TTTTGTACAA | TTGTTTTGTA | ATGTCATAAT | 4500
| AAGAAAGGAA | GAAATTTTTT | AAAAATGTTA | CAAAGTCAAT | GCTAATTTAA | CTCTGTAACT | 4560
| GCTTATAATC | CTGCAG | | | | | 4576

( 2 ) INFORMATION FOR SEQ ID NO:50:

( i ) SEQUENCE CHARACTERISTICS:
        ( A ) LENGTH: 1618 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:50:

| | | | | | |
|---|---|---|---|---|---|
| GTAGGTTTGT | AAATCAAAGA | TTTTTGGGCA | ATCTGCGTTT | CTGTGTTATG | TTTACCCTTG | 60
| GAGTTGTACA | GGTTTCCTAG | CATCAGTATT | TTGAAGAGCT | CCTGTCATTA | CGGCTATCCA | 120
| GGGTACTTAT | AACTAAGAGT | CAAGCTGCCT | GTAAAATAT | TTTTGGATAA | ACAGTTGCAG | 180
| ATACCACAAA | GTTTAAAGTC | TTAAATGACA | ACTTCAAGAA | GTTTCTGAAA | TATATACTCA | 240
| ACAAGGAGAA | GGCATTTAGA | AACTCAGAGT | TGCGAAGATG | ACATTAAAGC | CGATAATGTT | 300
| TCCTACATTG | GCAAACTTTG | TGCCTGACAC | ATTGTAGGAG | ATCAAAAGA | ATTTGTTGAA | 360
| AGAATCTTAC | TTCAAATTTT | GGTACAGAAG | AATAGTTATG | GTTCTAAAAT | AAAGAAAATG | 420
| AACTTTCATC | TTTTAAACTA | ACAGATATAT | GGAAATGATG | ATTTTGGCAT | TGCATTTAAT | 480
| AGAACTTAGG | TATATAATTT | CTATGAATGA | TAAACAGTTA | CAAGCCCAAA | TTATGATTTA | 540
| CAAAGCAAAT | ATTAAAAGT | ATGTATAGAG | TTAAATAAA | TATTGCTGCT | GCTATTTGAG | 600
| TAATATTGTA | ATAGGATTCT | GGGTGATTCT | CAGTTTGGAG | GTAATTTCAG | TTAAAATTTC | 660
| AGCTTGTCTA | TCAAGGTAGA | TTTTTAAAAT | TAGTGGAGTT | CAGTTGCTCC | TGGTATGGTA | 720
| AATTTAATGT | TCCTCATCTT | CTTTTCTGTT | CTTTCTCTCA | TTTCTATCAT | AACTCCCTTG | 780
| TATATTCCCA | AAAAGCTGCT | TCCTTTCACT | TTTATCTTTT | TTTGGTTTTA | AATTAAAAG | 840
| AATTTTTTTT | TTGGAGACAG | GGTCTCACTC | TGTCACCCAG | GTTGGGATGC | AGTGGTGAAA | 900
| TCACAATTCA | CTGCAGCCTC | AATCTCCTGG | GCTCAGATGA | TCCTCTCATC | TCAGCCTCCC | 960
| AGGTAGCTGG | GACTACAGAC | ATACACCACC | ACACCCAGTT | AATTTTTTG | TATTTTTCAG | 1020
| TATAGATGAG | GTTTCACCAT | GTTTCCTGGG | TTGTCTCAAA | CTCCTGGACT | CAAGCGATGT | 1080

| ACCCACCTTG | GCCTCCCAAA | GTGGATTATA | GGAATGGAGC | CACTATGCCC | AACCTTTACC | 1140 |
| TCTTTTATTT | TTAGTTGATT | TTTTTTCTTT | TGTGCTGAGT | CTAGGGCAAG | AATAAATTGT | 1200 |
| AAACTAGTAT | GAAATACATC | TAATACATTC | AAATTAAAGA | TATAAATATC | TGAACAGTGT | 1260 |
| AATTTTTTAA | AGTGGTGTTT | TTTGTTTAAA | AGTAGACTTA | CTTGCAAAGT | TGTATTTTGT | 1320 |
| GGTTTTTAGA | TCTTAGTATC | CTAAAATTTG | ATTACCTAAA | ATTAAGTTT | TAAGTTTCCC | 1380 |
| TTAACCATCT | CTACATAAAT | AATTGAATAA | CTGAAATCTT | TCGAGTAATG | ATACACTTTA | 1440 |
| CTTCTATTTG | CCATTTTTG | ACAAATTCTT | AGTGTTGAAA | TAGGCCCATA | TATACTGTTT | 1500 |
| CCTATACATT | TGTATGCTAA | GTGGTATACT | GATTATACTC | TATGTTTTAC | ATTTTAGTTT | 1560 |
| ATTACAAATT | GGCTTATTGT | GTGCTGATAT | CTCTGTTTTG | TGATTCTATA | CACCATAG | 1618 |

( 2 ) INFORMATION FOR SEQ ID NO:51:

( i ) SEQUENCE CHARACTERISTICS:
        ( A ) LENGTH: 92 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:51:

| GTTTGTAAGT | AGCAAAGAAA | TAACGTGAAA | ATGTTTTCTG | GAGAAAAACT | TGATTTAACA | 60 |
| TGACGACTTA | AGGATCTCTT | CTTTCATCAT | AG | | | 92 |

( 2 ) INFORMATION FOR SEQ ID NO:52:

( i ) SEQUENCE CHARACTERISTICS:
        ( A ) LENGTH: 889 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:52:

| GTGAGTACTT | CTGTATAAAA | TGTTTTAATA | TTTTAAATTG | TATACTTAGG | AAACTTCAGA | 60 |
| AGTTAGTGTT | TTTATTGTTT | GTACTCTGGA | AACTGAGAAT | ATGTTTTGTG | AGAGAATACA | 120 |
| GGGAAGCAAA | AATTCTGTCA | CCTAAATATA | AGCACACTTT | TTAAATGTGT | TCAAAATTGT | 180 |
| ATGGCTGTCT | CCGAAGTTTC | TTTAAGCTTC | TGGATTATAA | ATTCTGAAAT | AAATTCTCTG | 240 |
| GGAACTATAT | GGGTGAAAAT | TGATGATGTG | TAAGTGTGGA | AAGTCTTCAG | GGGTGCCTAG | 300 |
| AGCAGCTAGA | CAGATAGTTA | AGCTTCTCAC | CGGAAGTTGC | ACCTACCAGC | AGCTGAAACA | 360 |
| CTGTCAGCAA | AAATACTTGT | CCTGTGTGAT | GGATGAGCTT | GGGGATAGCA | GGATTACATG | 420 |
| TGATACTATC | CAGTTTTTGT | TTGTTTTGT | TTTTGAGAT | GGAGTCTCGC | TGTGTCGCCC | 480 |
| AGGCTGGAAT | GCAGTGGCAT | GATCTCGGCT | CACTGCAACC | TCTGCCTCCC | AGGTTCAAGC | 540 |
| GATTCTTCTG | CCTCAGCCTC | CTGAGTAGCT | GTGAATACAG | GCACGTGCCA | CCATGCCCAG | 600 |
| CTAATTTTTG | TATTTTTAGT | AGAGACAGGG | TTTCACCATA | TTGGCCAGGC | TGGTCTCAAA | 660 |
| CTCCTGACTT | CGTGACCACC | TGCCTCAGCC | TCCCAAAGTG | CTGGGATTAC | AGACGGGAGC | 720 |
| TACTGCACCC | AGCTATACTA | TCCAGTTCTT | ATAACTACAA | GTTACCCTAC | CAAAGTTTAA | 780 |
| CTTTCCAAAA | AACTATTAGA | ACTTTTAGTA | AATAAAAAAA | TGAAATAATT | AATTGAAATG | 840 |
| GCAGTTTCTG | TGAGAGAGTA | CATTTTGTCT | GTATTTGTTT | TTCCTATAG | | 889 |

( 2 ) INFORMATION FOR SEQ ID NO:53:

( i ) SEQUENCE CHARACTERISTICS:
        ( A ) LENGTH: 4586 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:53:

```
GTGAGTTTAG  CCATGCCAGA  AGAGTAGAAA  TACCAGGAGC  AGGTAAGCCA  GGGGTTCTTT        60
TTTATTTGGG  TAATTTCATG  TTTGTGTTTT  ACTTGCCTAC  AGTATGAAGG  AGAAAATTCT       120
CATCATACTT  CTCTTAATTG  AAAAAGGTAT  CTCTATGATA  TTTGCTTTGT  TAATATCAAC       180
TTTCATTCAT  TTTAGTGAGG  TCTGAGAAAA  GAAATTAATA  TAAATTTAAA  ACAAATGTGT       240
CATGCTGATA  ATTGTTGGTT  TTAAAAGAT   GGGCCAGTAA  TATATGGTCT  TATATGTAGT       300
GAACATAGTG  TAGGCATTTA  GAAAGTGATA  ATTGACCTGA  CTGGGGCCTT  CATTTAAGAG       360
ACTGGAGTAA  AATGAGGATC  TACAGTCTTT  AAGAAAATTC  TTTCAAACTG  AATTTCAGGA       420
CCACGTGGTA  TTATTTCTAA  CAGACACTTA  GAGTGATGCA  GGCCAAGAGT  TTCCCTCCTG       480
CTATGTGGTG  GAACAGAAAA  CACCAAACTT  CTGGAAAGTG  CCACCAGGGG  AAACACTGGG       540
TAATCCAAGG  GCCAGTTCAC  CTGGATAGTG  AGCTGCTTCA  GACTTGAGAC  TGGTCTGCTT       600
ATTCATTCAA  CAGATATTCC  TAAAGCATTT  TATATGTCAG  GTTGTGTCCT  GGACACTGGA       660
GATAAAGCAG  TGAACAAAAT  AACCACGAGA  ACCCTGTTCT  AAAGAAGCTT  ATATTCCAGT       720
GTGGGGAGAT  GGACAGGAGA  TAAACAAGTA  AATATATAGT  ATGTTGGGTG  ATGATAGATG       780
AAGAAAATAG  AGTAGTAATA  CAAAATATTG  AGGGGAGGGG  AGAATGGGAT  GGCTGGGCTG       840
TGGTAGGTAA  GGTGGTTGGG  AACGGTGTCA  CACACCAGAA  GTAAGTGAGG  AAGCAAGCCA       900
TATGAATAGC  TGGGTAAATG  TATTTGAAGC  TGAGAGCATA  ACAAATGCAA  AGCCATGAGG       960
TTGGAACAGG  ATTAGCTTTT  TGGAGGAACA  GTGAGAATGC  TAGTGTGGTA  GGAATAGAGT      1020
GAGGGAAAAA  GTGGTAAGAA  GTGACGGGAG  GCCAGGTGTG  ATGGCTCATA  CTTGTAATCC      1080
TAGCACATTG  GGAGACTGAG  GCAGAAGACT  GCCTGAGCCC  AGGAGTTCAA  GACTAGTCTG      1140
GGCAACAAAG  TGAGACCCCG  TCTCTACATA  AAATATTAAT  ACAAAAATA   AGCTGGCCAT      1200
GGTTGTGTCC  ACCTGTGGGC  CCAGCTACTT  GCGAGGCTGA  GTTAGGAGGA  TTCGTTGAGC      1260
CCAGGAGTTC  CAGGCTGCAG  TGAGCCGTGA  TCGCGTCACT  GCCCTCCAGC  CTGGGTGACA      1320
GAGCAAGAGC  CTGTCTTTAA  AAAAAAAGAA  AAAAGAAGA   AGAAAAAGAA  ATGCAGGGAA      1380
GAGGGAACAA  GAGAGCCAGA  CAGACCGTGT  AGGCTTTGGA  AGCCATCGTA  AGGACTTTTG      1440
CTTCTGCTCT  GATTGAGGTG  AAAGCCATTA  AGAGGGTTAT  TAAGAGGAGT  GACTGATTTA      1500
CATTTTTAAA  GGTCTTCTGG  GAAAGTGGGA  TTAGAGGCAA  GGGTGGAAGT  AGGGAGTTAA      1560
GAAGCTATTG  GAATGATTCT  GGCAATAGTT  TATGGTGGCT  TGCTTCAGAA  AATGGTTTGT      1620
AGCTGGGCCA  TATTTTGGAG  ATGGCACCCA  CAGGATTTAC  CGAGGGTTTG  TATCTAGGGT      1680
ATGAGAAAAA  GAGAACAGTG  ATGTCTCCAG  TTGGGTGAAT  GATATAAAAG  CTAAAATCCT      1740
GACAAGTGCC  TGTAATGTTG  TAAGTTATCT  GGCCCTGGCT  CTCTCTGAAT  TCATCTACTT      1800
TCCTCCCTCC  TCACCCACTT  ATGCCACATT  AACCTCCTTT  TTTGTTCTTC  AGATATGCCA      1860
GGCATGCCTG  CAACACAAAG  CCTTTGCCTT  TGCAATTCCC  TCTGCCTAAA  CTGTATTGCT      1920
TCAAGAGATT  CATGTGGCTT  CCTTCTCACT  TCATTCTGGT  CTCTGATAAC  CCAACTGCTA      1980
TGTCAATAAT  AACCACAACA  TCCTCCCCAA  CCCTCAGGAC  TTCTTTTCCC  CCTGACTCTG      2040
```

| | | | | | | |
|---|---|---|---|---|---|---|
| CTTGCTAGTG | TTTCTCTTCG | TATTTATCAC | TGTCTGACAG | TAAGTACGGA | CGTACGTACA | 2100 |
| AAAGAATTGT | TTATTACCTG | TCTCCTTGCA | TTAGAATATA | AGCTTCACCA | AGGCTGTGAC | 2160 |
| CAGTGTTGTA | TGCAGCGCTT | GGCACATAGT | AAACATTCGG | GGAACATTTA | CTACTGAAAT | 2220 |
| TTATTAACCA | GGGAACAAGT | CTGGGGGAAC | GGGAATCAAC | AAGTTACGGT | TATTACCATG | 2280 |
| TTAAATTACA | GATGTCTTTT | AAGCATCCTA | CTAGAGAAGT | TGAATACACA | CTTGAGGTAT | 2340 |
| ACAAGACAGG | AGTTCACAGT | TCACACTACA | GGTTAGGGGT | TGTGTATATA | TGTCCTGGGG | 2400 |
| TCATCAGGGT | GGGTACAGAT | AGCCTTTTTT | TTTTTTTTT | TTTTTTTTT | TTTTTTTTT | 2460 |
| TTTTTTTTTG | AGATGGATCT | CGCTCTTCAC | CCAGGGTGGA | GTGCAGTGGT | GCAATCTTGG | 2520 |
| CTGCAGCTGT | GACCTGTGCC | ACGGTGGGTT | GCAAGGGATT | CTCCTGCCTC | AGCGTCGTGA | 2580 |
| GTAGCTGGGA | TTACAGGTGC | CTGCCACCAT | GCCCAGCTAA | TTTTTGTGA | TTTTGAGTA | 2640 |
| GAAACGGCAT | TTCACCATCT | TGGCTAGTCT | GATCTTGACT | CCTGCCCTCA | TGATCTTCCC | 2700 |
| ACCTCGACTT | CCTGAAGTGC | TGGGATTATA | GGCGTGAGCC | ACCATACCCA | GCCGTAGATG | 2760 |
| GCTGTTAAAG | CTATAAAATG | AGGAGGGATT | ACTTAGAGGT | ATGAATTGAG | AGAGAATACA | 2820 |
| AGAGGTCTAA | GGACAAAGCT | CAGGGTCACT | CCAAATTTTG | TAAGTCTTCA | TTTGGAGATG | 2880 |
| GAACATCCTA | ATATTTTAA | GATACCGACT | TAATATTTGC | ACCCAAGTTA | AAGATCCTCT | 2940 |
| TGATCAGAAT | GAACAGGAAG | CTTTAAGCTA | AGCACAGTGC | TACCAAGAAG | CACCATGTTG | 3000 |
| ACCTTGAGGA | CTCTGGCAGG | AAGCTGTTTG | TGGTTGTCAC | ACCTAGTTTC | CTCTGTGAAA | 3060 |
| CTACTGCTGC | CTGTGGGTGA | TGTGGTTATA | TGCTGCTGGC | TGCTGTTGAT | TCTCCTGTTT | 3120 |
| GTGTACAAGG | TGTTTTTCCC | TCCCAGTACC | TCCCAATGTA | GGCATCGGTT | CATGCACAGT | 3180 |
| GAAGTAGTTG | CCTGCGAGAA | ACCTTGTAAG | GCAGGGAGCA | GCCTTTGAA | TGCAATAATC | 3240 |
| TACCCGAATC | ATTTTAATGA | CTTAATTATA | GAATGAATTT | CTTTGAGACA | AAGTGAAAGT | 3300 |
| CTTAGTTGTA | TTACACTTTT | AGACATAGAG | GAGACATGTA | GGTTTGTTTC | TGTATACAGT | 3360 |
| AAATTTCTGT | GCTTTTCTAT | ATCTTATGAA | ACTTGAATAG | TTGGCTCTGT | TGCCAGGTGA | 3420 |
| AAGTTTTGCT | AGGTTTTTA | GGAAATTAGG | ATGAGTACAT | TTAAGACACA | GGGAAATTTT | 3480 |
| ATCTTGAATA | GTAAAAGACA | TTGTTAAGCT | ATCGATTCCT | TTCAGAGTTT | ATTTGGAAAA | 3540 |
| TCAGAGAGAT | GTTTTACTGG | CTCCTTTGAC | ACCAAGTCAC | ATCTTCTCCT | AATTTATTGT | 3600 |
| GAAGAATGTT | GACATTAACT | TATTTCTCTG | AAGACCTGTC | TACCTTAGGG | GGCTGTTCTG | 3660 |
| CATCAAGTTG | CCTTTTTAGG | GGATGTACAA | CTTATTATCT | GTCTCTGAAG | CAAATATGAA | 3720 |
| TATTTGGATG | GTGGGTGTAT | TAATTCATTT | TAACACTGCT | GATAAAGACA | TGCCCCAAAC | 3780 |
| TGGGGAACAA | AAAGAGGTTT | AATTGGACTT | TACAGTTCCA | CATGACTGGG | GAGTCCTCAG | 3840 |
| AATCATGGTG | TGAGACGAAA | GGCACTTCTT | AGGTGGCGGT | GGCAAGAGAA | AAATGAGGCA | 3900 |
| GAAGCAAAAG | TGGAAACCCC | TGATAAGACC | GTCAGATCTC | GCGAGACGTA | TTCACTATCA | 3960 |
| CAAGAATAGG | ACGGGAAAGA | CTGGCCTCCA | TAATTCAATT | ACCTCCCACT | GGGTGCCTCA | 4020 |
| CACAGCACAT | GGGAATTCTG | GGAAAAACAA | TTCAATGGGA | GGCTTCGATG | CAGACATAGC | 4080 |
| CAAACCATAT | CAGTAGGCTT | TTGTTAAATC | ATGGATTTTT | TTTGGAACCA | AATTTAATCA | 4140 |
| CAATTTTCTT | TTATCTTTGA | GTGTCTCCCA | AAATAGCAGT | AGATGGGAAT | TGTGAAATTC | 4200 |
| TGTTTCTCAG | AGCTGAGAAT | AATCTTAATT | TTTCAGGTGA | GCAGAATGCT | TATCTTTGCC | 4260 |
| TCCGAGCATA | AGTTTTACAA | GAGGGTATGT | AGGGAGCTGT | ACCTTATTTT | AGAGTTTTAA | 4320 |
| CTTTTAAGAG | ACAAACTTTT | AGTTAGCTAA | AATACAAATT | ATTCTTTCAC | ACCTTCGTCT | 4380 |
| TCACATGGAT | ATTGGCGGCT | CTTAATGCTG | TTATGTTTAA | ATTCCAAAGA | ATGGTGACAT | 4440 |

```
TTGAGTCACT  AAAATTTATT  GATATTGTAA  AGATAAAGTC  TATCTGGCTT  GAAGTCCCAT   4500

TTGTGAAGTG  AATTAAAGTC  TTTCTGGCCT  AAAATAATGT  TCTTTAAAAA  ATGTTTATTA   4560

ATTCTGTGTA  ATTTTTTTTT  CTTTAG                                           4586
```

( 2 ) INFORMATION FOR SEQ ID NO:54:

( i ) SEQUENCE CHARACTERISTICS:
        ( A ) LENGTH: 2127 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:54:

```
GTTAGTTTGA  GCCCTGTCTG  CTTTCTAAGA  TTTGGTTATT  GACCATTTTC  CAATTTCCTA     60

TTCTTTCATT  ATTAATGCCT  TAATTCACCC  ATGAATAATT  TTTTATCAAT  TGTATACTCA    120

GTCCTGTTGT  GAGTCTATAG  AGGACCTAGC  AATAAGATGT  ATAAGTGGAA  GATCTTCTTT    180

CCTTAGATTT  CTTTAATATA  ATACAAGACA  CAGTAACTAA  TAACACCAGA  CAGTGTAGAG    240

TAAAACACAA  AAGTGTCTTA  TTGCCAACTG  TTCTTTCAAG  ATTTCAGGGA  GTGGTGACGT    300

GGCGGCGGGG  GGAAGCTCAG  TGATGATGGG  AATAATTGTC  AAAGGACTTT  ATGAAGAGGG    360

TTGACCTGAG  GTAAGTTCTG  AAGGGTGACT  CAGATTTGCC  AAGATTAATA  GAGTTCCACA    420

TGTTCATAAA  GCAGGACAAA  AACCACTGTA  ACTTTTGTAA  GCTCTATAAA  ACATCCTTAT    480

CCTGGAAAGG  AAGTTGACTG  CATTTAGCTC  CTTTGATCTC  CCTGAGACTG  GTAGGAATAT    540

CATTGAGTTT  TAATTAAAAG  CCCAGTAGGC  TGAATCTCAT  CATCTTATGC  ATAACCTTTG    600

GCAAGTTGAT  TTGAAAAGCT  ACCTCCAAGG  TCCCTCTCAG  TCCTAAAACC  TTATGATATG    660

ATAACGTTGA  CCCAAAAGGA  CCCCATTTCT  TTTCTGATGA  TGGTATATCA  AGAAGACCCT    720

ATATGTACAC  ATAAGTAATT  TCCCACTCAT  AGCCAGGCTT  CTTAAATGCC  AACTACTTTT    780

CCTTTAACAT  TTCAGTGAAG  TCTGCTTTAT  TCATAAACTT  GATTGTGATT  TATACTCAAC    840

AAGTTATATC  TCTGTGGCCT  CTTCCTGAGT  CATGTTTTTC  AGATGCACCT  TGTTTGGCTT    900

GAATTTAGAA  GCATTTCGTA  AATACATTTC  AGAAGCCATC  TTAATCTCTG  TGTCTTCCAG    960

ATCGCTTTAC  AGTTTCTAAC  TAGGCATAAC  AGCATTTTAA  ATCTTAGGGA  CCATTAGTGG   1020

GGTTAAATAA  TTATTACCAG  TAAATACTAG  GTAAAATAAA  GGGTGCTATT  TTTGCTGAAA   1080

GGTATGTGTG  CGTGTGTTCC  CAGAAAAATT  CTGCTTGTAT  ATGTATTCAG  TAGTTATCTC   1140

TAGCAGGACT  GTAATTGATT  TCTATTCTCT  TTATAATTTT  TTAAACTTGC  TTCATTTTCA   1200

CAAAGAATAT  GTATATAATT  ATATATATAT  TTGTGATCAA  GATAAAAACA  GTTGTTACAA   1260

AAAGCTTACA  TGGTGATAAT  TTGTATAATG  CTTCTGGATT  GAACATATAT  TGCTCCCTAA   1320

TAATAGAAAG  ACTGAAGTAA  ACCTCGTTGG  CGGGAAAAAA  ATGTAGAATG  CCAGGAACAG   1380

TTTATGTGAG  TCTGTAGTAT  GGGTTTTACA  CCCCTTCATT  CTATTTCTT   CCAGGTGTTC   1440

TTAATGGGAG  TTTTACTGTC  CTCTAGGAA   ATAGTTAAGG  GCAAGTTTGG  GATAATCAGT   1500

GACTGGGGAT  GTGTAGGACA  GGTGGGGGAC  AGTCATAGAT  ATCGAATGGG  CCCAGGCCAA   1560

GGTTGCTAAA  CTTCCTGCAC  TGAAAGGTGT  ATCCCCGGCC  GGGCGAAGTG  GTTCATTCCT   1620

GTAATCCTAA  CACTTTGGGA  GCCTGAGGCA  AGTGGATCAC  TTGAGGCCAG  GAGTTCGAGA   1680

CCAGCCTGGC  CAACATGGTG  AAACCCCATC  TCTACTGAAA  ATACAAAAAT  TAGCTGGGCG   1740

TGGTGGCAGG  TGCCTGCAGT  TCCAGCTACT  TTGGAGGCTG  AGGCAGGAGA  ATCACTTGAA   1800

CCTGGGAGGT  GGAGGTTGCA  GTGAGCCAAG  ACTGCATCAC  TGCATTCCAT  CCTGGGTGAA   1860
```

| | | | | | |
|---|---|---|---|---|---|
|AGAGCGAGAC|TCTGTCTCAA|AAAAAATATA|TATATATAAA|AATAAAGGT|GTAGCTCCCA|1920|
|CAAGAAAAGT|TTTTTTTTTT|TCATTCAAAC|TGGTAATACC|ACCACCTTTG|AAAAGGAAGT|1980|
|ATGGGATCTC|TTGGATTAAT|TTGGGAAGTG|TATAGTTTCT|GTTCAGAGTG|TTTTATATTT|2040|
|ACATGTTAGT|GAAATTATAG|AGACATTTTA|TCCCCTTGTG|ACTTGACAAG|ACCTTTAAAT|2100|
|TATGTTATTT|CTCATTACCT|TTTTTAG| | | |2127|

( 2 ) INFORMATION FOR SEQ ID NO:55:

( i ) SEQUENCE CHARACTERISTICS:
        ( A ) LENGTH: 716 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:55:

| | | | | | |
|---|---|---|---|---|---|
|GTAATTGTGC|TAAAGGTAAG|GTTAACATT|GTTATTCTGC|TTCCATGTTT|GAAGTTTAAC|60|
|TAAATGGAGT|CATTTCTTAC|TAACTAAGAA|AGATGAGGAA|AAGATTTATG|ACTTTAGACT|120|
|GGAGGCATGG|ATATGGCTGT|CCAATTTTTC|TGGTCAACCA|ACTGATTTCT|GAGCCCTTCT|180|
|CAGTAAGATA|GAAATTTTAG|AATGGTATCT|TTATTATATT|GGACTACTGA|TGCTTCCCTA|240|
|TCTGCAAATC|TTTAGGTTTC|CCTTGTAAAC|TGGAAATTAA|ATAGAAGTGT|AGTGATTCTT|300|
|CAACATATTG|AGAATAAGGA|CAGGAGATAT|CACTGTTATG|GGCGGAAACC|TGGGCTAGGA|360|
|ATTGTTTGCT|GTCAGGAATT|GGAACTAAGT|AGGTGTGGAC|TAGTAAGCCA|ATTACATACC|420|
|TCTTAGCATT|GGTCTGTTTT|GTTCCAACAT|AGAGGAAAAA|AAGGGTGTT|AGTCTTAAAT|480|
|GATATTACAG|TTCCTTATGT|GCCAATTTCA|TTAATAATT|TTAGAAAAAT|GTGACTGTTA|540|
|CCATGAAGAA|AATTAAGGTA|TCTTAGGGAT|AATTAAAACA|CCAATCATAA|GAAGTGTGCA|600|
|TATCTAAAGT|ATTGGGTTGG|TTTTGAATTT|TATTTGTGA|GTAAAGGAGG|AGGAATGGGC|660|
|CTTTATTTC|TTTGTGTTCC|AATTTGTGG|GGGTTTTTT|TTTATTATTT|CTACAG|716|

( 2 ) INFORMATION FOR SEQ ID NO:56:

( i ) SEQUENCE CHARACTERISTICS:
        ( A ) LENGTH: 837 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:56:

| | | | | | |
|---|---|---|---|---|---|
|GTGAGTAAAA|TAACCAATGT|ATTGATCAGC|ACAATGAAAC|ATAATTCCT|TCCTGCCCTA|60|
|TTCTGTGGGT|TGTTTCCTTA|CTTTATATAT|AGTCTCCTTT|CATACACAAA|AGTTTTAAT|120|
|TTTGATGAAA|TCCAATATAT|TTTTTCACTA|GTTGCCTGTG|CTTTCGTTTC|ATGTATGTAT|180|
|GTATGTATGT|ATTTACCTAT|TCGAGATGGA|GTCTCGCGCT|GTCGCCAAGG|CTGGAGTGTA|240|
|GTGGCACGAT|CTCGGCTCAA|TGCAACCTCC|GCCTCCTGGG|TTCAAGCAAT|TCTCCTGCCT|300|
|CAGCCTCCCA|AATAGCTGGG|ATTATAGGCA|TGTGCCACCA|TGCCCAGCTC|ATTTCTGTCT|360|
|TTTTCGTAGA|GATGGCGTTT|AGTCATGTTG|GGCAGGATGT|TCTCGAACTC|CAGACCTCAT|420|
|GTGGACCACA|TTCCTTGTGC|TCCCAGAGTG|CTAGTATTAC|AGCTGTGAGC|CACCCATGCC|480|
|TTGCCTGTTG|CCTGTGCCTT|TGGCTCTTCA|ATAACTTTTA|TTTATAACAT|CTTTGCCCTG|540|
|TCATTGTTCT|TCTAAGCATC|AGTGTGTGTG|TATTTTGGTT|AGAGATGTAA|TCTCTTTTAA|600|

| | | | | | | |
|---|---|---|---|---|---|---|
| GATACATTTT | ATATAGGTAA | GGTTTTAAAA | TTCTCATACA | TTCCTTTTAT | ATATTCCTC | 660 |
| TACTAAAAAA | TGGGCTTTAT | TTATATAATT | AAGAAAGGTT | TTGTAAGAAA | ATAAGGACAC | 720 |
| ACTTTGCACT | CACTCAGAAA | ATGAGACTTT | CTTGGTATT | TTCACTTAAG | TTGCACTGGG | 780 |
| TATGAAATGA | CTTTTTAGAC | TAAGTAGATG | TTTCTAATGC | TGTACTTTAT | TTTATAG | 837 |

(2) INFORMATION FOR SEQ ID NO:57:

(i) SEQUENCE CHARACTERISTICS:
        (A) LENGTH: 1081 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:57:

| | | | | | | |
|---|---|---|---|---|---|---|
| GTATTTCCCA | AAAAATATGA | TACTAATGGG | GATATTGTAG | ATGAGACCAA | CTTCCTGTTG | 60 |
| TTAGTCATTT | AGTTCAAGTT | AACATCTAAG | AACATTTATT | CTGTTTCTAT | TTACATAGTT | 120 |
| AATCTCTACT | TGTGGAGTAG | AAAAGAAATA | GAATCTTAAG | ACCTATGTAA | ATTCTTTTAA | 180 |
| TATTGTATGA | AAGATCTATT | TTGGGTAAAA | GCTTCGATTC | CTCTCTATCT | AATAAAGTT | 240 |
| TTTAGAATAC | TGTGATTTTT | ATGAGCTGAG | AAGGCTTAAA | AAAAGTAGCA | CACATGTCAC | 300 |
| TAGCTAATCT | TGTATAGCAG | CCTTTCCTTA | TCTTATGAAA | ATTAAATACC | ATTGAAAATG | 360 |
| TCAGAAAAAA | AATAAAAAGT | TGTCTTTCAT | GTGTTACAGA | GAGGCATAGA | GTTAAAAGCA | 420 |
| TTGATTTGGT | AGCTAGTTCT | TCCCCCTCCG | GAGATGGAGT | CTTGCTCTGT | CGCCCAGCGT | 480 |
| GGAGTGCAGT | GGCGCCATCT | CAGCTCACAG | AAAGCTCCAC | CTCCTGGGTT | CACGCCATTC | 540 |
| TCCTGCCTCA | GCCTGCCGAG | TAGCTGGGAC | TACAGGCGGC | CGCCACCACA | CCCGGCTAAT | 600 |
| TTTTTGTATT | TTTAGCAGAG | ACGGGGTCTA | CACCGTGTTA | GCCAGGATGG | TACTCGATCT | 660 |
| CCTGACCTCG | TGATCCTGCC | CGCCACGGCC | CCCCAGAGTG | CTGGGATTAC | AGGCTGGTAG | 720 |
| CTATTTCCTT | GATACTGACT | TAGCATATGA | GTTTATGCTT | AACTCTCATA | AGATAGACGA | 780 |
| AACTAATTTT | TATAGTGGCA | TAGATTAAAT | GTTAGAGAT | TTTTATATGA | AATTTTAAGA | 840 |
| GTAATGTTTT | TCAACCTCAA | TGTACAAAAC | ATGTATTTTA | TTAAAAAATT | TTGAAATACA | 900 |
| TCACAATGTA | AACCATTTTA | TATAATTCAT | AGTTTGAACT | ATAATTATTT | ACAAAGACAG | 960 |
| TAAAAGGAAG | AGCGGCTGTT | TCAAAATAAT | ACTTCAACTT | GTAATTTTGA | CTAATTTCTT | 1020 |
| GTCTAAATAT | TTAAAAAATA | TTTAATAATT | ATTCAGTGAA | CCAAGACATT | TTTTATTTCA | 1080 |
| G | | | | | | 1081 |

(2) INFORMATION FOR SEQ ID NO:58:

(i) SEQUENCE CHARACTERISTICS:
        (A) LENGTH: 1455 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:58:

| | | | | | | |
|---|---|---|---|---|---|---|
| GTGAAAATCA | ACATCTTTTT | ATGAGAAAAA | TACATCAATA | TCTAATCTAT | TAATAATCCT | 60 |
| TTTGGGGATG | GGAGGGTGGC | AGTTAGGTTT | AATATGTTAT | AATTACACCT | TGTTATGAGA | 120 |
| AAAATCTTGG | ACTGTAACGT | CCCTCTCTAC | CCACAAATTG | GGAAGGTGCC | AAGAGACCAA | 180 |
| AGAATGACTC | AGACAAGTCC | AGCTCGGCAA | GTACATAACG | TCTATTAAGA | CTTACATATG | 240 |

| | | | | | | |
|---|---|---|---|---|---|---|
| GAGGAGGCAG | AGGTGGTGGG | GAAAAATAAA | AGACTTATAT | ACAGGGTACT | CCTAGGTAGC | 300 |
| AGCAGGACAG | CTCTAGAGAT | CCTCGCTACC | TCCCATCGCT | AAGCTGCTTT | TAAGCTAATT | 360 |
| TTCTGGCTCT | TTGCCTACTA | TGTGTGTGCA | CGATGGGACT | GTTTTCCTTG | GTAGTTTCTC | 420 |
| AGATCTTCTC | TGGGATGTTG | GGGTTCTCAG | GGACACCTGT | TCCTTGGCTG | GCACCATGG | 480 |
| CCTTGGCTCA | CTGCCTAGCC | TTCAGGGTTT | AGGCAGCAGA | CATACACCCT | TAAGTAAGGT | 540 |
| AGGTGACCTG | TCACATTTCA | CCCCATGTCA | AAGAGGAAAC | GAGTCAGATA | ATTTGTGGTT | 600 |
| GCCCTAAGAT | TTTGGTGACA | GAGTAAAAAT | TCAGTGTTCT | TTCTTGATTT | CCTTACCAAG | 660 |
| TTTCTTTCCC | ATAGAGCAGT | GGTCCATCCT | TTTTGGCACC | AAGGACCAGT | TTCATGGAAG | 720 |
| ACAATTTTTC | CATGGACAGG | GTTGGGGGTT | GGAGAGATTT | TGGGATGATT | CATCTGCCTT | 780 |
| ACATTTATTG | CACACTTTAT | TTCTATTATT | ATTACGTGGT | AATATATAAT | GAAATAATTA | 840 |
| TACAACTCAC | CAAAATGTAG | AGTCAGTGGG | AGCCCTGAGC | TTGTTTTCCT | GCAACTAGAT | 900 |
| GGTCCCATCT | GGGGGCGGTG | GGAGACAGTG | ACAGATCAGC | AGGCATTAGA | TTCTCATAAG | 960 |
| GAGCATGCAA | CCTAGATCCC | TTATGTGTGC | AGTTCACAAT | AGGGTTCACA | CTCCTGTGAG | 1020 |
| AATCTAATGC | CACCACTAAT | CTGACAGGAG | GCCAGCACAG | GCGGCAATGT | GAGCGATGGG | 1080 |
| GAGCAGCTTT | ACATACAGAT | GAAGCTTTGC | TCGGATGCTC | ACTGCCTGCT | GCTCACCTCC | 1140 |
| TGCTATGTTG | CCCAGTTCCT | AACAGGGTCC | ATGGCCCAGG | GGTTGGGGAC | TCCTGCTTTA | 1200 |
| GAGTGGTTGA | TATTCAAACT | CCTCTCCAAA | CCAGTCAATG | AAGTTTGACT | CATATTTAGT | 1260 |
| ATCCAATTAC | AAGGTTTTGA | ATTTTTTGAC | TGCCAAAAGT | TTTTTTTTA | ACTTTATTAT | 1320 |
| TAAAATGGGA | AAGACAGCTG | ATTTTATTTA | GATGGAATAA | TTGTTAAGAT | ACTTCTTCTG | 1380 |
| CCTTAGATTA | CTATTGTATT | TGTAATTAAA | GTGCTCGTTT | GGATACTGGC | ATTCTGTGTA | 1440 |
| ACCAATTCTT | CATAG | | | | | 1455 |

(2) INFORMATION FOR SEQ ID NO:59:

(i) SEQUENCE CHARACTERISTICS:
    (A) LENGTH: 2741 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:59:

| | | | | | | |
|---|---|---|---|---|---|---|
| GTAAGTTTAA | CAATACTAGG | AGAATATCTT | GGGGCTTACT | ATCTGGAAAT | TTAAATTTCA | 60 |
| TCTAACCCTA | CAAGTGAAGT | TAATAGGGTA | TACATAGAAG | AAAATATTCT | ATGCATTTTG | 120 |
| GTACCCATGG | ATCACTTAAA | AGAAGGGCCT | TTAAAGACTA | AGAACACAGG | AAAATGCATG | 180 |
| ATATAACAGG | TATCTTTTAA | AAAGGATAGA | CTGCTTTATT | TATTTATTTA | TTTATTGAGA | 240 |
| CAGAGTCTTG | CTCTGTCACT | CAAGCTGGAG | TGCAGTGGCC | CAATCTCAGC | TCACTGCAAC | 300 |
| CTCTGCCTGC | CGGGTTCAAG | CGATTCTCAT | GCCTCAGCCT | CCTGAGTAGC | TGGGACTACA | 360 |
| GGCATGCGCC | ACCACGCCTA | GCTAATTTTT | GTATTTTTAG | TAGAGAAGGG | GTTTTGCCAT | 420 |
| ATTGGCCAGG | CTGGCCTTGA | ACTCCTGACC | TCAAGTGATC | CGTCTACCTC | GTTCTCCCAA | 480 |
| AGTGTTGGAA | TTACAGGCAT | GGGCACCGTG | CCCGGCTGAC | TGCTGTATAT | TTAATATGAT | 540 |
| CCCTATTTTT | AAAGTGTATG | TTTATTTATG | AGCATACAAA | ATAGTGGAAA | TGGAAAAACC | 600 |
| AAACTGTTAA | GATCATTGTT | GGGTGAATGA | ATTCCTGGTG | ATTTCTGTAA | AATTTTTAAG | 660 |
| GCAAATACAT | ATTACTTTTA | AAATCAGAAA | TAGAAAAGCC | TTCTTAAAGA | TAGAGCTGCA | 720 |

| | | | | | | |
|---|---|---|---|---|---|---|
| TGATCCAGTT | AGGTATAGAC | AAGCCAGTGA | GTTAAGACAA | CTGAGTATGT | TCCACTTTGT | 780 |
| TGAGCTGTGC | TACCCTAGTT | AATGTGACAT | TAGTGCTGGC | CCAAGAAATA | CAGAAAAGGG | 840 |
| CAGTTTTGCT | ATCTATCTGG | TTTATATTTT | TTAGGCAGCT | GCTTAGAAGA | TCTGCAAGGT | 900 |
| GAAAGGTTTT | AGTTTACATA | TGTGAGATAG | AACTACTTTT | TTAAAGAGCA | ATTCAGTAAA | 960 |
| TCCAGAGAGT | TCTAAATCCT | TGGATCCAAT | TAAAAGAATA | TTGTTATTTG | TAGATCAGTT | 1020 |
| TTATAATGTA | ATTGATAAGA | ACTGGCTATA | GAAGGAATAC | CAGTTTTAAA | GTCAGGATTC | 1080 |
| ACTCTAGGCT | GGGCATGGTG | GCTCATGCCT | GTAATCCCAG | CACTGTGGGA | GACCTAGTGG | 1140 |
| GGAGGATCAC | TTGAGCCCCG | GAGTTCAAGA | CCATCCTGGG | CAACATAGCA | AGATACCATC | 1200 |
| TCTACCCCCA | ACCCCCCCAA | AAAAATCACT | CTAAGTGTAT | ACTTAATACA | CATGGATGAT | 1260 |
| CCTTATGAAA | AGTCCTCATT | TTTGAAAGAT | CTGAGAGCTG | GTCTTCTTA | GTCTATTTTT | 1320 |
| GTAGAATTTT | CCGTTCCCTA | ATCTACAGAT | TAGGAAGACT | TGACGTTAAC | TTCATTTTCA | 1380 |
| ATGTCTTACC | ACTTGCTCAG | TTTTCCTGAG | ATCTCTTGAT | ATTTATGGA | GGAGAAATGA | 1440 |
| TCATAATCTA | TTCTTTGCTG | ATTCTGCAGC | TTTGTACCAA | ATACAAACTC | AGTAAGTTTA | 1500 |
| TTTACTTTTG | TATCATCTGG | AAATAGAAAT | GTTAAGCCAC | AGTTTGTTAG | GATTACTCC | 1560 |
| TATCAGTACT | TCTTACAAAC | TTTGCTATGT | ATATTTTAAA | TTTTAAAAAC | ACTCTGATGC | 1620 |
| ACAGCTCTTA | GAAGTGGACA | CAGAAGAAGG | AAGAAATGCT | TCTCAAAAAT | TCAGACATTG | 1680 |
| GTGTGAATAC | TTAAAAATAG | ACTAAGCCAT | AATGGGTTGT | GTACCACTGA | ATCATACACT | 1740 |
| TAAAAATGGT | TGAATGGTAA | ATTTTATGTT | ATATATATAA | CCACAATTTT | AAAAAACTAG | 1800 |
| CCTGTAATAC | CAGCATTTTG | GGAGGCCAAG | GCGGGTGGAT | CACCTGAGGT | CAGGAGTTCG | 1860 |
| AGACCAGCCT | GGCCAACATG | GTGACCTCAT | CTCTACTAGG | GAGGCGGAAA | GTAGCCATGC | 1920 |
| CGTGTGGCAT | ATGCCTCTAA | TCCCAGTTAC | TTGGGAGGCT | GAGGCGCAAG | AATCACTTAA | 1980 |
| ACCCAGGAGG | CAGAGGTTGT | AGTGAACCGA | GATCAGGCTA | CTGCACTCCA | GCCTGGGTGA | 2040 |
| TAGAGTAAGA | CTCTGTCAAA | AAATAAATAG | TAACAATTTG | CCCCAAACCA | TTGAATTGTA | 2100 |
| TAATTTAAGT | AGATGAAATT | TATGGTATAT | AAACTGTTTT | AAAAAAATAA | ATTATGCTTA | 2160 |
| ACTGAATCCA | AATCATGCAT | GTCCACCTTG | CTTAAGAACA | TTATTGAGTT | TTAATAATTT | 2220 |
| TTTATATGTG | GAAAAAGACA | GAGATCCAAA | TTGATAAAAC | CGGTGGCGGC | GGAATGCTCC | 2280 |
| TAGATGACAT | ACTACCAATC | AGGTCCCCTT | ATCAAGTAGT | GGCTCTGTAG | TAAAATCACA | 2340 |
| TCTTACATGA | GTGGTAGGTA | GAAAGTGGAT | ATGATAGAAA | ATATTATAGA | AAAATATAAT | 2400 |
| ATAGAAAAAT | AGGGTAATTC | CTTAAATTGC | CCCTAAATCA | TGAAGGTTCT | TTAGTAGTGG | 2460 |
| AAGACAGAGT | CAGGTCTGAT | TTGGGAAAGG | GGGCGTGGAG | AAAGGAACAC | TGCAAGACAC | 2520 |
| AAAATTCCGT | TTTAAAATTT | TGCTCTCAGT | AGTGTTCACT | GAACACGAAT | GAAAGTTCAC | 2580 |
| TAATGAATAT | AGGTAAGATT | AGACTTCTGT | AATTCTTGTT | TGCTTTTGA | ATTATGAAGT | 2640 |
| ATTTCAAACA | CTGTAGTTAT | TTTTTAACAT | AAGAGCTTGG | ACGGAAGTCA | GATCTGAGTC | 2700 |
| TCCTTGAGTT | AAATGCTTTG | TTTGATTTGT | TTTGACCCTA | G | | 2741 |

( 2 ) INFORMATION FOR SEQ ID NO:60:

( i ) SEQUENCE CHARACTERISTICS:
        ( A ) LENGTH: 197 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:60:

| GTAAGGAAGG | CAGAGTTGGA | TATTGAGTTC | CTTCTCTGTG | GCATGTATTG | AAAAGTTACC | 60 |
| GAGGTTTGG | CTAGAGTGAC | ATAGGGACA | GAGGAGTGAT | GGGGAGAGAG | GGTTTGGGAG | 120 |
| AGCAGAAATT | GTAAACCTCT | GCCCGGAGAA | CCTCTTATTA | TCAACATTTT | CTTCATGCTT | 180 |
| TTTTTCTCTG | TCACTAG | | | | | 197 |

( 2 ) INFORMATION FOR SEQ ID NO:61:

( i ) SEQUENCE CHARACTERISTICS:
        ( A ) LENGTH: 82 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:61:

| GTAATTTTTC | ACATACCTTA | TCAGAGCATG | AGCTTGGGAA | ATACAAGTGT | TAAACAAAGT | 60 |
| TTGAAATGTT | TTTATCTCCT | AG | | | | 82 |

( 2 ) INFORMATION FOR SEQ ID NO:62:

( i ) SEQUENCE CHARACTERISTICS:
        ( A ) LENGTH: 1079 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:62:

| GTGAGTACCA | TTTGGAATTG | TAAAGGCAAA | GATAGGTCTT | CATTACTGAG | TAACATTTTT | 60 |
| TAACCACTGT | CTTGAGATAC | AGTTTACATG | CTCTATAATT | CACCTATTTA | AAATGCACAA | 120 |
| CTAAATGGGT | CTTAGTATAT | TCACAGATAT | GTGCAATACT | CACCACAATT | TTAGAACATA | 180 |
| ATATCCCATT | GTATAGTTAT | ATGAGAGTAT | TTTTATCCAT | TCATTAGCTA | ATGTATATTT | 240 |
| CAGTTGTTTC | TACTTGGGGC | ATATATGCAT | AATACCACTA | TTAGCATTTG | TGTTTGGGTT | 300 |
| TTGGTATAGA | CATGTATTTT | CATTTCTCTA | GGGTATATAC | CTAGGAATGG | CTGCTGGGT | 360 |
| CATACATTAA | CTGTGTTTTA | CCTATTTAGG | GAATTGCTAG | ATTGGTTCTC | CAAAGTACTG | 420 |
| TACCATCTTA | CACTTACACA | GCAGTATAAT | AAAGATTTTA | GTTTCTCCAC | TATCTCATTA | 480 |
| ACACTTACTA | TCTTACTTTG | TTTAAATAAC | TTATTGAGGA | GAAATTCACA | TAACATAAAA | 540 |
| TTAATTGGGT | TTTTCTTTTC | TTTTGGGAGA | TGTTGTTTCA | TTCTTGTCAC | CCAGGCTGGA | 600 |
| GTGCAGTGGT | GCATCTCAGC | TCACTGCAAC | CTCTGCCTCC | CAGGTTCAAG | CGATTCTCCT | 660 |
| GTCGTAGCCT | CCCGAGTAGC | TGGGATTACA | GCCATGTGCC | ACCACGCCTG | GCTAATTTGG | 720 |
| GGATTTTTAG | TAGAGATGGG | GTTGACCATG | TTGGCCAGGC | AGGTCTCAAA | CTCCTGACCT | 780 |
| CAGGTGATCT | GCCCACCTCG | GTCTCCCAAA | GTGCTGGGAT | TACAGGTGTG | AACCACCGCA | 840 |
| CCTGGCCTCT | AAGTCTTGAT | TCACATACTA | TAGACTCCTA | TTGTTTTTAT | TGAATTTTAA | 900 |
| TAGATATTCT | TGAATCGATG | TATCTTCATT | TGCTATATGC | CGTTAATACC | ATTTCCAGAG | 960 |
| ACTTTAAATA | GCTTTTATAT | AATTTTCACC | CCTTTTACTG | GGCAGCAGGT | TCACAGAGCT | 1020 |
| CCTCACACTA | TTATGGTGGT | AGTTGCTATG | TCTCTCAGAG | CACTCTTGCT | GTTTGCCAG | 1079 |

( 2 ) INFORMATION FOR SEQ ID NO:63:

( i ) SEQUENCE CHARACTERISTICS:
        ( A ) LENGTH: 659 base pairs (B) TYPE: nucleic acid
(C) STRANDEDNESS: double
(D) TOPOLOGY: linear (i i) MOLECULE TYPE: DNA (genomic)

(x i) SEQUENCE DESCRIPTION: SEQ ID NO:63:

| | | | | | | |
|---|---|---|---|---|---|---|
| GTAACTACAT | TTTCTCTATG | GGCTGCAAAA | TAAAGCTTAT | AGTCTGTGAT | GAATACAAAA | 60 |
| AATTACCCAT | AGTTGACTCT | GTGGCCTTTT | TTCCAAGATA | AACACCTGGG | ACTCTACTTA | 120 |
| AGGAAGTTTC | TACTTTAATC | TTTATTCTTG | ATGTCACATG | TTGATTAAGG | TCTCTTTTCC | 180 |
| TCAAAAGGCA | ACAATGTTAA | ATATTTCATT | GCCTTCTTAA | TTCAGAAAAA | TCACAAGATA | 240 |
| GGAATTAAGA | AGTTACTTGG | TTTCTATGTC | ACCTTTCATT | CTGGTTTAGT | AAACATACTG | 300 |
| TAGGTTTAAC | CAAGAGAATG | TCACATGGAA | ATTTAAAACC | CACTTCGACT | TTATTACCAT | 360 |
| TCATCTCTGA | GAGGCAAATC | GGCCAGATCT | GTGTATCTTA | CTTAGAATGA | CTTGACATTA | 420 |
| TGGTTGGGTG | CTGTCACTGC | AGTGTAGTAC | TGCAGGTAGT | ACTTGGCATG | TGATGCTAGA | 480 |
| TGGGCTCTGA | TTGAATCCTG | GATCTGTTAT | AATTTGAGTT | ATGTTTCTCA | ACCTGTTCTG | 540 |
| AGGACAACTA | TTGCTATACA | GGTTATTGTG | AAAACCAAGT | AACATATGTG | AAGGTCCTAT | 600 |
| CACCAAGGGT | GTGCTCAACA | AATACTAGTT | TATGTCCCCT | CCTCATTGTT | TCTCTAAAG | 659 |

(2) INFORMATION FOR SEQ ID NO:64:

(i) SEQUENCE CHARACTERISTICS:
(A) LENGTH: 572 base pairs
(B) TYPE: nucleic acid
(C) STRANDEDNESS: double
(D) TOPOLOGY: linear (i i) MOLECULE TYPE: DNA (genomic)

(x i) SEQUENCE DESCRIPTION: SEQ ID NO:64:

| | | | | | | |
|---|---|---|---|---|---|---|
| GTGGGATCTT | TGTGAACTAC | AAGACAAAAT | TAGGAGCTTT | TCTTACTTTT | TAGGCCTTGA | 60 |
| AGAAGTAACT | AAGCATTACT | AAATGAAATA | ACTATAGAAA | CTATGAAAGT | GTTTTATAGA | 120 |
| TCAGTAAACC | ATATTCTAGC | TGGCAAAACT | GTCCATTACA | TAGCTTTGGG | GCACAATATT | 180 |
| ATGTAACATA | TTTCTCCAGG | AGAATTAGAG | CTTTCAGGGA | GGAATCTGCT | TGCCTGAGTT | 240 |
| CCAGAAAGGT | CTGATATGTC | AATTGGAACC | ATGCTATGGA | AATACCATCC | CCTGCCTGTC | 300 |
| TGCTTTGTAC | CACTTAGTAC | AGGGCTTAGG | TCCTAGAAAA | TTTGGTGTAA | CTTATTAATG | 360 |
| GACACTACTC | AGAAAGCCCT | TGCTATGGTT | ATGGCATAGG | GAGAAAGTTA | ATATCCTAGC | 420 |
| TGAGCTTTGC | TTTTTGGTGT | GAAGAACAGA | GTGCCTATTC | ACTGTTATTA | GCAAGTAGTG | 480 |
| CAGGTAGCTG | TTCCCTTTCT | CCTACTTTTA | AAAAATTAAA | ACAGTCACTA | TTAGCAGCCT | 540 |
| TTGTTCGACA | GCCTTGGTTC | TCCTGGCTGC | AG | | | 572 |

(2) INFORMATION FOR SEQ ID NO:65:

(i) SEQUENCE CHARACTERISTICS:
(A) LENGTH: 901 base pairs
(B) TYPE: nucleic acid
(C) STRANDEDNESS: double
(D) TOPOLOGY: linear (i i) MOLECULE TYPE: DNA (genomic)

(x i) SEQUENCE DESCRIPTION: SEQ ID NO:65:

| | | | | | | |
|---|---|---|---|---|---|---|
| GTAAGTATGA | CAGGGATTAT | TTCATACTTT | TCTCACTCAT | GAGTGTTGAG | GAATCATTTA | 60 |
| TGATTTATAT | ATGGACCATT | CACCTGGTCC | GTATATAAAC | TAGTTTTGGC | CAGGTGTGGT | 120 |

-continued

| | | | | | |
|---|---|---|---|---|---|
| GGCTCACACC | TGTAATCCTA | GCACTTTGGG | AGGCCGAGGA | GGGTAGATCA | CTTGAGGTCA | 180
| GGAGTTCAAG | ACCAGCCTGG | CCAACGTGGC | AAAACCCAGT | CTCTACTAAA | CATACAAAAA | 240
| TGAGCTGGGC | GTGGTGGCAC | ACACTTGTAA | TCCCAGCTAC | TCTGGGGGCT | GAGGCAGGAG | 300
| AATTGTCTGT | ACATGGAAGG | CGGCGGCTGT | AGTGACCTGA | CATTGTGCCA | CTGCACTCCA | 360
| GCTTGGGTGA | CAGAACAAGA | CTCTGTCTCA | TCACTAAGCT | AGCTCTACAA | ACACTTCTCT | 420
| TATGTACAAT | GAGGAAGTCT | GTAATCTACC | TAACCAATAT | AAATTCTACT | GTTGTCAAGC | 480
| ATCAACCGAG | TAAGATTGTA | TTTGGAGTCC | CCGCAAAGTA | TAGTAGTACA | AGAGGCAGGC | 540
| TACATGGGTT | CAAATTTCCC | AGTACTTAAC | AGTGGTGGTA | ACCCTGCAAA | TCATTAAATT | 600
| TTCTCTGTAC | CTCATTTCCT | CATATATAAA | ATGGGAATAT | AACTAGTTCC | TAGCATATGG | 660
| GGTTGTTGTA | AGGATGACAT | GACATAATGT | ATAAAAATTG | CTTACAATAA | TAACTGGCAC | 720
| AAACTAAGCA | CTTAAGGTTT | GCTATTAGAA | TATTTTTCTT | TAGGTTAAGT | TATTGCTAAA | 780
| ACATCACTCT | GTCATTCATA | AAACTACTGG | TTTAGCACAC | CTCTTCACTC | AATAATCATT | 840
| TTCAGTAAAA | ATAATTATAA | ATTTTTTTC | TTAGAATTAC | TGATTTTTTT | TTTTTAAACA | 900
| G | | | | | | 901

( 2 ) INFORMATION FOR SEQ ID NO:66:

( i ) SEQUENCE CHARACTERISTICS:
        ( A ) LENGTH: 4220 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:66:

| | | | | | |
|---|---|---|---|---|---|
| GTGCGCTCGC | GGGCGGAGGG | GCGCTTCCGG | CCTAGTTGGT | GTGAACCGGT | GCCTTCCGAG | 60
| CCGTGTCGCG | CGCCTCGAGA | GACTCTCGGG | CGGGTTGCGG | GCTCCCAGCC | CCGAGAGGGG | 120
| TGGGGACTCC | CTCTGCGCTA | TTCCGAGGCT | CTTAGCCGCT | CCGAGGGTTA | ACCCGCTCTC | 180
| GCCGGGCTTT | CCTGCGGCTT | CCGAATGGGG | AACGTGTCTT | GCCCTAAAGT | AGCACAGCAA | 240
| GGTTGAGATC | GCGTTGGGGC | CCCGTTGAGG | AAAATGGGTG | TGTGTGGTCC | ATCTGACCCC | 300
| CCGCCCGTCT | TGTTAGTAGA | ATGAACTAGT | GTCGTTGTCA | AGACCACACG | GACAAGGGA | 360
| GGGGACTTGC | CCTTATTTGC | ACCGCGATTA | ACCGGGTTGT | GGCACCTGGG | TCTCCACGCG | 420
| TCTCCGTCTG | TTCGCTTCCC | CCTGTTAACC | AAATTGCCTT | TGCCCTGGCG | TTGCGGGCGT | 480
| TTGAGTCAAC | GTGCTGATGC | GTTTTGGGCT | GTGTTTACGT | CTGTGTAAAC | AAATTAATAC | 540
| TCATTTCCCC | CCAGGCCATA | TGAAATGAGC | CCACCGCCGA | CCCGGATGTT | TACACATGCC | 600
| CCCATTTGTC | ACTACGATCA | GGACTGTGGC | TACCTCCAGG | GCTTTTGGT | CACCCCGCGC | 660
| ATTGCACAGG | ACTCCTGTTG | TCGTCGCCAT | CCGGGTGTGT | TAGGTCGCAG | CCTTCGGCAC | 720
| AGGGCTTGCA | CCATGACAAA | AATGGCCATT | CTAGCCAGTG | AGTGTCAGCT | TTGTATGCAC | 780
| CTCCCCTTCA | TGGGCCAATG | GGAAGTGACA | CGGAAGTACG | GATTGTTTAT | CACCTGTTTG | 840
| ACTGTGTGTG | TGGCATTTAA | ACCTGAGGCC | ATTTGATTTC | TCAAGTCGTT | TTATAATTAA | 900
| TTTGTACAAA | GAGTCGGGCA | AATACGTCCA | GGATGCAAAG | CCTAACGAAG | GTATTATTTA | 960
| AATATGATGT | TTTTGGCTAT | GTGTACTGAT | GACTGAGGTT | ATTTTAATT | TGTATTTGCA | 1020
| TTAATACAAT | TTTAATTCAA | TTACTAGTTC | CCTCTTTGAA | TTGTTAGGTC | TGCACAACAT | 1080
| ACTGTATGGT | GGCTTTACAA | CCCGACAGAC | CTGAAACCGC | TGAAAAGTT | CAGTATGGTG | 1140
| ATCTCTAAAC | TGGAGATATT | TGTGTTTACC | TCACAGAGCT | GTTCTGAAGA | TTAAATAAGG | 1200

```
CAATAATGTA  GTTTCTGGCA  CATAAAGCAC  CCATATGGAC  AGTGTTTTCA  AGTTTACTAA  1260
GCTCTTTGTA  TATTTACATG  ATCTGGCTGA  GTAAGCTATG  TTCCTATTCA  TCTCTCAGTG  1320
CCTTTCTGTA  GTCTGGCAAA  GAGAAGGACT  GGTTGGCTTT  TTATGTTGTT  TTTTGTTTTT  1380
TGGGTTTTTT  TTTGGTAAAT  GGCCTTAAAG  GCTTCCAAAC  AAGCTCTTAT  TTTACCCTCA  1440
AGATAATCCT  GTAAATCAGA  TAGAACAAGC  ATTATCGCCA  TTTATTGAG   GTATTTCAAC  1500
TCATAGCAGT  TAAGTTGTAT  GAAGTCTAGT  GATACATGAG  CAAGTATCAC  GTAATAGCTG  1560
GTTAGTAAAT  TATTTTTGAA  ATCATGTTTG  ATTACTCAAT  TCTTTTGATT  ACTGAGACTT  1620
TAGTTTCAGC  TTCTTAGCCC  AGTTTATCAG  TAAATGATTT  ACTCAGTAAA  ATATTCATCA  1680
AATATTTCTT  GAGCACCTAT  TACTTGCTAC  ACATTGTTCT  AGGTGCTGGA  TATAGAGCAC  1740
AAACTGCTCT  TGTGGGGCTT  ACAGTGAGGT  ACGCTGTGAC  AATATGGGAT  GTCATTCTCA  1800
TGGGAGTGCA  AGGGTAAAAT  AAAGCTCTTA  TGATGTTTAA  TACAGAATAC  TGGTTATGGA  1860
ATTTTAACTT  GATTTCTTGT  ATTTTCTGTG  CATTTTAAC   CTGTAACTCA  TTCTCACAGT  1920
CCTCAGCCAA  GAAAATGCAG  CCTCTGAGAC  TGTTAAGTAA  TTTCCCCACT  GTGTTATAGC  1980
TACTGTATGG  CAGAGCCGGA  ATTTGAAACC  AGATCTATTT  GACCCTAGAA  GATGTGACCA  2040
TGAGATGTTA  ATTTTGAGGA  TAACTTTTTT  AGTATTATGG  AATTTTCAAC  ATATATTTTT  2100
TAGGACCAAA  GATAAACTAG  GCACAGAGTC  TACTCTTTGC  ATAAATTATT  TAAAAGAGCT  2160
TCGCGCTCCA  TTTTGTCATC  TAAGCACTGT  AAAATTCTCA  CAAGACTAAT  TCTTCTTTTT  2220
AGGAACGATA  TAGTTGTAAA  CTTTCTATTT  TTTTTCTTTT  TTTTTCTCC   CTCCACCATC  2280
CAAGTAGTTG  TGAATTTTCT  AGAGCCAAAA  TAGAACACTA  TAGATTATCT  TTTAAACCCT  2340
TTATTGAAGC  AGAGGATAAT  GCTGTGACCG  ACTTAACTTT  ATGCTTTCTA  AGAGATATTG  2400
ATATAGTAGA  GAAATGCAGT  AGTTATGCAT  CTCCGTTTGC  TTTTACATCA  TAAATCAAGA  2460
ATATTATGAA  ACCATCTCCC  AGAGATATAT  GTGATACACA  GATCTTGGCT  GTTTTTTTTT  2520
TTTACAAAAG  TAACATCTAT  GCTATTGATA  CATATAAGTG  GGTTTGTAAG  ACAGTCTATG  2580
TGTAAATGTG  AAAAAAGGAA  GAATTTCCAG  TTCTTCTCAT  TTTCATTTAG  ACCAGTAATG  2640
AATACAGTGA  AGCTAAAGGA  CATCTTCCAT  CCTTCCTCGC  TTTTATAGGG  AGAGGAAAGT  2700
TGTATCACTT  CTTGAGTAAA  AAGAATTGTG  ACGATCTTTT  ACAAACAATG  CCTTAAAAAT  2760
TATTATTTTT  GAATGATATG  TGGTAGTGGG  ATCCACAATA  GTCTCATTTG  GTTATACAAA  2820
TAAATTTTAT  GTATTCATGT  ATGTGTTTTG  ATTAGGTATA  AAATTAGTGG  CTGAATATCC  2880
ATTCAAGCTT  AATTTTGTAT  TTCTATCACT  TTTGTAGATT  TTGAGCAAGA  TTAAAAATAT  2940
AAACAATAGG  CCAGGCGCAG  GGGCTCACGC  CTGTAATCCC  AGCACTTTGG  GAGGTCTAGG  3000
TGGGCGAGTC  ACGAGGTCAG  GAGATCAAGA  CCATCCTGGC  TAACACATTG  AAACCCAGTC  3060
TGCTACTAAA  AATACAAAAA  ATTAGCTGAG  CGTGGTGGTG  GGCACCTGTA  GTCCCAGCTA  3120
CTCAGGAGGC  TGAGGCAGGA  GAATGGTGTG  AACCTGGGAG  GCAGAGCTTG  GAGTGAGCCA  3180
AGATGGAGCC  ACTGTACTCC  AGCCTGGGTG  ACACAGTGAG  ACTCCATCTC  AAAAAAAATA  3240
AAAATAAAT   AAAAATAAAC  AATAATATTG  TTTGCATTAC  TATGGCTATA  TAGCAAATTG  3300
CCTTAAAACT  TAGGGGCAGA  AAGCAATTTG  TTTTGGTCAC  AGGTTCTGTG  AGTAAGGAAT  3360
TCAGGCTGGG  GACAGTGTGG  ATGTCATGTT  TCTGCGTCAA  AATGACTGGT  ACCTCACCTG  3420
GAAGACTTGA  GCAACTAGGT  ACTGGCACAG  CTGGAGCTCG  TTGGGCATCT  CTGTATGTTT  3480
GTTCCATGTG  GTCTCACCAG  CATGGTGATC  CAGGGTAGGT  AAATTGTTAC  ATGCTGGTTC  3540
AGGACTCCGA  AGGCACATGT  CCTAAGAGAG  AGAACCAAGT  GGAATCTATA  GTGCGTTGTA  3600
```

| | | | | | |
|---|---|---|---|---|---|
| TAATCTTTTA | GAATTACATA | GTTTCAGTTG | TACCTGTGCA | ATTATTGATA | GAGACAGTTA | 3660 |
| ATCAGTGTGA | GGGAACACAG | ACCCTTGCCC | AGGTCCAAGG | TGAGGGAACC | CTCTGTACCT | 3720 |
| GTCAGTGGAA | TAATGTTAAT | GTCACATTAT | AAGAAGAGCC | TGACGGGGCT | GGGTAGAGTG | 3780 |
| GCTCACACCT | GTAATCCCAG | CACTTTGGAA | GACCAAGGCG | GATGGATCAC | TTGAGGCCAG | 3840 |
| GAGTTCAAGA | CCAGCCTGGG | CGACATGACA | AAACCCTGTC | TCGACCAAGA | AAACATAGAA | 3900 |
| TTAGCCAGGT | ATGGTGGCGC | ACTTCTGTAG | TCCCAGCTAC | TTGGGAGACT | GAGGTAGGAG | 3960 |
| GAGTGCTTGA | ACCTGGGAGG | TGGAGGTTTC | AGTGAGCCAA | GATTGCGCCA | CTGCACTCCA | 4020 |
| GCCTGGGTGA | CAGAGCAAGA | TTCCATCTCC | GAGAGAAAAA | AAAAAAAAA | AAAAAAGAG | 4080 |
| CGTATGAGAT | AGGGTCATCA | TTGAAACTAA | GTTTCCCACA | AAAATATAAA | CAACACTTTC | 4140 |
| AATTTAAACA | TACTTTTAAA | AATATTGAAA | TATTTATATG | TAGCTTTTA | ACTGAAAATC | 4200 |
| AATTTTCTTT | TCTTTTACAG | | | | | 4220 |

(2) INFORMATION FOR SEQ ID NO:67:

(i) SEQUENCE CHARACTERISTICS:
        (A) LENGTH: 3507 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:67:

| | | | | | |
|---|---|---|---|---|---|
| GTAACTATGT | TAGAGTTTGA | CAAGTAGAGT | ATGGCTAATG | TAAGCTCATA | AATCATAGTG | 60 |
| ATAGTAAGAA | TTATCTCTGC | TCATCATTTC | CTGAGCATTT | GTACCTGTGG | ACTGGCGAAA | 120 |
| TTAGATGCTA | AAACTAGCAT | CTAATGATTT | TCCTCCTCTA | TATCACAGTT | AATATCCATT | 180 |
| ATATTTACT | TCTTTGGTGA | AAATATTTAA | ATTTTAATGT | TTTAGGCACT | TGTATGGCAG | 240 |
| AATTTATTTT | TAAAGTTTAG | GACATTGTGT | AATATTGGGA | GAAATGAAGG | ATATTGAGAA | 300 |
| ACTTTAGGAG | ATACTCCAAG | TTGAAAAGGT | AAATAAAATA | TTATTTGCTA | TTATACTTAG | 360 |
| CAAATATGTG | CACAGGACTT | GTGGTCTTAA | TATAAATGGA | ACATGTAAGT | ATTTCTCAGT | 420 |
| TTCCTGTTTG | GAGGATAAAT | GACATGATTA | TAATCCATTT | TAGAAAGGGT | CAAATATGTT | 480 |
| TAAAAGAAGA | GGCAGAAATT | GCTTTATCTG | TTGTGTAATT | AAATTGATTA | CATTTATTTT | 540 |
| TTGTGCCTTT | TAGGTGAATT | TTCTTACATG | GCTTATTAAA | GATAAGTGGA | AAAATGATGT | 600 |
| TTAGCATTTT | GGGGGAAATT | ACCACTGTCA | AAATTTATGG | AGTTAATGGT | TAAAAAATCA | 660 |
| CTTACTAAAT | AAAAAAATTA | ACTGGGTGTG | GTTGTGCATA | CCTGCAGGCC | TAGCTACTTG | 720 |
| GGAGGCTGAG | ATGGGAGGAT | CACTTGAGCC | CTGAATGATG | GAGCAGCACT | GCACTCCAGC | 780 |
| CTGGGCCACA | GAGCAAGACC | TTGTCTCCAA | AAAAAAAAA | AAAAAGAAG | GTTACTATTA | 840 |
| AATAATTAG | CAGGCTGGGG | GCGGTGGCTC | ACACTTGTAA | TCCCAGTAAT | CCCAGCACTT | 900 |
| TGGAGGCCAA | GGTGTGTGGA | TCACTTGAGG | TCAAGAATTG | GAGATCAGCC | TGGCCAATAT | 960 |
| GGTGAAACCC | CGTCTCAACT | AAAAATACAA | AAATTAGCCG | AGTGTGGTGA | CATGCGCCTG | 1020 |
| TAATCTTAGC | TACTCAGGAA | GCTGAGTCAG | GAAAATCACT | TGAGCCCAGG | AGGCACAGGT | 1080 |
| TGCAGTGAGC | ACTATTGCAC | TCCAGCCTGG | GTGACAAGAG | CGAGACTCCA | TCTCAAAACA | 1140 |
| AATAAATAAA | ATAAAATAAT | TCACAATGTC | ATGTTTTAGC | TGACATTGTG | AATTTTAGTA | 1200 |
| ATCTTTTTTT | AACCTTTAAC | TCCATCCTGA | GTTACATTGA | CCAAAGAAAT | CAGTATCTAG | 1260 |
| AATTATATCA | GGGAACTACT | AACAGGGTTA | ATAAAATGAA | TAAAGAACAT | GACTTCACAA | 1320 |

-continued

| | | | | | |
|---|---|---|---|---|---|
| AGGTTATAAT | TCACATAGCT | AATAGATACA | GGAAGAGATA | TTCACTGTCA | CTAATAAAGA | 1380 |
| CTTTCAAAGT | AGAAAGATAA | CATTTCATTC | TGTTTTTTTT | GAGATGGAGT | CTTGCTGTTT | 1440 |
| CACCCAGGCC | AGGGTGCAGG | GGCGTGATCT | CAGCTCATTG | CAGCGTGTGC | GTCCCAGGTT | 1500 |
| CAAATGATTC | TCCCGCTGTG | GCCTCCCAAG | TAGCTGGGAT | TACAGATGCG | CACCACCACA | 1560 |
| CCTGGCTAAT | TTTTTGTATT | TTTAGTAGAG | ACGGGTTTCA | CCATGTTGGC | CAGGCTGGTT | 1620 |
| TCCAACTCCT | GACCTCAGGT | GATCCACCCG | CCTTGGACTC | CCAAAGTGCT | GGCATTACAG | 1680 |
| GTGTGAGCCA | CCATGCCTGG | CCAACATTTT | ATTCTTATCA | TTGGGAAAAT | TTGAAGTCTG | 1740 |
| GTATACCAAG | TTTGGTCACT | GTACAGGGAA | ACAGGAACTC | TATTTTTTTT | ATTTTTCAGT | 1800 |
| TCTTTTTTTT | TTTTTTTTTT | TTTTTTGAG | ATGGAGTCTC | ACTCTGCTGC | CCAGGCTGGA | 1860 |
| GTGCAGTAGC | TCAATCTCTA | CTCACTGCAA | CCTCCACTTC | CCAGGTTCAG | GTGATTCTCA | 1920 |
| TGCTTCAGCC | TCCCGGAGTA | GCTGGGATAA | AGGCACATAC | CACTATACCT | GACTAATTTT | 1980 |
| TGTATTTTTT | GTGGAGACCA | GGTTTCACCG | TGTTGACCAG | GCTAGTCTCG | AACTCCTGAC | 2040 |
| CTCAAGTGAT | CTACCTGCCT | CGGTCTCCCA | AAGTGCTGGG | ATTACAGGCA | TGAGCCACTG | 2100 |
| CGCTCAGGCA | GGAACTCTAT | ATTGCTGGTG | TACATTGGTG | AGAGTCAAAA | TTGACACAAC | 2160 |
| TACTTTACTA | GCAAATTTGG | TGGTATTTAG | TAATATTGAA | GGTGCACATT | CTCTTACTGT | 2220 |
| ACTTCTTGGA | GTAGTCCCCA | AAGAAACTCC | TGCACACATG | TATAAGGATG | TTTTCATTAC | 2280 |
| AACATGTTTT | GTTATCATGG | AATATTAGAA | ACAACCTAAA | TTTCCATTGG | TTGGGGAGTG | 2340 |
| AATGCAAAAA | GTCATTGTAT | GTTCATATGA | AAGAATGTTT | TTAGCAATTA | AAATGAATAT | 2400 |
| ATCTTACATA | TCAACATTAA | TGTCAGAAAC | ATTATTGAGT | GTGAAAAGC | AAGTTGCAGA | 2460 |
| ATACCACTGA | AGTATGATAG | CATTTATATA | AAATGTAAAA | ACACGTAATA | AGATATTGCT | 2520 |
| TATTGTTTAC | ACATACATGT | GTATGTGTAG | TAAGTGTGAA | AACATAGGAA | GGATTAAGAC | 2580 |
| CAACTTTGGA | ATGGTTTTA | TCTTTGGGGT | AGAAGGGTAA | GGATGGGATT | AGGGAGGAGT | 2640 |
| ATAAAATGGT | AATTTTGACT | GTTTCTTTTT | CTTTTTCTTT | TTCTTTTTTG | AGACAGAGTC | 2700 |
| TCGCATTGTC | GCCAGGCTGG | AGTGCAGTGG | CGTGATCTCG | GCTCACTGCA | ACCTCCGCCT | 2760 |
| CCCAGGTTTA | AGTGATTTTC | CTGCCTCAGC | CTCCTGAGTA | GCTGGGATTA | CAGGTGCCCG | 2820 |
| CCACCACGCC | CAGCTAATTT | TTTGTATTTT | TAGTAGAGAT | CGGGTTTTAC | CATGTTGGCC | 2880 |
| ATGCTGGTTT | CAAACTCCTG | ACCTTGTGAA | TCTCCACCT | CGGCCTCCCA | AAGTGCTGGG | 2940 |
| ATTACAGGTG | TGAGCTACTG | CGCCTAGCCT | TGACTGCTTT | TATAGTGTTG | CTAGTTTAAA | 3000 |
| AAAAAATCTG | AAGTGGCAGG | AGGAGGTGGC | TCACACCTGT | AATCACAGTG | TTCTAGGAAG | 3060 |
| CCAAAGTAGG | AGGATCACTC | AAGCCCAGGA | GTCTGCGGTG | AGCTGTGATC | TTGCCACTGA | 3120 |
| ACTCCAACAT | GGGTGATAGA | ACGAAACCCT | ATCTCTTACA | AAAACAAAAA | CGACAAAATT | 3180 |
| TATTTAATAT | ATTAACATTT | AAAAAATCTG | GCAGTGAACC | AACGTGAATG | TTGGTTAGGT | 3240 |
| TACTCTTGTT | AATTTTGGTT | TGTATTTTCA | AATATTTCAT | AGTTAACAAA | TACTTTAGGT | 3300 |
| AACCTAAACA | AAATGGATTA | GGAGGATCAG | AGGAATATAC | CAATCTGTAA | GAAATTAAGC | 3360 |
| TAGTCAGAGA | CATGAGTTGT | GATTTTATTT | CACTGTCTAA | AAGTAATATA | ATTTAATGCG | 3420 |
| ATAATATTGA | TTTACTTTTG | AATACTTACT | TTTGTATACT | TTAGCCTTAT | GTTAATTATG | 3480 |
| AAATATCTTG | TTTGTCTTTA | ATACCAG | | | | 3507 |

( 2 ) INFORMATION FOR SEQ ID NO:68:

( i ) SEQUENCE CHARACTERISTICS:
        ( A ) LENGTH: 9837 base pairs
        ( B ) TYPE: nucleic acid ( C ) STRANDEDNESS: double
( D ) TOPOLOGY: linear ( i i ) MOLECULE TYPE: DNA (genomic)

( x i ) SEQUENCE DESCRIPTION: SEQ ID NO:68:

| | | | | | | |
|---|---|---|---|---|---|---|
| GTGAGCCTAA | CATCAATCTT | GGCCTTTACT | AACCTCAAAA | TGCTTCAGAT | GCTAGAAACA | 60 |
| GGGTTTGTGC | TAAGCTTAGG | CACTCATTAG | AGTGATGAGA | GCTGCCAGGG | AGCAGTGATC | 120 |
| AGTCAGTCCT | CATGAAGCAA | AACCCAGGGT | TGTTTTGTTT | TTTGCCTTTT | TTGAGGGGA | 180 |
| GGGGGTGGAA | TTTAAGGGTG | GGAAACAGGG | CAAGGGATTT | TGATTCTTTT | TATTCCCTCT | 240 |
| CCTATTTGTA | CATTTTGGTG | TAAACCTGAA | ATTGATTTCT | TACCAAAGGC | CTGTTTCTGG | 300 |
| GACAGGCAGT | GTCCTCAGGA | GTCTGGCTAA | TGGGAGAAGT | TGACATTTTT | GACATTGCAG | 360 |
| TTCAATAGTC | ATATTAGCAC | AGATGTATGT | GGCAACAGCC | ACCTCATTCT | AAGAAGGGGA | 420 |
| AGGAAGCTTG | AGTCAGGCCT | TAATGTTGAA | AAGTCAGGGA | GCTGTTGAGG | TATGGAAGGG | 480 |
| CACTCAGCAG | GAAGCAGGTT | AAGGGGAAGA | AAACAGTGTC | CTTGAGGCAG | ACAGTGATTC | 540 |
| AAAGCTTAAT | TACGGGCATC | ATGCTATGTT | AGCGAGTGGA | ACTGGATTGT | GACGGCCCTT | 600 |
| ACATAATGAG | ATTTTTATTG | ATAAAGGTTG | CTTAGAGGCT | GGGCGTTGTG | GCTCACACCT | 660 |
| GTACTCCCAA | CACTTTGGGA | GGCCACAGTG | GGCAGATCAC | CTGAGGTCAG | GAGTTCATGA | 720 |
| CCAGGCTAGT | CAACACGGTG | TAAACCTCAT | CTCTATTAAA | AATACAAAAA | TTAGCTGGGT | 780 |
| GTGGTGGAAT | GCACCTGTAA | TCCCAGCTAC | TCGGGAGGCT | AAGGCAGGAA | AATAGCTTGA | 840 |
| ACCCAGGAGG | TGGAGGTTGC | AGTGAGCAGA | GCATTGCGCC | ATTGCACTCC | AGCCTGGGTG | 900 |
| ACAAAGCGA | AACTCACTGT | CTCAAAAAAA | AAAAAAAACC | GGTTGCTTAG | AAATACACAT | 960 |
| TTTTTTTTGG | CCTGAACTCT | TCAAAAAAAG | GTCAGTATGG | TAAGAGGACG | GGGAAGGTTT | 1020 |
| CGTAGAGGAG | ACTAGGGAGA | CACGACATCC | AAATGCAATG | CATGATTCTT | GACCCTGCAT | 1080 |
| AGGAAATCGT | CGTTATAAAG | GACATTTTGA | GGAAATTTG | AATGTGGGCT | TTAGTGTATT | 1140 |
| TTTTTTTTA | AAGTTTCTTT | GGTGTTGATG | ATGTCTAGCA | GATTATGTAG | GAGACTGTGC | 1200 |
| TGAAAAGTAT | TCAGAGGTAA | AGTGTCCCAG | TGTCTGCAGC | TTACTTTCAA | ACGGGTTGGT | 1260 |
| TGCAATATAT | TTAGGTAGGG | AGAGAGTGAA | AGTAACTCTT | AGACATTAAT | GATTGATAAG | 1320 |
| TGGCTGTTCA | GTGTACTATT | TTTTTCAACT | CTTTGTAGGC | TTGCAATCTT | TTAAAAGTT | 1380 |
| GAGGAAAACA | GTCCGGGTGC | AGTGCCTCAC | GCCTGTAATC | CCAACATTTT | GGCAGGCTGG | 1440 |
| GATGGGAAAA | TTGCTTGAGG | CCAGAATTTG | GAAAACGGCT | CAGGCAACAT | AAAACCCCAT | 1500 |
| CCCTACAACA | AATAAAAATT | AGCTGAGCAT | GGTGCCATGC | ACCTGTAGTT | GTATCTACTC | 1560 |
| AGGAGGCTGA | GCCCAAAATT | TCAAGGCTGC | GGTGAGCTAT | GGTCGTGCCA | CCACACTCCA | 1620 |
| GCCTGGGCAA | TAAATTGAGA | AACCCTGTCT | GTTTGGAAAA | AAAAGTTGAG | GAAAACAATT | 1680 |
| AAACAATAAC | AGCAAAAATC | TGTTATAAAA | TGTAATAATG | GGCCAGGTGT | GGTGGCTCAT | 1740 |
| GCCTGTAATC | CCACCACTTT | GGGAGGCCGA | AATGGGTGGA | TCACCTGAGG | TCAGGAGTTC | 1800 |
| AAAATCAGCT | TGGCCAACAT | GGTGAAACCC | CATCTCTGCT | AAAATTACAA | AAAAATTAGC | 1860 |
| TGGGTGCGGT | GGCGCACACC | TGTAATCCCA | GATACTCAGG | AGGCTGAGGC | AGGAGAATCG | 1920 |
| CTTGAACCCA | GGAGGCGGAG | GTTGCAGTGA | GCCGAGATCG | TGCCACTACA | CTCCAGCCTG | 1980 |
| GGCAACAGAG | CCAGACTCTG | TCTCAAAAAA | AAAAAAAAGT | TAATTCACG | CAGAGCCAGC | 2040 |
| TGAACGGCAG | ACAGGAGTTT | GGTTATTCAA | ATCAGCCTAC | CAGAAAATTC | GGAGACTGGG | 2100 |
| GTTTTTAAAG | AATGACTTGG | CGGGTAGGGG | GCCAGGGATT | GGCGAATGCT | AATTTGTCAG | 2160 |
| GTGGGAGGTG | AAATCACAGG | GGGTTGAAGT | GGGCTCTTGC | TGTCTTCTGT | TACTGAGTGG | 2220 |

```
AATTGCAGAA  CTTGTTGAGC  CAGATTATGG  TCTGAGTGGC  GCCAGCTAGT  GCATTGGAAT    2280
GCGCGGTCTG  AAAAGTATCT  CCAGCACCAA  TCTTAGGTTT  TACAATAGTG  ATGTTATCCC    2340
TGAGAGCAAT  TGGGGAGGTC  AGGAATCTTA  TAGCCTCTGG  CTGCAAGCCT  CCTAAATCAT    2400
AATTTCTAAT  CTTGTGGCTA  ATTTGTTAGT  TCTACAAAGG  CAGACTGATC  CCCAGGCAAG    2460
AATGGGGTTT  GTTTTGGAA   AGGACTGTTA  CAATCTTTGT  TTCAAAGTGA  AATTAGAAAT    2520
TAAATTCCTC  CTGTAGTTAG  TTAGGTCTTC  GCCCAGGAAT  GAACAAGGGC  AGCTCGGAAG    2580
TGAGAAGCGT  GGAGTCATTT  AGGTCAGATC  CCTTGCACTG  TCATAACTTT  CTCACTGTTA    2640
GGATTTTTGC  AAAGGCAGTT  TCGTGAACGT  ACAGAGACAG  GCCCTTGCTA  TTATCCCTAT    2700
TTTTTAGATA  AGGATATCCA  GGCGATGAGG  AAGTTTTACT  TCTGGGAACA  GCCTGGATAC    2760
GAAACCTTCA  CACGTCAGTG  TCTTTTGGGA  CATTTCTCG   TCAGTACAGC  CCTGTTGAAT    2820
GTTCTCACGG  TGGGGAGGTA  CGTGTTTAAA  ATGCGGGGAA  GGTGCTTTTA  TTTCACCCCT    2880
GGTGAAACTA  GGGGAGCTAA  TTTTTTTAAA  CATGATTTTT  GGCCCCCTTG  AACCGCCGGC    2940
CTGGACTACG  TTTCCCAGCA  GCCCGTGCTC  AAGACTACGG  GTGCCTGCAG  GCGGTCAGAG    3000
TCGTTTGCGG  CGGCGCAGGC  GCGGTGCGGG  CGGCGGACGG  GCGGGCGCTT  CGCCGTTTGA    3060
ATGGCTGCGG  GCCCGGGCCC  TCACCTCACC  TGAGGTCGGC  CGCCCAGGGG  TGCGCTATGC    3120
CGTCGGGAGG  TGACCAGTCG  CCACCGCCCC  CGCCTCCCCC  TCCGGCGGCG  GCAGCCTCGG    3180
ATGAGGAGGA  GGAGGACGAC  GGCGAGGCGG  AAGACGCCGC  GCCGCCTGCC  GAGTCGCCCA    3240
CCCCTCAAAG  CCGAATTCTG  CAGATATCCA  TCACACTGGC  GGCCGCTCGA  GCATGCATCT    3300
AGAGGGCCCA  ATTCGCCCTA  TAGTGAGTCG  TATTACAATT  CACTGGCCGT  CGTTTTACAA    3360
CGTCGTGACT  GGGAAAAACC  CTGGCGTTAC  CCAACTTAAT  CGCCTTGCAG  CACATCCCCC    3420
TTTCGCCAGC  TGGCGTAATA  GCGAAGAGGC  CCGCACCGAT  CGCCCTTCCC  AACAGTTGCG    3480
CAGCCTGAAT  GGCGAATGGA  CGCGCCCTGT  AGCGGCGCAT  TAAGCGCGGC  GGGTGTGGTG    3540
TTACGCGAGC  GTGACCGCTA  CACTTGCCAG  CGCCCTAGCG  CCCGCTCCTT  TCGCTTTCTT    3600
CCCTTCCTTT  CTCGCCACGT  TCGCCGGCTT  TCCCCGTCAA  GCTCTAAATC  GGGGGCTCCC    3660
TTTAGGGTTC  CGATTTAGTG  CTTTACGGCA  CCTCGACCCC  AAAAAACTTG  ATTAGGGTGA    3720
TGGTTCACGT  ATTGGGCCAT  CGCCCTGATA  GACGGTTTTT  CGCCCTTTGA  CGTTGGGAGT    3780
CCACGTTCTT  TAATAGTGGA  CTCTTGTTCC  AAACTGGAAC  AACACTCAAC  CCTATCTCGG    3840
TCTATTCTTT  TGATTTATAA  GGGATTTTGC  CGATTTCGGC  CTATTGGTTA  AAAAATGAGC    3900
TGATTTAACA  AAAATTTAAC  GCGAATTTTA  ACAAAATTCA  GGGCGCAAGG  GCTGCTAAAG    3960
GAAGCGGAAC  ACGTAGAAAG  CCAGTCCGCA  GAAACGGTGC  TGACCCCGGA  TGAATGTCAG    4020
CTACTGGGCT  ATCTGGACAA  GGGAAAACGC  AAGCGCAAAG  AGAAAGCAGG  TAGCTTGCAG    4080
TGGGCTTACA  TGGCGATAGC  TAGACTGGGC  GGTTTTATGG  ACAGCAAGCG  AACCGGAATT    4140
GCCAGCTGGG  GCGCCCTCTG  GTAAGGTTGG  GAAGCCCTGC  AAAGTAAACT  GGATGGCTTT    4200
CTTGCCGCCA  AGGATCTGAT  GGCGCAGGGG  ATCAAGATCT  GATCAAGAGA  CAGGATGAGG    4260
ATCGTTTCGC  ATGATTGAAC  AAGATGGATT  GCACGCAGGT  TCTCCGGCCG  CTTGGGTGGA    4320
GAGGCTATTC  GGCTATGACT  GGGCACAACA  GACAATCGGC  TGCTCTGATG  CCGCCGTGTT    4380
CCGGCTGTCA  GCGCAGGGGC  GCCCGGTTCT  TTTTGTCAAG  ACCGACCTGT  CCGGTGCCCT    4440
GAATGAACTG  CAGGACGAGG  CAGCGCGGCT  ATCGTGGCTG  GCCACGACGG  GCGTTCCTTG    4500
CGCAGCTGTG  CTCGACGTTG  TCACTGAAGC  GGGAAGGGAC  TGGCTGCTAT  TGGGCGAAGT    4560
GCCGGGGCAG  GATCTCCTGT  CATCCCACCT  TGCTCCTGCC  GAGAAAGTAT  CCATCATGGC    4620
```

```
TGATGCAATG CGGCGGCTGC ATACGCTTGA TCCGGCTACC TGCCCATTCG ACCACCAAGC    4680
GAAACATCGC ATCGAGCGAG CACGTACTCG GATGGAAGCC GGTCTTGTCG ATCAGGATGA    4740
TCTGGACGAA GAGCATCAGG GGCTCGCGCC AGCCGAAACT GTTCGCCAGG CTCAAGGCGC    4800
GCATGCCCGA CGGCGAAGGA TCTCGTCGTG ACCCATGGCG AATGCCTGCT TGCCGAATAT    4860
CATGGGTGGA AAAATGGCCG CTTTTCTGGG ATTCATCGAA CTGGTGGCCG GGCTGGGTGT    4920
GGCGGACGCT ATCAGGACAT AGCGTTGGCT ACCCGTGATA TTGCTGAAGA GCTTGGCGGC    4980
GAATGGGCTG ACCGCTTCCT CGTGCTTTAC GGTATCGCCG CTCCCGATTC GCAGCGCATC    5040
GCCTTCTATC GCCTTCTTGA CGAGTTCTTC TGAATTGAAA AAGGAAGAGT ATGAGTATTC    5100
AACATTTCCG TGTCGCCCTT ATTCCCTTTT TTGCGGCATT TTGCCTTCCT GTTTTTGCTC    5160
ACCCAGAAAC GCTGGTGAAA GTAAAAGATG CTGAAGATCA GTTGGGTGCA CGAGTGGGTT    5220
ACATCGAACT GGATCTCAAC AGCGGTAAGA TCCTTGAGAG TTTTCGCCCC GAAGAACGTT    5280
TTCCAATGAT GAGCACTTTT AAAGTTCTGC TATGTGGCGC GGTATTATCC CGTATTGACG    5340
CCGGGCAAGA GCAACTCGGT CGCCGCATAC ACTATTCTCA GAATGACTTG GTTGAGTACT    5400
CACCAGTCAC AGAAAAGCA TCTTACGGAT GGCATGACAG TAAGAAGAAT TATGCAGTGC    5460
TGCCATAACC ATGAGTGATA ACACTGCGGC CAACTTACTT CTGACAACGA TCGGAGGACC    5520
GAAGGAGCTA ACCGCTTTTT TGCACAACAT GGGGGATCAT GTAACTCGCC TTGATCGTTG    5580
GGAACCGGAG CTGAATGAAG CCATACCAAA CGACGAGCGT GACACCACGA TGCCTGTAGC    5640
AATGGCAACA ACGTTGCGCA AACTATTAAC TGGCGAACTA CTTACTCTAG CTTCCCGGCA    5700
ACAATTAATA GACTGGATGG AGGCGGATAA AGTTGCAGGA CCACTTCTGC GCTCGGCCCT    5760
TCCGGCTGGC TGGTTTATTG CTGATAAATC TGGAGCCGGT GAGCGTGGGT CTCGCGGTAT    5820
CATTGCAGCA CTGGGGCCAG ATGGTAAGCC CTCCCGTATC GTAGTTATCT ACACCGACGG    5880
GGAGTCAGGC AACTATGGAT GAACGAAATA GACAGATCGC TGAGATAGGT GCCTCACTGA    5940
TTAAGCATTG GTAACTGTCA GACCAAGTTT ACTCATATAT ACTTTAGATT GATTTAAAAC    6000
TTCATTTTTA ATTTAAAAGG ATCTAGGTGA AGATCCTTTT TGATAATCTC ATGACCAAAA    6060
TCCCTTAACG TGAGTATTCG TTCCACTGCA GCGTCAGACC CCGTAGAAAA GATCAAAGGA    6120
TCTTCTTGAG ATCCTTTTTT TCTGCGCGTA ATCTGCTGCT TGCAAACAAA AAAACCACCG    6180
CTACCAGCGG TGGTTTGTTT GCCGGATCAA GAGCTACCAA CTCTTTTTCC GAAGGTAACT    6240
GGCTTCAGCA GAGCGCAGAT ACCAAATACT GTTCTTCTAG TGTAGCCGTA CGTAGGCCAC    6300
CACTTCAAGA ACCTCTGTAC CACCGCCTAC ATACCTCGCT CTGCTAATCC TGTTACCAGT    6360
GGCTGCCGCC AGTGGCGATA AGTCGTGTCT TACCGGGTTG GACTCAAGAC GATAGTTACC    6420
GGATAAGGCG CAGCGGTCGG GCTGAACGGG GGGTTCGTGC ACACAGCCCA GCTTGGAGCG    6480
AACGACCTAC ACCGAACTGA GATACCTACA GCGTGAGCTA TGAGAAAGCG CCACGCTTCC    6540
CGAAGGGAGA AAGGCGGACA GGTATCCGGT AAGCGGCAGG GTCGGAACAG GAGAGCGCAC    6600
GAGGGAGCTT CCAGGGGGAA ACGCCTGGTA TCTTTATAGT CCTGTCGGGT TTCGCCACCT    6660
CTGACTTGAG CGTCGATTTT TGTGATGCTC GTCAGGGGGG CGGAGCCTAT GGAAAAACGC    6720
CAGCAACGCG GCCTTTTTAC GGTTCCTGGC CTTTTGCTGG CCTTTTGCTC ACATGTTCTT    6780
TCCTGCGTTA TCCCCTGATT CTGTGGATAA CCGTATTACC GCCTTTGAGT GAGCTGATAC    6840
CGCTCGCCGC AGCCGAACGA CCGAGCGCAG CGAGTCAGTG AGCGAGGAAG CGGAAGAGCG    6900
CCCAATACGC AAACCGCCTC TCCCCGCGCG TTGGCCGATT CATTAATGCA GCTGGCACGA    6960
CAGGTTTCCC GACTGGAAAG CGGGCAGTGA GCGCAACGCA ATTAATGTGA GTTAGCTCAC    7020
```

```
TCATTAGGCA CCCAGGCTTT ACACTTTATG CTTCCGGCTC GTATGTTGTG TGGAATTGTG    7080
AGCGGATAAC AATTTCACAC AGGAAACAGC TATGACCATG ATTACGCCAA GCTATTTAGG    7140
TGACACTATA GAATACTCAA GCTATGCATC AAGCTTGGTA CCGAGCTCGG ATCCACTAGT    7200
AACGGCCGCC AGTGTGCTGG AATTCGGCTT AAAGGTAGGC GGATCTGGGT CGACTCTAGG    7260
CCTAAATGGC CATTTAGGTG ACACTATAGA AGAGCTCGAG GACAACAGAA ATCTTAGTG    7320
AACATGTTTT ATGGGAAAAT TTTATATACA ACATCAAAAG CACAATCCGT AAAATACTGT    7380
TAAAATGGAT TTTATCAAAA TGAATAATTT CTGCTATTTG AGACACTGTT AAGAGAATTA    7440
AAAAACCAGC CATAGACTAT TAGAAAATCT GTACACGTTC CATATCTGAT GAAGCATTTG    7500
TATATCTACA GTATCTAAAG AATTCTCAAA ATTCAGTAGG AAAACCACCA AATGTAAAAG    7560
TGGGCAAAAG ATTTGAACAC ACTTCACCCA TTACATGCCT GTTAGAATGG CTAAAATCCA    7620
AAAAGTGACA AATCGTAAGT TCTGACAACA ATGTGGAACA ATTTTACATA TTGCTGGTGT    7680
GAACGCAAAA TGGCATCGCC ACTGTGGAAA GTTGTTTCTT AAACATACCA TTATACAACC    7740
AGCAATCTCA TTCCTAGGTA TTTACACAAA TGAAATGGAA ACTTATGTTT AGACAAAATC    7800
ACGTACATGA CTGTTTATAG TGACTTTCTT CCTAATTGCC AAAAAGTGGG AAACAACCCA    7860
AACGTCCTTC AGCTGGTGAA TGCATATAAA TAAGCTGTGG TGCATCCAGA CAATCGACTG    7920
CTACTTTGCA ATAAAAAGGA ACTGATATAT TCAATGTAGA TAAATCTCAA ATGCATCAAT    7980
GCTTAAGTGA AAGACACTGG ATTCAGTAGG CTACTTATGA TTCCATTTCT GTGACATTGT    8040
GGAAAAGGCA AAACTATTGG ACAAGAACAT CAGTGGTGGT TTGGGATAGG CTGACAAGGG    8100
AGTATGAGGG ATTTTTTCAG AGGAACAGTT TTATCCGACT GTAGGTATTT CTAGCACAGA    8160
ATTGGGAGTC TGTCCAGTAA AATGATAGCG ATTATTAGAC TCTTGGTTGG AGAAAGATTT    8220
GTCATCTTGA CGTAATAGGT GATAGCTGAA ACTTACGGGG AGAATATTAC AAAGCAAGGA    8280
GGGGGAGAAT ATTCCCAAGC AAGAAGTAGC TTATGTCTAG AACCAATCTA TAACGTACTA    8340
ACATTTAGAC TACTATGAGG GGATAATTAT CAAATACTAT ACAAGATCAG TTAAGATGAA    8400
GACTGATCAT TAGTGATACT TGACAGAGCA GTGTCAGTGC ACTGGTATGA CTTGTTGAGA    8460
AATAAATTAT GGTAGCATTG CTTATACACA ATTAACGATG TATACAGTAA GACAGTGTGA    8520
GAAATATTCA AGCAAATGGG AGACCGCAGA GATACCAAAT GCAGACCAGA CTCTTAGGAG    8580
GCAAGAAGGG GGCTAGAAAA AGAATTGAAG GAAAGCTTTC TTCAGATGCT TAAGATTTTG    8640
TGGCCAGGTG CAGTGGCTCA TGCCTGTTCC CAGCACATTA GGAGGCCCAA AGCAGGAGGA    8700
TTGCTTGAGC CCAGGAATTC AAGACCAGCT TGGACAACAT AGTGCAACCC CATTTCTATT    8760
GGTAATTAAA AAAAAAAAAA AATGAAAAAC ACTTGTGAAG GTACATCTGT TGATAATAAA    8820
GAACACTGAT TTTCATTAAA ACCCCCAAAA CATTTATTAC TTTAAAGAAT AAAAATAACA    8880
AGTGTCATGA TAAAATATGT CTGGGATTTG TTTTAAAATA ATCTGGGGAA TGGAAGTGAA    8940
TCAGAGTATA AATCAAGCAA GGCTGGCCAA ACATGCTGAA GTAGAGGAAT AGGTATGTGA    9000
GGATGCATTA TGCTTCTCTA CTTTTGTATG TTTACAATTT CCCTATAATA GATATCTGTG    9060
AATTTGCTTA GTATGCTTTC TGTAAGCAAA CATGGATGAA GCAGCACATG AAAAAGAATT    9120
TTAACCAACA AACTAGCAGA AATAATGTGA CAGACGACTT TTAGAGGCTT TGGAGAAACT    9180
GAATGCTAAA GGTGCTGTAC AGCCAGCCCC AGTCTTTCTG ACATTCTGGC AGTGTCTTTC    9240
TCAATTGCAG CTCCTCATCT GAGCCACTGT CCAGAAAATA ATTTGAGTAA CTTTAATCCT    9300
CAATTCTCCC AAGGATAGTA CCATTCTAGA TCTTACTAAT TTATTAGCTA CAATGGATAC    9360
CTTAGGGGGG GATTAAGGCC TACTTTTCTA GTGAAATCCC AGTTGAGAAT GGCTGCTAAA    9420
```

| | | | | | | |
|---|---|---|---|---|---|---|
| AACTGAGTAA | CATTAGACTG | AAAGAAAGGG | AATATTGTAT | AAAGTTGTAC | TTTGAAAAAG | 9480 |
| AGAAAAAGAT | GTGTCTAAGT | GACTATCAGA | TAGCAATGTA | ATGCTCCCTA | ATTGTAAAAA | 9540 |
| AAATCACAAA | TTTGTGAACT | CACGAATTAT | AGACATGTAT | AATTGACCTA | CAGGTCAAGA | 9600 |
| AGTGCCTGTG | GAAGAGCTTG | TTAAAAATAG | AACTACTCAG | CCCCTTCTCA | AATAGCCATC | 9660 |
| GGCCTCAGCC | ATCTGGAAAG | TAAAGTTGGC | AGGTTATGTA | ACTTAGTGTT | TCTTTTACTC | 9720 |
| TGTAGATGTG | TTCAAACTCT | TCCAGGTAAA | CTGCTTAACT | CATTGAGAT | TCTTTGACTA | 9780 |
| ATACTGAGCT | ATGTGCATTT | GCATTTGAA | AAATTATGTA | TCTTTTCCC | ACCATAG | 9837 |

( 2 ) INFORMATION FOR SEQ ID NO:69:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:69:

CTCTGTAACT GCTTATAATC CTG                                23

( 2 ) INFORMATION FOR SEQ ID NO:70:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:70:

CTAGGAAACC TGTACAACTC C                                  21

( 2 ) INFORMATION FOR SEQ ID NO:71:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:71:

GGCTTATTGT GTGCTGATAT C                                  21

( 2 ) INFORMATION FOR SEQ ID NO:72:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:72:

AGAGATCCTT AAGTCGTCAT G                                  21

( 2 ) INFORMATION FOR SEQ ID NO:73:

( i ) SEQUENCE CHARACTERISTICS:
        ( A ) LENGTH: 21 base pairs ( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:73:

CAGTTTCTGT GAGAGAGTAC A 21

( 2 ) INFORMATION FOR SEQ ID NO:74:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:74:

GGCTTACCTG CTCCTGTATT T 21

( 2 ) INFORMATION FOR SEQ ID NO:75:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:75:

GAGGAGGAAT GGGCCTTTAT T 21

( 2 ) INFORMATION FOR SEQ ID NO:76:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:76:

AACCCACAGA ATAGGGCAGG A 21

( 2 ) INFORMATION FOR SEQ ID NO:77:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:77:

GGATACTGGC ATTCTGTGTA AC 22

( 2 ) INFORMATION FOR SEQ ID NO:78:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:78:

ATTTCCAGAT AGTAAGCCCC A                                                        21

( 2 ) INFORMATION FOR SEQ ID NO:79:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:79:

AGCTTGGACG GAAGTCAGAT C                                                        21

( 2 ) INFORMATION FOR SEQ ID NO:80:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:80:

TCTAGCCAAA CCTCGGGTAA C                                                        21

( 2 ) INFORMATION FOR SEQ ID NO:81:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:81:

AATTGTAAAC CTCTGCCC                                                            18

( 2 ) INFORMATION FOR SEQ ID NO:82:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:82:

ATTTCCCAAG CTCATGCT                                                            18

( 2 ) INFORMATION FOR SEQ ID NO:83:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:83:

AGCATGAGCT TGGGAAAT                                                            18

( 2 ) INFORMATION FOR SEQ ID NO:84:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:84:

TGAAGACCTA TCTTTGCC                                                                                     18

( 2 ) INFORMATION FOR SEQ ID NO:85:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:85:

GTTCACAGAG CTCCTCACAC T                                                                                 21

( 2 ) INFORMATION FOR SEQ ID NO:86:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:86:

AGGCCACAGA GTCAACTATG G                                                                                 21

( 2 ) INFORMATION FOR SEQ ID NO:87:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:87:

AGGTCCTATC ACCAAGGGTG T                                                                                 21

( 2 ) INFORMATION FOR SEQ ID NO:88:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:88:

GCTTAGTTAC TTCTTCAAGG C                                                                                 21

( 2 ) INFORMATION FOR SEQ ID NO:89:

( i ) SEQUENCE CHARACTERISTICS:
    ( A ) LENGTH: 21 base pairs (B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:89:

GTAGCTGTTC CCTTTCTCCT A 21

(2) INFORMATION FOR SEQ ID NO:90:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:90:

CCTCAACACT CATGAGAGTG A 21

(2) INFORMATION FOR SEQ ID NO:91:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:91:

TGGTTTAGCA CACCTCTTCA C 21

(2) INFORMATION FOR SEQ ID NO:92:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:92:

GCTTAGCACA AACCCTGTTT C 21

(2) INFORMATION FOR SEQ ID NO:93:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:93:

TTCGCCGTTT GAATTGCTGC 20

(2) INFORMATION FOR SEQ ID NO:94:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: other nucleic acid (x i) SEQUENCE DESCRIPTION: SEQ ID NO:94:

ACCGGTTCAC ACCAACTAGG 20

(2) INFORMATION FOR SEQ ID NO:95:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:95:

GAGATAGGGT CATCATTGAA AC 22

(2) INFORMATION FOR SEQ ID NO:96:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:96:

CATTAGCCAT ACTCTACTTG T 21

(2) INFORMATION FOR SEQ ID NO:97:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:97:

GCTAATTTAA CTCTGTAACT GC 22

(2) INFORMATION FOR SEQ ID NO:98:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:98:

CACTGCAGCA CAGACTAATG TGT 23

(2) INFORMATION FOR SEQ ID NO:99:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:99:

TCTCTCCCTT TAACTGTGGG TTT 23

( 2 ) INFORMATION FOR SEQ ID NO:100:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:100:

GGAGTTGACG AGATTAATAC CTG                   23

( 2 ) INFORMATION FOR SEQ ID NO:101:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:101:

CATGACGACT TAAGGATCTC TT                    22

( 2 ) INFORMATION FOR SEQ ID NO:102:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:102:

CTCAGTTTCC AGAGTACAAA C                    21

( 2 ) INFORMATION FOR SEQ ID NO:103:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:103:

GTGAATTAAA GTCTTTCTGG CC                    22

( 2 ) INFORMATION FOR SEQ ID NO:104:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:104:

ATCTTAGAAA GCAGACAGGG C                    21

( 2 ) INFORMATION FOR SEQ ID NO:105:

( i ) SEQUENCE CHARACTERISTICS:
    ( A ) LENGTH: 21 base pairs (B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:105:

GAGACATTTT ATCCCCTTGT G                                            21

(2) INFORMATION FOR SEQ ID NO:106:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:106:

TCCATGCCTC CAGTCTAAAG T                                            21

(2) INFORMATION FOR SEQ ID NO:107:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:107:

CACTTAAGTT GCACTGGGTA                                              20

(2) INFORMATION FOR SEQ ID NO:108:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:108:

CAACAGGAAG TTGGTCTCAT C                                            21

(2) INFORMATION FOR SEQ ID NO:109:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:109:

TAAAAGGAAG AGCGGCTGTT T                                            21

(2) INFORMATION FOR SEQ ID NO:110:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid ( x i ) SEQUENCE DESCRIPTION: SEQ ID NO:110:

TTAAACCTAA CTGCCACCCT C                                                            21

( 2 ) INFORMATION FOR SEQ ID NO:111:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:111:

CTGAGCTATG TGCATTTGCA                                                              20

( 2 ) INFORMATION FOR SEQ ID NO:112:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:112:

AAGGCTGCTG CTAAACAGAT                                                              20

( 2 ) INFORMATION FOR SEQ ID NO:113:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:113:

ACCTCAGGTG AGGTGAGGGC CCGG                                                         24

( 2 ) INFORMATION FOR SEQ ID NO:114:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:114:

GTGTGCCATT TATGTGATGG CAAAG                                                        25

( 2 ) INFORMATION FOR SEQ ID NO:115:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:115:

GTATACCATT TAGCAGCTGT CCGCC                                                        25